(12) United States Patent
Woodworth et al.

(10) Patent No.: US 7,358,505 B2
(45) Date of Patent: Apr. 15, 2008

(54) APPARATUS FOR FABRICATING A RECONSTITUTION ASSEMBLY

(75) Inventors: Archie Woodworth, Barrington, IL (US); William Reed, Grayslake, IL (US); David J. Adams, Libertyville, IL (US); John A. Martine, Jr., Hendersonville, PA (US); Jeffery Smith, Washington, PA (US); Michael Steeber, Belle Vernon, PA (US); Kim Korzeniewski, West Alexander, PA (US)

(73) Assignee: Baxter International Inc., Deerfield, IL (US)

( * ) Notice: Subject to any disclaimer, the term of this patent is extended or adjusted under 35 U.S.C. 154(b) by 815 days.

(21) Appl. No.: 10/744,946

(22) Filed: Dec. 23, 2003

(65) Prior Publication Data

US 2004/0241041 A1 Dec. 2, 2004

Related U.S. Application Data

(63) Continuation-in-part of application No. 10/106,716, filed on Mar. 26, 2002, now Pat. No. 7,074,216, which is a continuation-in-part of application No. 09/561,666, filed on May 2, 2000, now Pat. No. 6,582,415, which is a continuation of application No. 09/153,816, filed on Sep. 15, 1998, now Pat. No. 6,113,583, application No. 10/744,946, and a continuation-in-part of application No. 09/294,964, filed on Apr. 20, 1999, now Pat. No. 7,264,771.

(51) Int. Cl.
*A61L 2/08* (2006.01)

(52) U.S. Cl. .............................. 250/455.11; 250/492.3; 422/22

(58) Field of Classification Search ..................... None
See application file for complete search history.

(56) References Cited

U.S. PATENT DOCUMENTS

| | | | |
|---|---|---|---|
| 3,330,281 | A | 7/1967 | Visser |
| 3,330,282 | A | 7/1967 | Visser et al. |
| 3,336,924 | A | 8/1967 | Sarnoff et al. |
| 3,552,387 | A | 1/1971 | Stevens |
| 3,785,481 | A | 1/1974 | Allet-Coche |
| 3,788,369 | A | 1/1974 | Killinger |
| 3,796,303 | A | 3/1974 | Allet-Coche |
| 3,809,225 | A | 5/1974 | Allet-Coche |
| 3,826,261 | A | 7/1974 | Killinger |

(Continued)

FOREIGN PATENT DOCUMENTS

DE 1766151 4/1968

(Continued)

*Primary Examiner*—E. Leigh McKane
(74) *Attorney, Agent, or Firm*—Austin J. Foley, Esq.; Bell, Boyd & Lloyd, LLC

(57) ABSTRACT

What is disclosed is an apparatus and method for assembling a reconstitution assembly (1) having a reconstitution device (10) having a first end connected to a flexible diluent container (12), the reconstitution device (10) having a second end connected to a drug vial (14). The reconstitution device (10) and containers, such as drug vials (14) or diluent bags (12), are loaded onto positioning assemblies (27) on a conveyor (90). The positioning assemblies (27) are conveyed to sterilization booths (270). Sterilization fields are generated within the sterilization booths (270), and the containers are sterilely connected to the reconstitution device (10) within the sterile fields.

17 Claims, 55 Drawing Sheets

U.S. PATENT DOCUMENTS

| | | |
|---|---|---|
| 3,917,063 A | 11/1975 | Chibret et al. |
| 3,923,059 A | 12/1975 | Ogle |
| 4,014,330 A | 3/1977 | Genese |
| 4,031,895 A | 6/1977 | Porter |
| 4,059,112 A | 11/1977 | Tischlinger |
| 4,116,196 A | 9/1978 | Kaplan et al. |
| 4,170,994 A | 10/1979 | Komatsu |
| 4,210,142 A | 7/1980 | Wörder |
| 4,210,173 A | 7/1980 | Choksi et al. |
| 4,226,330 A | 10/1980 | Butler |
| 4,243,080 A | 1/1981 | Choksi et al. |
| 4,247,651 A | 1/1981 | Ohno et al. |
| 4,270,533 A | 6/1981 | Andreas |
| 4,303,071 A | 12/1981 | Smith |
| 4,328,802 A | 5/1982 | Curley et al. |
| 4,373,526 A | 2/1983 | Kling |
| 4,392,850 A | 7/1983 | Elias et al. |
| 4,392,851 A | 7/1983 | Elias |
| 4,396,383 A | 8/1983 | Hart |
| 4,410,321 A | 10/1983 | Pearson et al. |
| 4,411,358 A | 10/1983 | Bennwik et al. |
| 4,411,662 A | 10/1983 | Pearson |
| 4,424,056 A | 1/1984 | Urquhart et al. |
| 4,424,057 A | 1/1984 | House |
| 4,432,754 A | 2/1984 | Urquhart et al. |
| 4,432,755 A | 2/1984 | Pearson |
| 4,432,756 A | 2/1984 | Urquhart et al. |
| 4,439,182 A | 3/1984 | Huang |
| 4,439,183 A | 3/1984 | Theeuwes |
| 4,458,733 A | 7/1984 | Lyons |
| 4,458,811 A | 7/1984 | Wilkinson |
| 4,465,471 A | 8/1984 | Harris et al. |
| 4,465,488 A | 8/1984 | Richmond et al. |
| 4,467,588 A | 8/1984 | Carveth |
| 4,469,872 A | 9/1984 | Anderson et al. |
| 4,474,574 A | 10/1984 | Wolfe et al. |
| 4,479,793 A | 10/1984 | Urquhart et al. |
| 4,479,794 A | 10/1984 | Urquhart et al. |
| 4,484,909 A | 11/1984 | Urquhart et al. |
| 4,484,920 A | 11/1984 | Kaufman et al. |
| 4,493,703 A | 1/1985 | Butterfield |
| 4,496,646 A | 1/1985 | Ito |
| 4,505,709 A | 3/1985 | Froning et al. |
| 4,507,113 A | 3/1985 | Dunlap |
| 4,507,114 A | 3/1985 | Bohman et al. |
| 4,511,351 A | 4/1985 | Theeuwes |
| 4,511,352 A | 4/1985 | Theeuwes et al. |
| 4,511,353 A | 4/1985 | Theeuwes |
| 4,515,351 A | 5/1985 | Nakayama et al. |
| 4,515,585 A | 5/1985 | Urquhart et al. |
| 4,516,967 A | 5/1985 | Kopfer |
| 4,516,977 A | 5/1985 | Herbert |
| 4,518,386 A | 5/1985 | Tartaglia |
| 4,519,499 A | 5/1985 | Stone et al. |
| 4,521,211 A | 6/1985 | Theeuwes |
| 4,525,162 A | 6/1985 | Urquhart et al. |
| 4,525,978 A | 7/1985 | Hayase et al. |
| 4,533,348 A | 8/1985 | Wolfe et al. |
| 4,534,757 A | 8/1985 | Geller |
| 4,534,758 A | 8/1985 | Akers et al. |
| 4,538,918 A | 9/1985 | Mittleman |
| 4,539,793 A | 9/1985 | Malek |
| 4,540,089 A | 9/1985 | Maloney |
| 4,540,403 A | 9/1985 | Theeuwes |
| 4,543,094 A | 9/1985 | Barnwell |
| 4,543,101 A | 9/1985 | Crouch |
| 4,548,598 A | 10/1985 | Theeuwes |
| 4,548,599 A | 10/1985 | Urquhart et al. |
| 4,548,606 A | 10/1985 | Larkin |
| 4,550,825 A | 11/1985 | Sutryn et al. |
| 4,552,277 A | 11/1985 | Richardson et al. |
| 4,552,555 A | 11/1985 | Theeuwes |
| 4,552,556 A | 11/1985 | Urquhart et al. |
| 4,561,110 A | 12/1985 | Herbert |
| 4,564,054 A | 1/1986 | Gustavsson |
| 4,568,331 A | 2/1986 | Fischer et al. |
| 4,568,336 A | 2/1986 | Cooper |
| 4,568,346 A | 2/1986 | van Dijk |
| 4,573,967 A | 3/1986 | Hargrove et al. |
| 4,573,993 A | 3/1986 | Hoag et al. |
| 4,576,211 A | 3/1986 | Valentini et al. |
| 4,579,553 A | 4/1986 | Urquhart et al. |
| 4,581,016 A | 4/1986 | Gettig |
| 4,583,971 A | 4/1986 | Bocquet et al. |
| 4,583,981 A | 4/1986 | Urquhart et al. |
| 4,586,922 A | 5/1986 | Theeuwes |
| 4,589,867 A | 5/1986 | Israel |
| 4,589,879 A | 5/1986 | Pearson |
| 4,590,234 A | 5/1986 | Tasaka et al. |
| 4,596,555 A | 6/1986 | Theeuwes |
| 4,601,704 A | 7/1986 | Larkin |
| 4,602,910 A | 7/1986 | Larkin |
| 4,606,734 A | 8/1986 | Larkin et al. |
| 4,607,671 A | 8/1986 | Aalto et al. |
| 4,608,043 A | 8/1986 | Larkin |
| 4,610,684 A | 9/1986 | Knox et al. |
| 4,613,326 A | 9/1986 | Szwarc |
| 4,614,267 A | 9/1986 | Larkin |
| 4,614,515 A | 9/1986 | Tripp et al. |
| 4,623,334 A | 11/1986 | Riddell |
| 4,629,080 A | 12/1986 | Carveth |
| 4,630,727 A | 12/1986 | Feriani et al. |
| 4,632,244 A | 12/1986 | Landau |
| 4,637,934 A | 1/1987 | White |
| 4,650,475 A | 3/1987 | Smith et al. |
| 4,662,878 A | 5/1987 | Lindmayer |
| 4,664,650 A | 5/1987 | Urquhart et al. |
| 4,668,219 A | 5/1987 | Israel |
| 4,673,404 A | 6/1987 | Gustavsson |
| 4,675,020 A | 6/1987 | McPhee |
| 4,692,144 A | 9/1987 | Carpenter |
| 4,693,706 A | 9/1987 | Ennis, III |
| 4,695,272 A | 9/1987 | Berglund et al. |
| 4,703,864 A | 11/1987 | Larkin et al. |
| 4,715,854 A | 12/1987 | Vaillancourt |
| 4,717,388 A | 1/1988 | Steer et al. |
| 4,722,733 A | 2/1988 | Howson |
| 4,723,956 A | 2/1988 | Schnell et al. |
| 4,727,985 A | 3/1988 | McNeirney et al. |
| 4,731,053 A | 3/1988 | Hoffman |
| 4,735,608 A | 4/1988 | Sardam |
| 4,740,103 A | 4/1988 | Theeuwes |
| 4,740,197 A | 4/1988 | Theeuwes |
| 4,740,198 A | 4/1988 | Theeuwes |
| 4,740,199 A | 4/1988 | Theeuwes |
| 4,740,200 A | 4/1988 | Theeuwes |
| 4,740,201 A | 4/1988 | Theeuwes |
| 4,741,734 A | 5/1988 | Theeuwes |
| 4,741,735 A | 5/1988 | Theeuwes |
| 4,743,229 A | 5/1988 | Chu |
| 4,747,834 A | 5/1988 | Prindle |
| 4,752,292 A | 6/1988 | Lopez et al. |
| 4,757,911 A | 7/1988 | Larkin et al. |
| 4,759,756 A | 7/1988 | Forman et al. |
| 4,778,453 A | 10/1988 | Lopez |
| 4,781,679 A | 11/1988 | Larkin |
| 4,782,841 A | 11/1988 | Lopez |
| 4,784,259 A | 11/1988 | Grabenkort |
| 4,784,658 A | 11/1988 | Grabenkort |
| 4,785,858 A | 11/1988 | Valentini et al. |
| 4,786,279 A | 11/1988 | Wilkinson et al. |
| 4,787,429 A | 11/1988 | Valentini et al. |
| 4,790,820 A | 12/1988 | Theeuwes |
| 4,804,360 A | 2/1989 | Kamen |

| Patent | Date | Name |
|---|---|---|
| 4,804,366 A | 2/1989 | Zdeb et al. |
| 4,808,381 A | 2/1989 | McGregor et al. |
| 4,816,024 A | 3/1989 | Sitar et al. |
| 4,819,659 A | 4/1989 | Sitar |
| 4,820,269 A | 4/1989 | Riddell |
| 4,822,351 A | 4/1989 | Purcell |
| 4,832,690 A | 5/1989 | Kuu |
| 4,834,149 A | 5/1989 | Fournier et al. |
| 4,834,152 A | 5/1989 | Howson et al. |
| 4,842,028 A | 6/1989 | Kaufman et al. |
| 4,850,978 A | 7/1989 | Dudar et al. |
| 4,857,052 A | 8/1989 | Theeuwes |
| 4,861,335 A | 8/1989 | Reynolds |
| 4,861,585 A | 8/1989 | Galef, Jr. et al. |
| 4,865,354 A | 9/1989 | Allen |
| 4,871,354 A | 10/1989 | Conn et al. |
| 4,871,360 A | 10/1989 | Theeuwes |
| 4,871,463 A | 10/1989 | Taylor et al. |
| 4,872,494 A | 10/1989 | Coccia |
| 4,874,366 A | 10/1989 | Zdeb et al. |
| 4,874,368 A | 10/1989 | Miller et al. |
| 4,883,483 A | 11/1989 | Lindmayer |
| 4,886,495 A | 12/1989 | Reynolds |
| 4,898,209 A | 2/1990 | Zbed |
| 4,906,103 A | 3/1990 | Kao |
| 4,908,019 A | 3/1990 | Urquhart et al. |
| 4,909,290 A | 3/1990 | Coccia |
| 4,911,708 A | 3/1990 | Maezaki et al. |
| 4,915,689 A | 4/1990 | Theeuwes |
| 4,927,013 A | 5/1990 | Van Brunt et al. |
| 4,927,423 A | 5/1990 | Malmborg |
| 4,927,605 A | 5/1990 | Dorn et al. |
| 4,931,048 A | 6/1990 | Lopez |
| 4,936,445 A | 6/1990 | Grabenkort |
| 4,936,829 A | 6/1990 | Zdeb et al. |
| 4,936,841 A | 6/1990 | Aoki et al. |
| 4,944,736 A | 7/1990 | Holtz |
| 4,948,000 A | 8/1990 | Grabenkort |
| 4,950,237 A | 8/1990 | Henault et al. |
| 4,961,495 A | 10/1990 | Yoshida et al. |
| 4,968,299 A | 11/1990 | Ahlstrand et al. |
| 4,969,883 A | 11/1990 | Gilbert et al. |
| 4,973,307 A | 11/1990 | Theeuwes |
| 4,978,337 A | 12/1990 | Theeuwes |
| 4,979,942 A | 12/1990 | Wolf et al. |
| 4,982,875 A | 1/1991 | Pozzi et al. |
| 4,983,164 A | 1/1991 | Hook et al. |
| 4,985,016 A | 1/1991 | Theeuwes et al. |
| 4,986,322 A | 1/1991 | Chibret et al. |
| 4,994,031 A | 2/1991 | Theeuwes |
| 4,994,056 A | 2/1991 | Ikeda |
| 4,996,579 A | 2/1991 | Chu |
| 4,997,083 A | 3/1991 | Loretti et al. |
| 4,997,430 A | 3/1991 | Van der Heiden et al. |
| 5,002,530 A | 3/1991 | Recker et al. |
| 5,009,654 A * | 4/1991 | Minshall et al. ............ 604/410 |
| 5,023,119 A | 6/1991 | Yamakoshi |
| 5,024,657 A | 6/1991 | Needham et al. |
| 5,030,203 A | 7/1991 | Wolf, Jr. et al. |
| 5,032,117 A | 7/1991 | Motta |
| 5,045,081 A | 9/1991 | Dysarz |
| 5,049,129 A | 9/1991 | Zdeb et al. |
| 5,049,135 A | 9/1991 | Davis |
| 5,061,264 A | 10/1991 | Scarrow |
| 5,064,059 A | 11/1991 | Ziegler et al. |
| 5,069,671 A | 12/1991 | Theeuwes |
| 5,074,844 A | 12/1991 | Zdeb et al. |
| 5,074,849 A | 12/1991 | Sachse |
| D323,389 S | 1/1992 | Aoki et al. |
| 5,080,652 A | 1/1992 | Sancoff et al. |
| 5,084,040 A | 1/1992 | Sutter |
| 5,088,996 A | 2/1992 | Kopfer et al. |
| 5,100,394 A | 3/1992 | Dudar et al. |
| 5,102,408 A | 4/1992 | Hamacher |
| 5,104,375 A | 4/1992 | Wolf et al. |
| 5,114,004 A | 5/1992 | Isono et al. |
| 5,114,411 A | 5/1992 | Haber et al. |
| 5,116,315 A | 5/1992 | Capozzi et al. |
| 5,116,316 A | 5/1992 | Sertic et al. |
| 5,117,875 A | 6/1992 | Marrucchi |
| 5,122,123 A | 6/1992 | Vaillancourt |
| 5,125,892 A | 6/1992 | Drudik |
| 5,125,908 A | 6/1992 | Cohen |
| 5,126,175 A | 6/1992 | Yamakoshi |
| 5,129,894 A | 7/1992 | Sommermeyer et al. |
| 5,137,511 A | 8/1992 | Reynolds |
| 5,147,324 A | 9/1992 | Skakoon et al. |
| 5,152,965 A | 10/1992 | Fisk et al. |
| 5,156,598 A | 10/1992 | Skakoon et al. |
| 5,158,546 A | 10/1992 | Haber et al. |
| 5,160,320 A | 11/1992 | Yum et al. |
| 5,167,642 A | 12/1992 | Fowles |
| 5,169,388 A | 12/1992 | McPhee |
| 5,171,214 A | 12/1992 | Kolber et al. |
| 5,171,219 A | 12/1992 | Fujioka et al. |
| 5,171,220 A | 12/1992 | Morimoto |
| 5,176,634 A | 1/1993 | Smith et al. |
| 5,176,673 A | 1/1993 | Marrucchi |
| 5,181,909 A | 1/1993 | McFarlane |
| 5,186,323 A | 2/1993 | Pfleger |
| 5,188,615 A | 2/1993 | Haber et al. |
| 5,188,629 A | 2/1993 | Shimoda |
| 5,195,658 A | 3/1993 | Hoshino |
| 5,195,986 A | 3/1993 | Kamen |
| 5,196,001 A | 3/1993 | Kao |
| 5,199,947 A | 4/1993 | Lopez et al. |
| 5,199,948 A | 4/1993 | McPhee |
| 5,200,200 A | 4/1993 | Veech |
| 5,201,705 A | 4/1993 | Berglund et al. |
| 5,207,509 A | 5/1993 | Herbert |
| 5,209,201 A | 5/1993 | Horie et al. |
| 5,209,347 A | 5/1993 | Fabisiewicz et al. |
| 5,211,201 A | 5/1993 | Kamen et al. |
| 5,211,285 A | 5/1993 | Haber et al. |
| 5,222,946 A | 6/1993 | Kamen |
| 5,226,878 A | 7/1993 | Young |
| 5,226,900 A | 7/1993 | Bancsi et al. |
| RE34,365 E | 8/1993 | Theeuwes |
| 5,232,029 A | 8/1993 | Knox et al. |
| 5,232,109 A | 8/1993 | Tirrell et al. |
| 5,246,142 A | 9/1993 | DiPalma et al. |
| 5,247,972 A | 9/1993 | Tetreault |
| 5,250,028 A | 10/1993 | Theeuwes et al. |
| 5,257,985 A | 11/1993 | Puhl |
| 5,257,986 A | 11/1993 | Herbert et al. |
| 5,257,987 A | 11/1993 | Athayde et al. |
| 5,259,843 A | 11/1993 | Watanabe et al. |
| 5,259,954 A | 11/1993 | Taylor |
| 5,261,902 A | 11/1993 | Okada et al. |
| 5,267,646 A | 12/1993 | Inoue et al. |
| 5,267,957 A | 12/1993 | Kriesel et al. |
| 5,279,576 A | 1/1994 | Loo et al. |
| 5,279,579 A | 1/1994 | D'Amico |
| 5,279,583 A | 1/1994 | Shober, Jr. et al. |
| 5,281,198 A | 1/1994 | Haber et al. |
| 5,281,206 A | 1/1994 | Lopez |
| 5,286,257 A | 2/1994 | Fischer |
| 5,287,961 A | 2/1994 | Herran |
| 5,289,585 A | 2/1994 | Kock et al. |
| 5,289,858 A | 3/1994 | Grabenkort |
| 5,302,603 A | 4/1994 | Crawley et al. |
| 5,303,751 A | 4/1994 | Slater et al. |
| 5,304,130 A | 4/1994 | Button et al. |
| 5,304,163 A | 4/1994 | Bonnici et al. |
| 5,304,165 A | 4/1994 | Haber et al. |
| 5,306,242 A | 4/1994 | Joyce et al. |

| Patent Number | Date | Inventor |
|---|---|---|
| 5,308,287 A | 5/1994 | Gunsing |
| 5,308,347 A | 5/1994 | Sunago et al. |
| 5,320,603 A | 6/1994 | Vetter et al. |
| 5,328,464 A | 7/1994 | Kriesel et al. |
| 5,330,048 A | 7/1994 | Haber et al. |
| 5,330,426 A | 7/1994 | Kriesel et al. |
| 5,330,450 A | 7/1994 | Lopez |
| 5,330,462 A | 7/1994 | Nakamura |
| 5,330,464 A | 7/1994 | Mathias et al. |
| 5,332,399 A | 7/1994 | Grabenkort et al. |
| 5,334,178 A | 8/1994 | Haber et al. |
| 5,334,180 A | 8/1994 | Adolf et al. |
| 5,334,188 A | 8/1994 | Inoue et al. |
| 5,335,773 A | 8/1994 | Haber et al. |
| 5,336,180 A | 8/1994 | Kriesel et al. |
| 5,342,346 A | 8/1994 | Honda et al. |
| 5,342,347 A | 8/1994 | Kikuchi et al. |
| 5,344,414 A | 9/1994 | Lopez et al. |
| 5,348,060 A | 9/1994 | Futagawa et al. |
| 5,348,600 A | 9/1994 | Ishii |
| 5,350,372 A | 9/1994 | Ikeda et al. |
| 5,350,546 A | 9/1994 | Takeuchi et al. |
| 5,352,191 A | 10/1994 | Sunago et al. |
| 5,352,196 A | 10/1994 | Haber et al. |
| 5,352,210 A | 10/1994 | Marrucchi |
| 5,353,961 A | 10/1994 | Debush |
| 5,356,380 A | 10/1994 | Hoekwater et al. |
| 5,358,501 A | 10/1994 | Meyer |
| 5,360,410 A | 11/1994 | Wacks |
| 5,364,350 A | 11/1994 | Dittmann |
| 5,364,369 A | 11/1994 | Reynolds |
| 5,364,371 A | 11/1994 | Kamen |
| 5,364,384 A | 11/1994 | Grabenkort et al. |
| 5,368,586 A | 11/1994 | Van Der Heiden et al. |
| 5,370,164 A | 12/1994 | Galloway |
| 5,373,966 A | 12/1994 | O'Reilly et al. |
| 5,374,264 A | 12/1994 | Wadsworth, Jr. |
| 5,376,079 A | 12/1994 | Holm |
| 5,380,281 A | 1/1995 | Tomellini et al. |
| 5,380,287 A | 1/1995 | Kikuchi et al. |
| 5,380,315 A | 1/1995 | Isono et al. |
| 5,385,545 A | 1/1995 | Kriesel et al. |
| 5,385,546 A | 1/1995 | Kriesel et al. |
| 5,385,547 A | 1/1995 | Wong et al. |
| 5,386,372 A | 1/1995 | Kobayashi et al. |
| 5,393,497 A | 2/1995 | Haber et al. |
| 5,397,303 A | 3/1995 | Sancoff et al. |
| 5,398,851 A | 3/1995 | Sancoff et al. |
| 5,401,253 A | 3/1995 | Reynolds |
| 5,409,141 A | 4/1995 | Kikuchi et al. |
| 5,423,421 A | 6/1995 | Inoue et al. |
| 5,423,753 A | 6/1995 | Fowles et al. |
| 5,423,793 A | 6/1995 | Isono et al. |
| 5,423,796 A | 6/1995 | Shikhman et al. |
| 5,425,447 A | 6/1995 | Farina |
| 5,425,528 A | 6/1995 | Rains et al. |
| 5,429,256 A | 7/1995 | Kestenbaum |
| 5,429,603 A | 7/1995 | Morris |
| 5,429,614 A | 7/1995 | Fowles et al. |
| 5,435,076 A | 7/1995 | Hjertman et al. |
| 5,445,631 A | 8/1995 | Uchida |
| 5,456,678 A | 10/1995 | Nicoletti |
| 5,458,593 A | 10/1995 | Macabasco et al. |
| 5,462,526 A | 10/1995 | Barney et al. |
| 5,464,123 A | 11/1995 | Scarrow |
| 5,467,337 A | 11/1995 | Matsumoto |
| 5,470,327 A | 11/1995 | Helgren et al. |
| 5,472,022 A | 12/1995 | Michel et al. |
| 5,472,422 A | 12/1995 | Ljungquist |
| 5,474,540 A | 12/1995 | Miller et al. |
| 5,478,337 A | 12/1995 | Okamoto et al. |
| 5,484,406 A | 1/1996 | Wong et al. |
| 5,484,410 A | 1/1996 | Kriesel et al. |
| 5,489,266 A | 2/1996 | Grimard |
| 5,490,848 A | 2/1996 | Finley et al. |
| 5,492,147 A | 2/1996 | Challender et al. |
| 5,492,219 A | 2/1996 | Stupar |
| 5,493,774 A | 2/1996 | Grabenkort |
| 5,494,190 A | 2/1996 | Boettcher |
| 5,501,887 A | 3/1996 | Tanaka et al. |
| 5,509,898 A | 4/1996 | Isono et al. |
| 5,510,115 A | 4/1996 | Breillatt, Jr. et al. |
| 5,514,090 A | 5/1996 | Kriesel et al. |
| 5,520,972 A | 5/1996 | Ezaki et al. |
| 5,522,804 A | 6/1996 | Lynn |
| 5,526,853 A | 6/1996 | McPhee et al. |
| 5,531,683 A | 7/1996 | Kriesel et al. |
| 5,533,389 A | 7/1996 | Kamen et al. |
| 5,533,973 A | 7/1996 | Piontek et al. |
| 5,533,994 A | 7/1996 | Meyer |
| 5,535,746 A | 7/1996 | Hoover et al. |
| 5,536,469 A | 7/1996 | Jonsson et al. |
| 5,538,506 A | 7/1996 | Farris et al. |
| 5,540,674 A | 7/1996 | Karas et al. |
| 5,547,471 A | 8/1996 | Thompson et al. |
| 5,554,125 A | 9/1996 | Reynolds |
| 5,554,128 A | 9/1996 | Hedges |
| 5,560,403 A | 10/1996 | Balteau et al. |
| 5,566,729 A | 10/1996 | Grabenkort et al. |
| 5,569,191 A | 10/1996 | Meyer |
| 5,569,192 A | 10/1996 | van der Wal |
| 5,569,193 A | 10/1996 | Hofstetter et al. |
| 5,573,527 A | 11/1996 | Macabasco et al. |
| 5,575,310 A | 11/1996 | Kamen et al. |
| 5,577,369 A | 11/1996 | Becker et al. |
| 5,584,808 A | 12/1996 | Healy |
| 5,593,028 A | 1/1997 | Haber et al. |
| 5,595,314 A | 1/1997 | Weiler |
| 5,596,193 A | 1/1997 | Chutjian et al. |
| 5,603,695 A | 2/1997 | Erickson |
| 5,603,696 A | 2/1997 | Williams et al. |
| 5,605,542 A | 2/1997 | Tanaka et al. |
| 5,611,792 A | 3/1997 | Gustafsson |
| 5,620,434 A | 4/1997 | Brony |
| 5,624,405 A | 4/1997 | Futagawa et al. |
| 5,641,010 A | 6/1997 | Maier |
| 5,669,891 A | 9/1997 | Vaillancourt |
| 5,688,254 A | 11/1997 | Lopez et al. |
| 5,709,666 A | 1/1998 | Reynolds |
| 5,714,119 A * | 2/1998 | Kawagoe et al. ............ 422/21 |
| 5,743,312 A | 4/1998 | Pfeifer et al. |
| 5,827,262 A | 10/1998 | Neftel et al. |
| 5,897,526 A | 4/1999 | Vaillancourt |
| 5,989,237 A | 11/1999 | Fowles et al. |
| 6,019,750 A | 2/2000 | Fowles et al. |
| 6,022,339 A | 2/2000 | Fowles et al. |
| 6,063,068 A | 5/2000 | Fowles et al. |
| 6,071,270 A | 6/2000 | Fowles et al. |
| 6,090,092 A | 7/2000 | Fowles et al. |
| 6,140,657 A * | 10/2000 | Wakalopulos et al. ... 250/492.3 |
| 6,189,292 B1 * | 2/2001 | Odell et al. .................. 53/425 |
| 6,378,714 B1 | 4/2002 | Jansen et al. |
| 6,610,040 B1 | 8/2003 | Fowles et al. |
| 2003/0091468 A1 | 5/2003 | Buchanan |
| 2005/0133729 A1* | 6/2005 | Woodworth et al. ... 250/455.11 |
| 2006/0110282 A1* | 5/2006 | Bilstad et al. ................ 422/22 |

FOREIGN PATENT DOCUMENTS

| | | |
|---|---|---|
| DE | 1913926 | 3/1969 |
| EP | 0 091 310 A2 | 4/1983 |
| EP | 0 285 424 A1 | 3/1988 |
| EP | 0 335 378 A2 | 4/1989 |
| EP | 0 363 770 A1 | 4/1990 |
| EP | 0 395 758 A1 | 7/1990 |
| EP | 0 499 764 A1 | 8/1991 |

| | | |
|---|---|---|
| EP | 0 692 235 A1 | 7/1994 |
| EP | 0961608 A | 12/1999 |
| GB | 2 211 104 A | 10/1987 |
| JP | 4156849 A2 | 10/1990 |
| JP | 7255820 A2 | 3/1994 |
| JP | 8238300 A2 | 3/1995 |
| JP | 09-276370 | 4/1996 |
| JP | 10024089 A2 | 1/1998 |
| WO | WO 83/03540 | 10/1983 |
| WO | WO 85/03432 | 1/1985 |
| WO | WO 90/03536 | 9/1989 |
| WO | WO 93/02723 | 6/1992 |
| WO | WO 92/11897 | 7/1992 |
| WO | WO 93/09825 | 5/1993 |
| WO | WO 97/25015 | 7/1997 |

\* cited by examiner

FIG. 1
FIG. 2
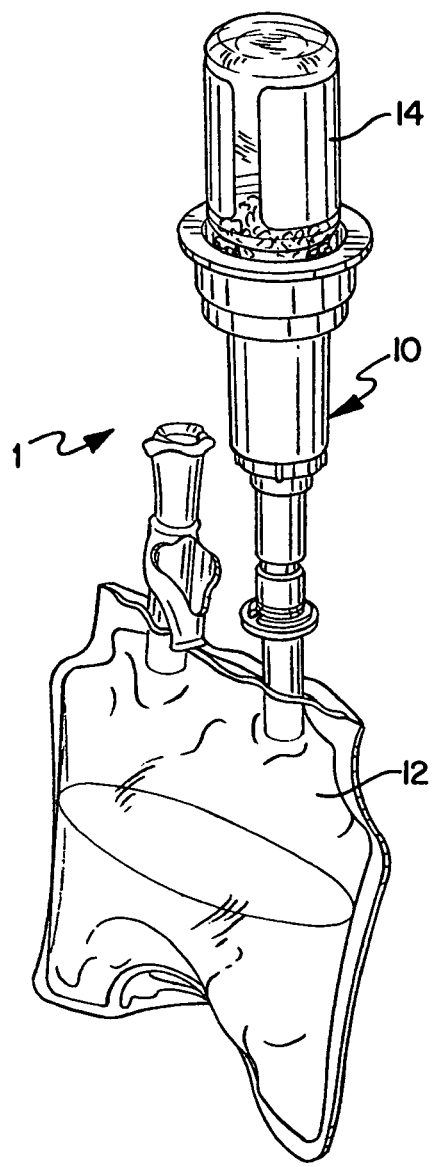
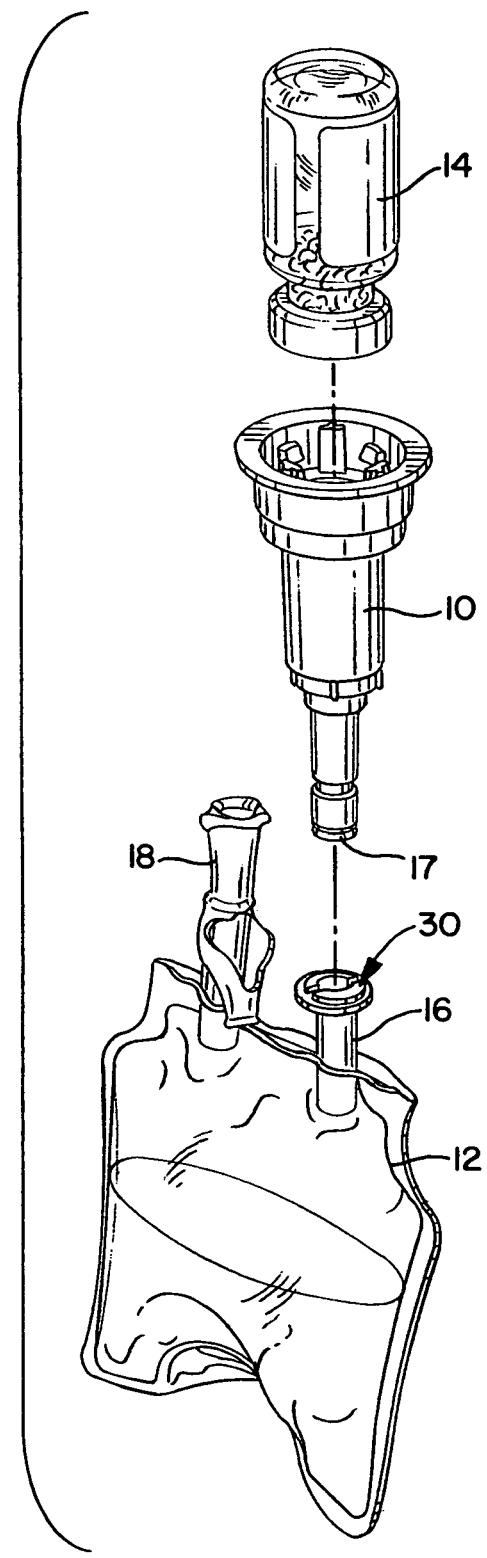

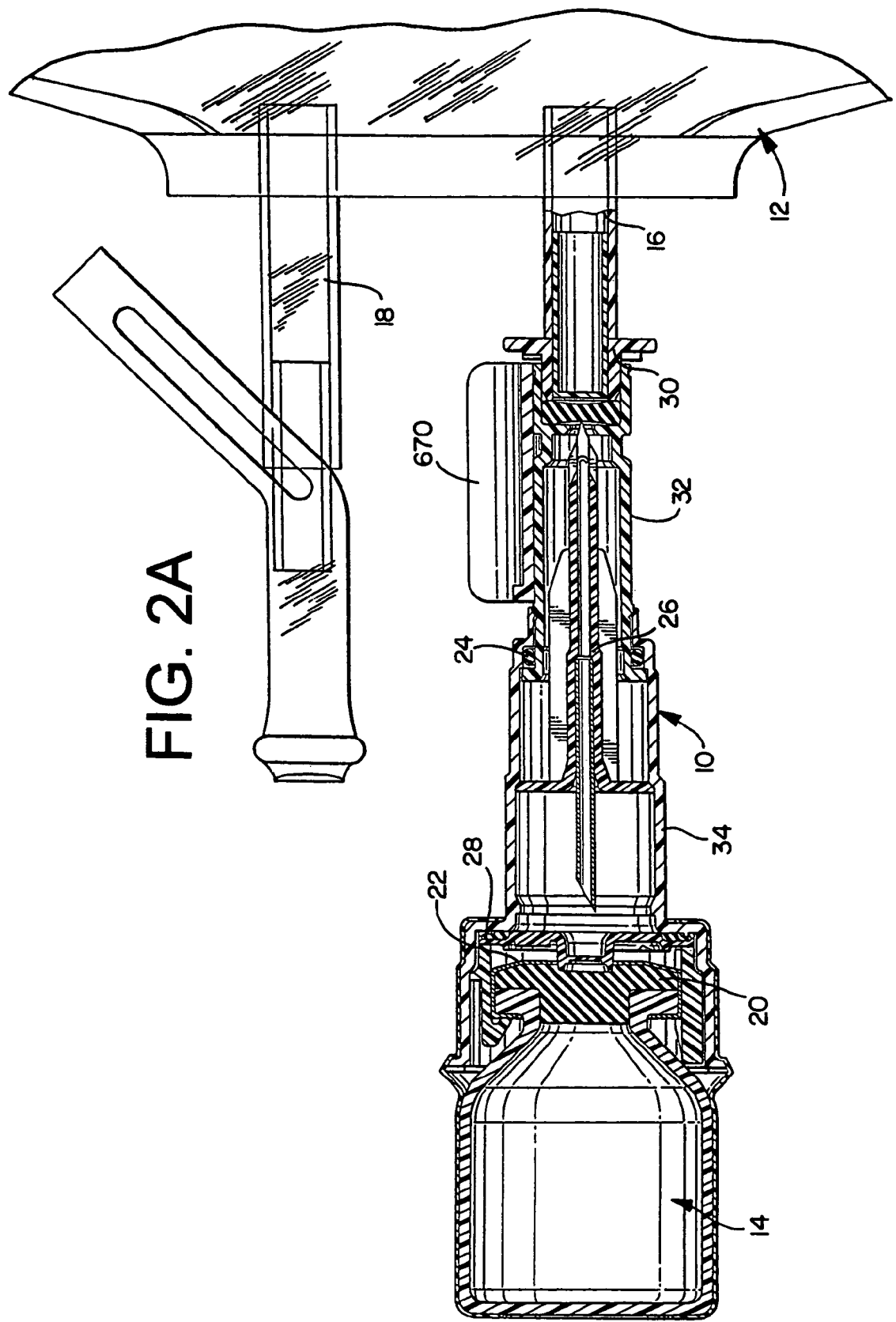

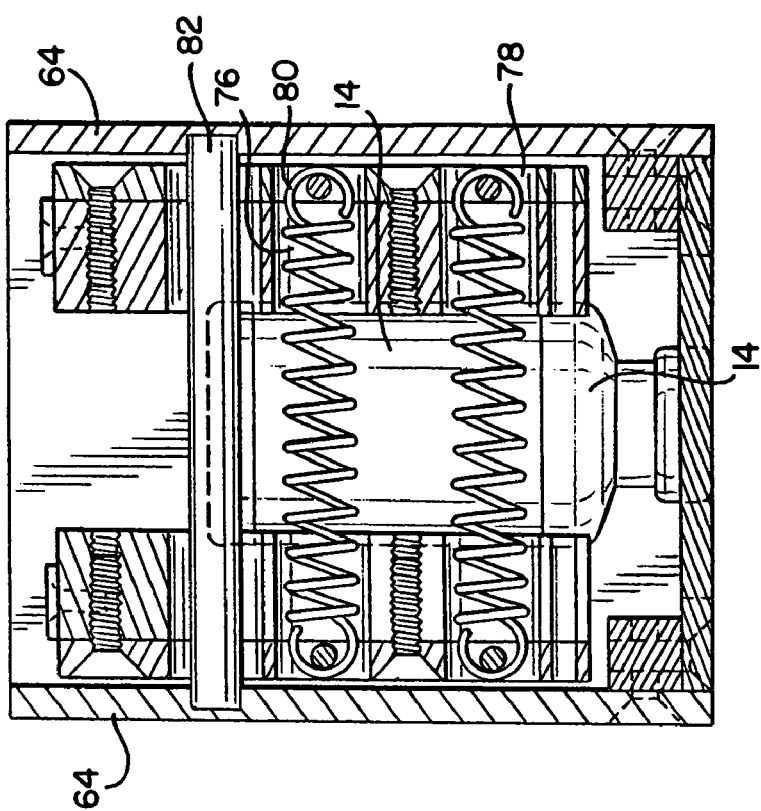
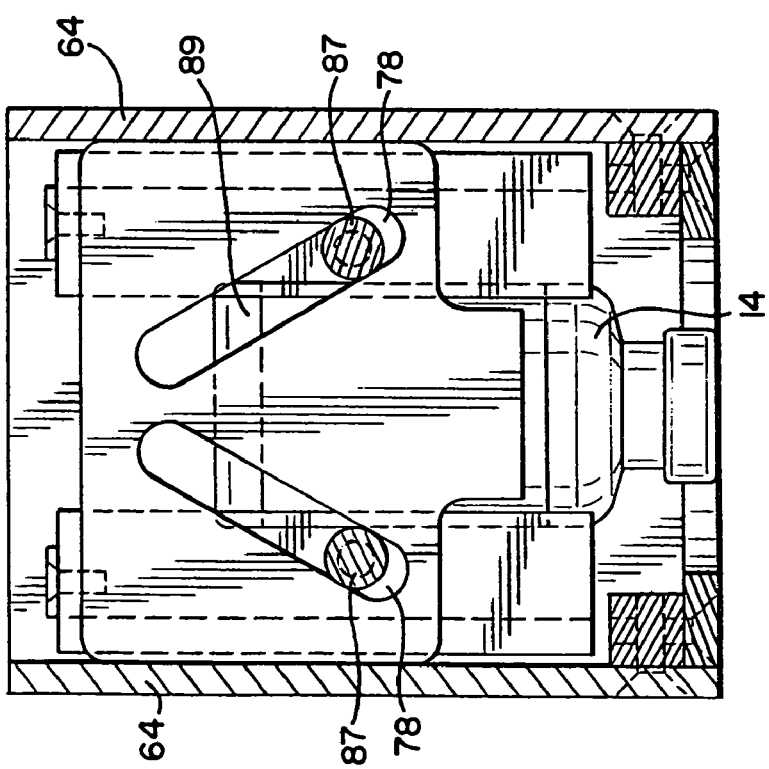

APPARATUS FOR FABRICATING A RECONSTITUTION ASSEMBLY

RELATED APPLICATIONS

This is a continuation-in-part application of U.S. application Ser. No. 10/106,716 filed Mar. 26, 2002 now U.S. Pat. No. 7,074,216 and entitled "Sliding Reconstitution Device for a Diluent Container," which is a continuation-in-part application of U.S. application Ser. No. 09/561,666, filed May 2, 2000, now U.S. Pat. No. 6,582,415, which is a continuation application of U.S. application Ser. No. 09/153,816, filed Sep. 15, 1998, now U.S. Pat. No. 6,113,583, issued Sep. 5, 2000, and this is also a continuation-in-part application of U.S. patent application Ser. No. 09/294,964, filed Apr. 20, 1999 now U.S. Pat. No. 7,7264,771 entitled "Method and Apparatus For Manipulating Pre-Sterilized Components In An Active Sterile Field." Each of these applications are incorporated herein by reference and made a part hereof.

TECHNICAL FIELD

The present invention relates generally to drug reconstitution. More specifically, the present invention relates to an apparatus for assembling a reconstitution assembly wherein containers are sterilely connected to a drug reconstitution device.

BACKGROUND OF THE INVENTION

Reconstitution devices, as well as the apparatuses that assemble reconstitution devices are known in the art. Reconstitution devices are generally used to mix a drug with a diluent to form a reconstituted drug that is delivered to a patient. Certain reconstitution devices are shown, for example in U.S. Pat. Nos. 6,022,339 and 6,071,270 to Fowles et al.

While reconstitution devices and their associated fabricating apparatuses according to the prior art provide a number of advantageous features, they nevertheless have certain limitations. The present invention seeks to overcome certain of these limitations and other drawbacks of the prior art, and to provide new features not heretofore available.

SUMMARY OF THE INVENTION

The present invention provides an apparatus for assembling a reconstitution assembly wherein a first container and a second container are connected to a reconstitution device to form the reconstitution assembly.

According to a first aspect of the invention, the reconstitution assembly generally comprises a first container, a second container and a reconstitution device. The first container is generally a diluent container and can be, for example, a flexible diluent bag or syringe. The second container is generally a drug container and can be, for example, a drug vial containing a drug in powdered, lyophilized or liquid form. The diluent container and drug vial are sterilely connected to the reconstitution device. The reconstitution device has a piercing member that is hermetically sealed from an outside environment. The reconstitution device has an inactivated position and an activated position. When the reconstitution device is moved from the inactivated position to the activated position, the piercing member enters the first container and the second container to establish fluid communication between the containers. In the activated position, fluid from the diluent container passes through the piercing member and into the drug vial to reconstitute the drug. The reconstituted drug is transferred into the diluent container wherein it can be delivered to a patient from the diluent container.

According to a further aspect of the invention, an apparatus for the sterile connecting of a container and a reconstitution device includes a sterilization source. While the sterilization source can take many different forms, in one preferred embodiment, the sterilization source is capable of emitting radiation to define a sterilizing field. The apparatus further includes a connecting mechanism positioned proximate the sterilization source. The connecting mechanism is configured to hold the container and reconstitution device in a sterilizing field. The connecting mechanism includes a movable member configured to provide relative motion between the container and reconstitution device to connect the container to the reconstitution device in the sterilizing field.

According to another aspect of the present invention, an apparatus for the sterile connecting of a container and a reconstitution device includes a low energy electron sterilization source that provides an energy within a range of from about 60 to about 150 KeV to define a sterilizing field. The apparatus further includes a connecting mechanism positioned proximate the sterilization source. The connecting mechanism is configured to hold the container and reconstitution device in a sterilizing field. The connecting mechanism includes a movable member configured to provide relative motion between the container and reconstitution device to connect the container to the reconstitution device in the sterilizing field.

According to another aspect of the present invention, an apparatus for the sterile connecting of a container and a reconstitution device includes a first electron sterilization source positioned generally opposite a second electron sterilization source. A sterilizing field from the first electron sterilization source overlaps a sterilizing field from the second electron sterilization source radiation to define a concentrated field. The apparatus further includes a connecting mechanism positioned proximate the sterilization sources. The connecting mechanism is configured to hold the container and reconstitution device in the concentrated field. The connecting mechanism includes a movable member configured to move the reconstitution device into connection with the vial in the concentrated field. A housing is positioned around the sterilization sources and the connecting mechanism.

According to another aspect of the present invention, an apparatus for the sterile connecting of a vial and a drug reconstitution device includes a vial pallet. A device loader is configured for loading a reconstitution device onto the vial pallet. A container loader is configured for loading a vial onto the vial pallet. The apparatus includes a first sterilization booth for the sterile connecting of the reconstitution device and vial. A vial pallet conveyor conveys the vial pallet between the device loader, the container loader, and the first sterilization booth.

According to another aspect of the present invention, an apparatus for the sterile connecting of a container and a drug reconstitution device includes a vial pallet. A device loader is configured for loading a reconstitution device onto the vial pallet. A container loader is configured for loading a vial onto the vial pallet. The apparatus includes a first sterilization booth for the sterile connecting of the reconstitution device and vial. A vial pallet conveyor conveys the vial pallet between the device loader, the container loader, and the first sterilization booth. The apparatus also includes a bag pallet. In addition, a device and vial subassembly loader is provided for loading a device and container subassembly onto the bag pallet. A bag loader is configured to load a bag onto the bag pallet. A second sterilization booth is configured for the sterile connecting of the device and container subassembly and the bag. A bag pallet conveyor conveys the bag pallet between the device and vial subassembly loader, the bag loader, and the second sterilization booth.

According to another aspect of the present invention, a method for the sterile connecting of a container and a drug reconstitution device includes the steps of providing a container, a drug reconstitution device and a positioning assembly. The container and the drug reconstitution device are positioned in the positioning assembly. The positioning assembly is conveyed to a connection area. A sterilizing field is created within the connection area. The container is connected to the drug reconstitution device within the sterilizing field.

Other features and advantages of the invention will become apparent from the following description taken in conjunction with the following drawings.

BRIEF DESCRIPTION OF THE DRAWINGS

FIG. 1 is a perspective view of a reconstitution assembly showing a reconstitution device connected to a first container and a second container according to one embodiment of the present invention;

FIG. 2 is an exploded view of the reconstitution assembly of FIG. 1;

FIG. 2A is a partial cross-sectional view of the reconstitution assembly of the present invention of FIG. 1 with only a portion of the first container shown;

FIG. 13 is a cross-sectional view of the container holder support of the positioning assembly taken along lines 13-13 of FIG. 11;

FIG. 14 is a cross-sectional view of the container holder support of the positioning assembly taken along line 14-14 of FIG. 11;

DETAILED DESCRIPTION OF THE PREFERRED EMBODIMENTS

Figure 3:
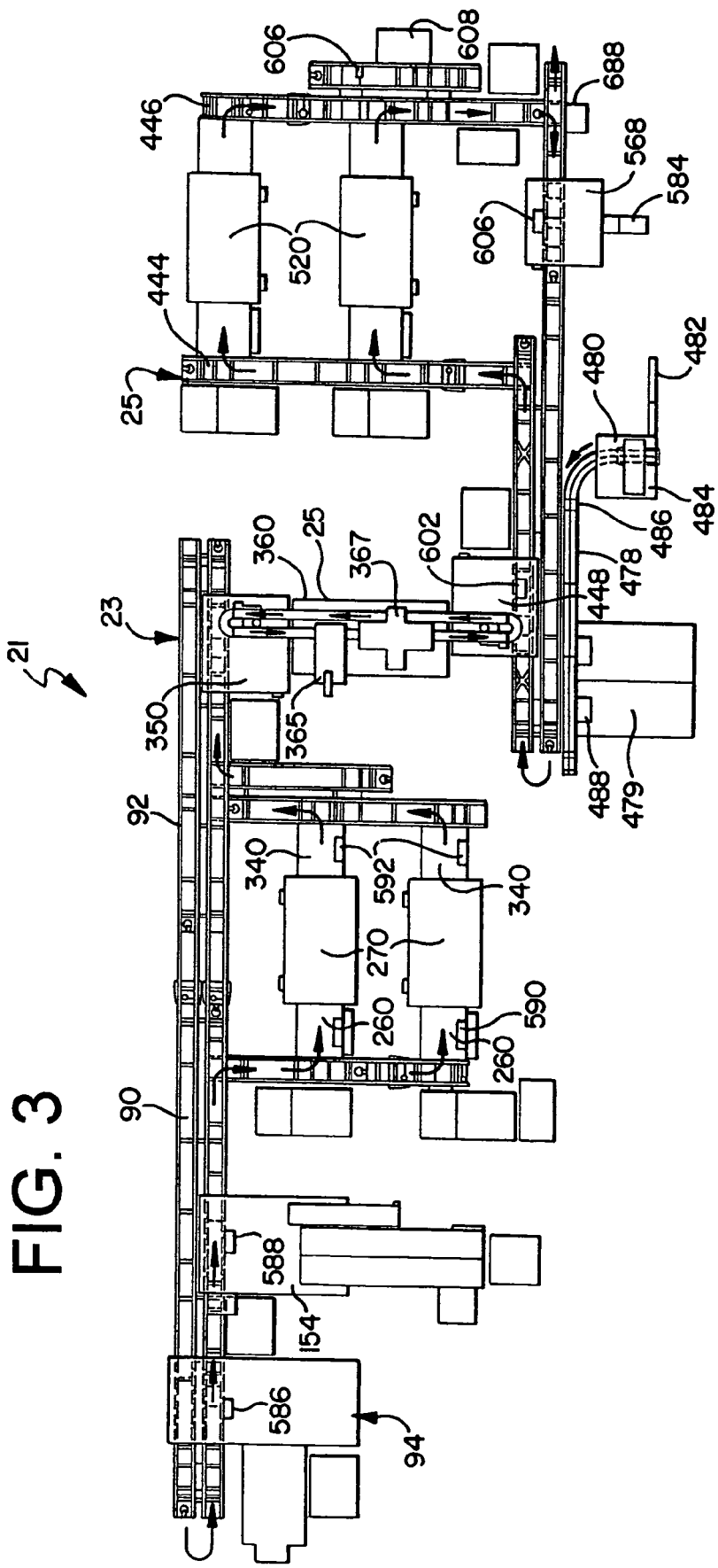
FIG. 3 is a schematic plan view of a system for connecting and assembling the reconstitution assembly according to one embodiment of the present invention.

While the invention is susceptible of embodiment in many different forms, there is shown in the drawings and will herein be described in detail preferred embodiments of the invention. It is to be understood that the present disclosure is to be considered as an exemplification of the principles of the invention. This disclosure is not intended to limit the broad aspect of the invention to the illustrated embodiments.

The present invention provides an apparatus for assembling or fabricating a reconstitution assembly. According to one embodiment of the invention shown in FIG. 1, the reconstitution assembly is generally designated with the reference numeral 1. The reconstitution assembly 1 generally includes a reconstitution device 10, a first container 12, and a second container 14. In other embodiments, it may be desired to only attach a single container to a reconstitution device to form a reconstitution assembly. For example, an alternate reconstitution assembly 1 may comprise the reconstitution device 10 attached only to the first container 12. Another alternate reconstitution assembly may comprise the reconstitution device 10 attached only to the second container 14.

The reconstitution device 10 provides a connector device that is used to mix two substances within the first and second containers 12,14. More particularly, the reconstitution device 10 reconstitutes a drug with a diluent. To accomplish the reconstitution of the drug, the device 10 is attached to the first container 12, commonly a flexible bag or a syringe, containing a diluent, and is attached to the second container 14, commonly a vial containing a drug, such as a pharmaceutical agent or cosmetic agent to be reconstituted. The device 10 provides fluid communication between the two containers through a hermetically sealed piercing member so that the drug may be reconstituted, and delivered to a patient. What is meant by hermetically sealed is that the portions of the piercing member that contact the fluid and that pierce the closures of the two containers 12,14 are sealed from the outside environment.

While the diluent will be a liquid, the beneficial agent may be either a powder or a lyophilized drug to be dissolved or a liquid drug to be reduced in concentration. The device 10 provides the benefit of allowing medical personnel to selectively attach a vial of their choice to the device 10. Thus, hospitals and pharmacies do not have to stock pre-packaged drug vial and connector assemblies. Further, the device 10 of the present invention allows for docking a vial 14 to the connector 10 without breaching the hermetic seal of a piercing member associated with the connector 10 and without piercing the closure of the vial 14. Thus, the vial 14 may be pre-docked to the device 10 of the present invention for essentially the full period the drug is active. Further, the device 10 can be activated by applying a force directly to the connector 10 without necessarily contacting sidewalls of the first and second containers 12,14.

Referring to FIGS. 1, 2 and 2A, the first container 12 is typically a flexible bag or flexible diluent container, and is used to contain solutions for a patient to be received intravenously. Flexible containers are typically constructed from two sheets of a polymeric material forming sidewalls that are attached at their outer periphery to define a fluid tight chamber therebetween. The flexible containers can be made from a variety of materials. At one point on the periphery of the container 12, a tubular port 16 is inserted between the sidewalls to provide access to the fluid chamber. The tubular port 16 could be considered to include a port adapter assembly 30 having a flange. A second port 18 is shown for allowing access by a fluid administration set to deliver the reconstituted drug to a patient. However, the first container 12 can be any type of container, including, for example, a syringe barrel, suitable for containing a liquid to be used to reconstitute a drug.

As further shown in FIGS. 1, 2 and 2A, the second container 14, which contains a drug to be reconstituted, is a vial. The vial 14 is typically a glass or plastic container with a closure member. The closure member may include a rubber stopper 20 and may also have a crimp ring 22. The rubber stopper 20 is inserted in an opening of the vial 14. The rubber stopper 20 is held in place by the crimp ring 22 (FIG. 2A), typically made of soft metal such as aluminum, that is crimped around the stopper 20 and the neck of the vial 14 to fixedly attach the stopper 20 to the vial 14. The crimp ring 22 has an aperture to define a target site on the rubber stopper 20. The device 10 can preferably be adapted to accept vials of any size, particularly 20 mm and 13 mm vials. Additionally, the second container 14 can be any container that is adapted to accommodate drugs that require reconstitution.

The connector 10, as stated above, is configured to connect to both the flexible bag 12 and the vial 14 and place the contents of the flexible bag 12 and the vial 14 into fluid communication with one another. As further shown in FIGS. 1, 2 and 2A, the connector 10 generally comprises a sleeve assembly 24, a piercing assembly 26, a gripper assembly 28 and a sleeve connector port 17. The sleeve assembly 24 generally has a first sleeve 32 and a second sleeve 34. In one preferred form of the invention, the second sleeve 34 is integral with the gripper assembly 28. The gripper assembly 28 and one portion of the sleeve assembly 24 (e.g., the second sleeve 34), are collectively configured for axial movement with respect to another portion of the sleeve assembly 24 from an inactivated position to an activated position. What is meant by the inactivated position is that the containers 12,14 are not in fluid communication with each other wherein the connector 10 has not been activated. What is meant by the activated position is that the containers 12,14 are placed in fluid communication with each other wherein the piercing assembly pierces the closures of the first and second containers 12,14. What is meant by the deactivated position, or post reconstitution position, is the first container 12 and the second container 14 are not in fluid communication and have been moved from the activated position to the deactivated position. The structure and operation of the reconstitution device 10 is further described in U.S. patent application Ser. No. 10/746,238, filed concurrently herewith, which is incorporated herein by reference and made a part hereof. It is understood that the assembly and fabricating apparatus of the present invention can be used with a variety of different reconstitution devices and containers as desired.

The apparatus that assembles the reconstitution assembly 1 will now be described.

Structure/Apparatus

Figure 64:
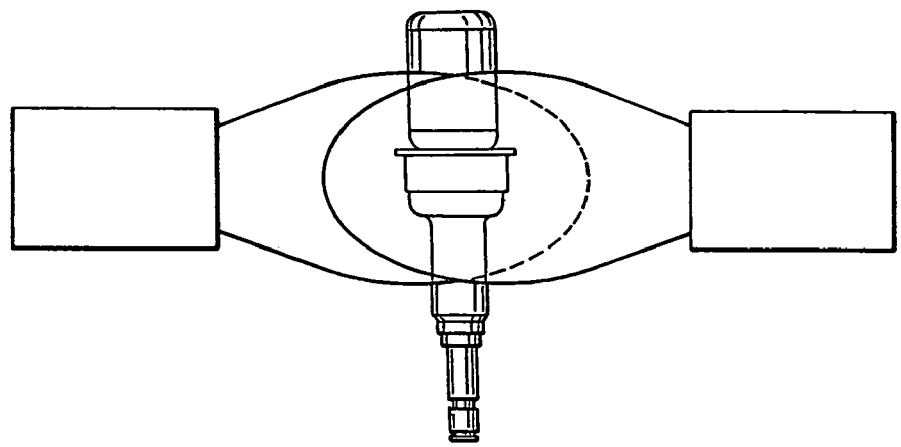
FIG. 64 is a schematic side view of sterilizing fields according to another embodiment of the present invention.

FIGS. 3-64 generally disclose a reconstitution assembly apparatus or connection system, generally referred to with the reference numeral 21, that fabricates the reconstitution assembly 1 shown in FIG. 1. As shown in FIG. 3, the reconstitution assembly apparatus 21 is a multi-station assembly and generally includes a first section, or first cell 23, generally referred to as a vial/device connection system 23, and a second section, or second cell 25, generally referred to as a bag/device subassembly connection system 25.

The apparatus 21 is generally designed to provide two connections, preferably in a sterile manner. One connection is between the first container 12 and the reconstitution device 10, and one connection is between the second container 14 and the reconstitution device 10. However, in other embodiments, only one sterile connection may be desired. In those instances, one section of the system may be removed or not utilized, leaving only the first cell 23 or second cell 25. The entire reconstitution assembly apparatus 21, including both cells 23, 25, will now be described with the understanding that parts of the system could be modified or removed without departing from the spirit of the invention as set forth in the appended claims.

First Cell: Vial/Device Connection System 23

The first cell 23 of the apparatus 21 generally serves to sterilely connect the second container 14 to the reconstitution device 10. The connection of the second container 14 to the reconstitution device 10 is preferably an automated process wherein the reconstitution device 10 and second container 14 are sterilely joined without the direct contact of human operators with the reconstitution device 10 or second container 14.

The first cell 23 generally comprises a positioning assembly 27, a vial pallet transport assembly 90, a device loader module 94, a container loader module 154, a vial holder placement module 260, a vial/device sterilization booth 270, a vial holder removal module 340, a depalletize device/vial module 350, and a shrinkband applicator 360. Each of these components is discussed in further detail below.

Positioning Assembly 27 (Vial Pallet)

Figure 4:
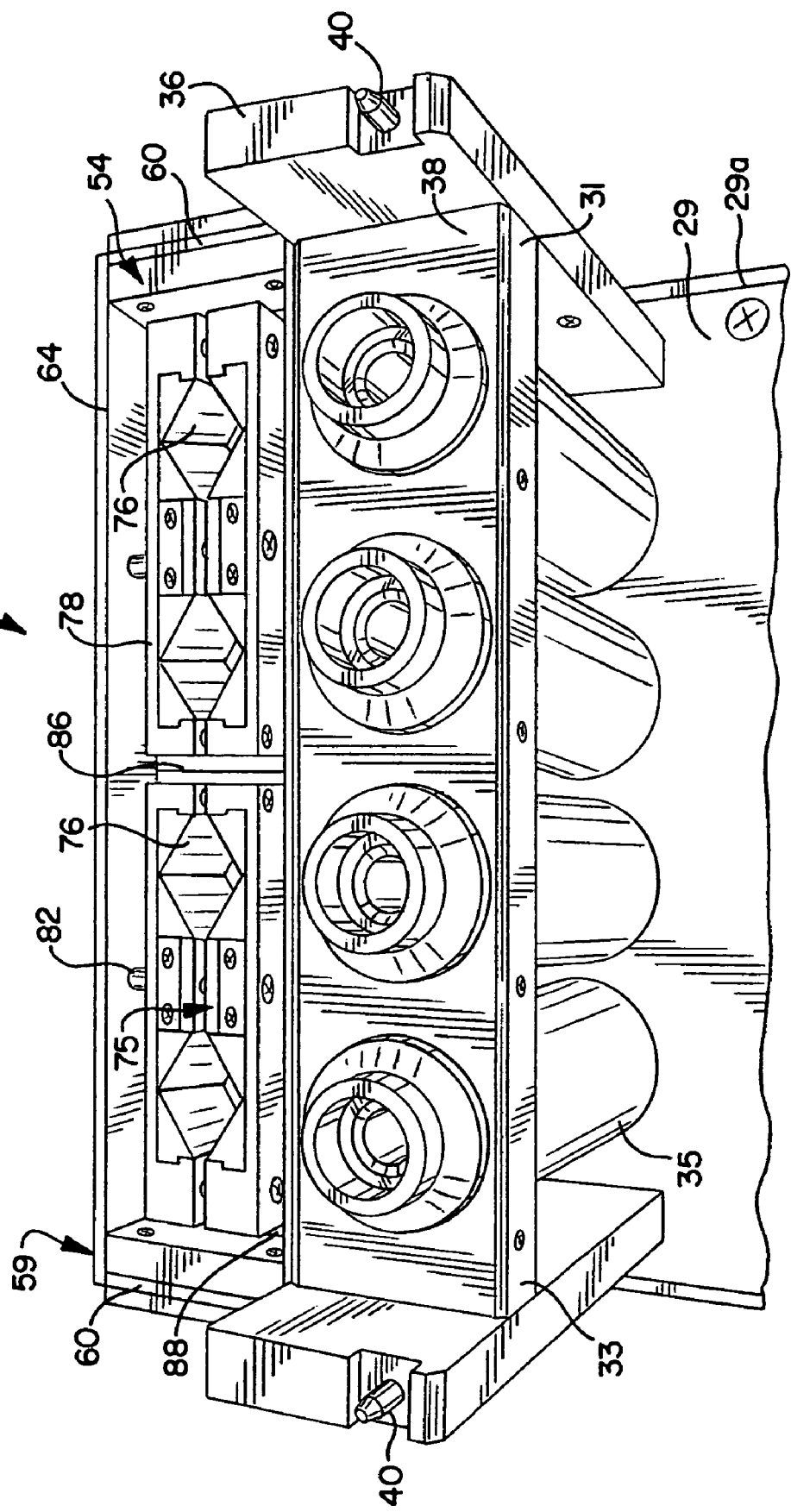
FIG. 4 is a front perspective view of a positioning assembly for use in a connecting system according to one embodiment of the present invention.

The positioning assembly in this instance is a vial pallet 27, and one preferred embodiment is shown in FIGS. 4-14. As described in greater detail below, the vial pallet 27 is conveyed by the transport assembly 90 (FIG. 3) to various locations in the first cell 23 and ultimately positions the vial 14 and the reconstitution device 10 such that they can be connected within a sterilizing field within the vial/device sterilization booth 270 (FIG. 3). The vial pallet 27 acts as a transportable platform for holding and positioning the reconstitution device 10 and vial 14 for sterile connection. As shown in FIG. 4, the vial pallet 27 generally includes a base 29, a reconstitution device holder 31, and a container holder 54, which is a vial holder in this embodiment.

Figure 6:
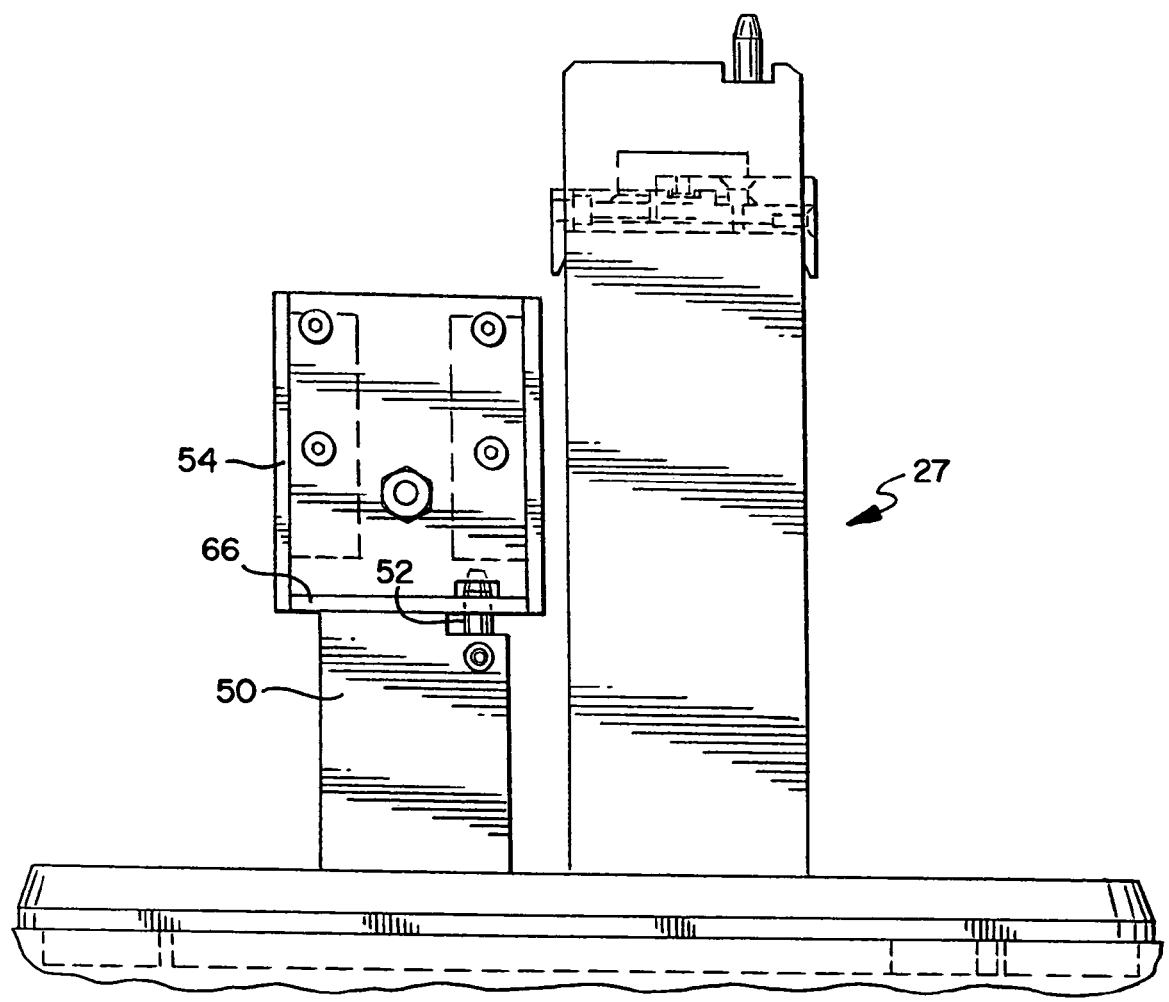
FIG. 6 is a side elevation view of the positioning assembly in an unstacked loading position according to one embodiment of the present invention.
Figure 7:
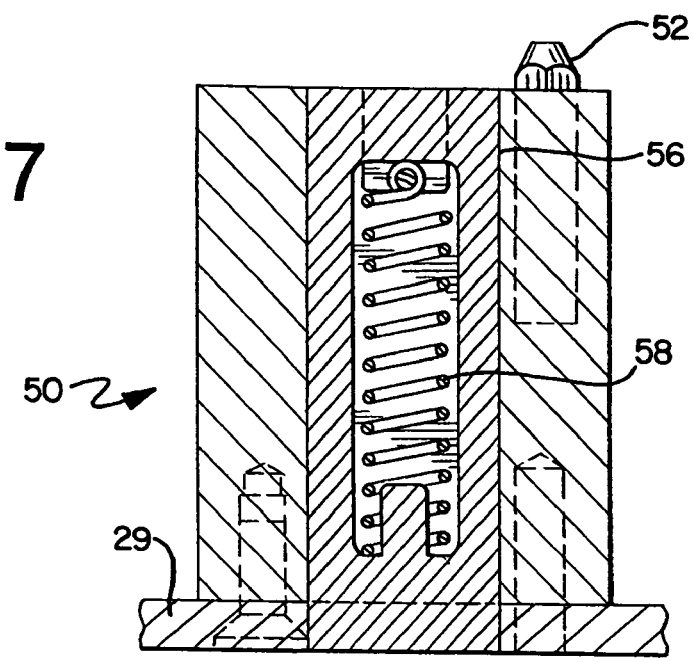
FIG. 7 is a partially cut away side elevation view of a container holder support of the positioning assembly according to one embodiment of the present invention.
Figure 8:
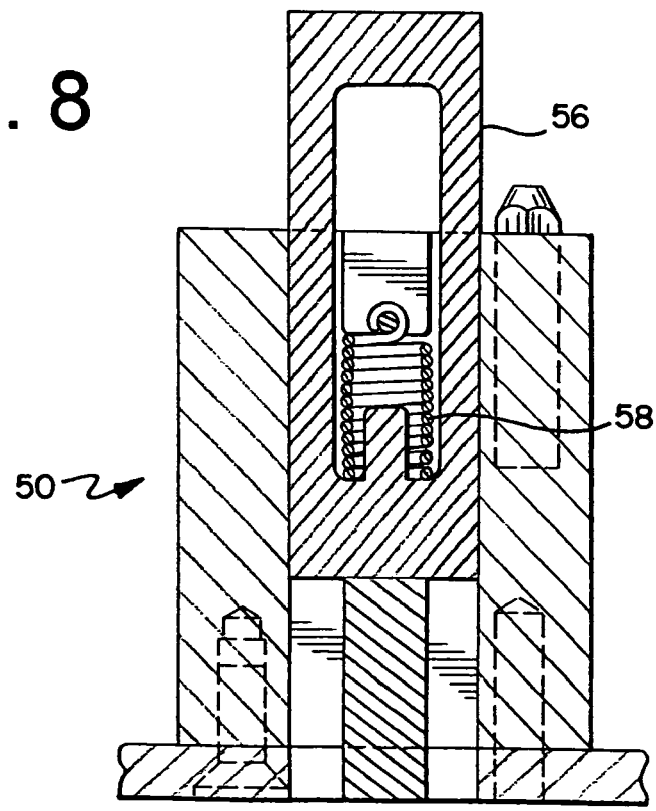
FIG. 8 is another partially cut away side elevation view of the container holder support of FIG. 7.

The base 29 generally includes a plate 29a having a flat top surface upon which the other component parts of the vial pallet 27 are supported. The base 29 generally includes container holder supports 50 as shown in FIG. 6. The container holder supports 50 are shown in detail in FIGS. 7 and 8. The container holder supports 50 are generally rectangular and preferably include positioning pins 52 on a top surface for receiving the vial holder 54. Preferably, the vial pallet 27 includes three container holder supports 50, which are equally spaced, and support the vial holder 54. The container holder supports 50 preferably include an internal slide 56. The slide 56 generally includes a spring 58. The spring 58 may become compressed when the slide 56 is raised as shown in FIG. 8. The spring 58 generally provides a biasing force to move the slide 56 back towards the pallet base 29 as shown in FIG. 7. The base 29 generally has an opening such that the slide 56 may be pushed upward through the opening in the base 29.

As shown in FIG. 4, the reconstitution device holder 31 generally includes a support frame 33 and a device holder subassembly 35. In a preferred embodiment, a plurality of device holder subassemblies 35 are included, generally four subassemblies 35. The support frame 33 generally includes top holder supports 36 and a guide block 38. The guide block 38 generally extends between the top holder supports 36, and is generally secured to the top holder supports 36 by screws or other securing means. The top holder supports 36 preferably extend vertically beyond the guide block 38 and terminate in an upper surface having locating pins 40. The guide block 38 generally provides a guide for positioning the device holder subassemblies 35, and has openings in which the device holder subassemblies 35 are positioned.

Figure 5:
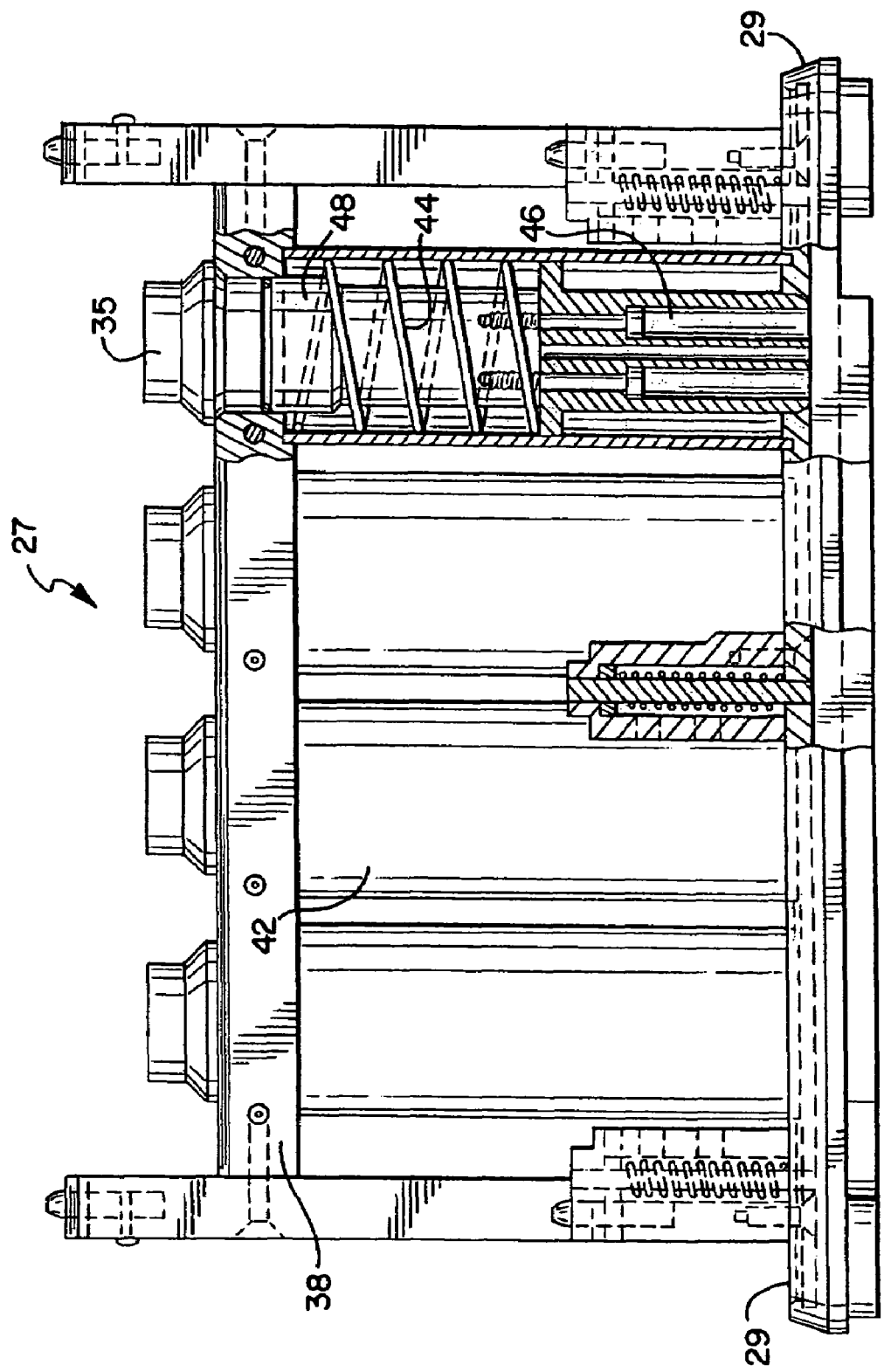
FIG. 5 is a front elevation view of the positioning assembly of FIG. 4, the assembly having a portion cut away.

FIG. 5 shows a cut-away view of the vial pallet 27, including the device holder subassemblies 35. Each of the device holder subassemblies 35 generally includes an external sleeve 42. The external sleeves 42 generally extend from the base 29 through the guide block 38, and protect the inner components of the device holder subassemblies 35. The external sleeves 42 are preferably hollow cylindrical columns. Inside each of the external sleeves 42 is generally a spring 44. The external sleeves 42 are generally secured to the base by spring retainers 46. The spring retainers 46 preferably extend through the base 29, into the external sleeves 42 and secure one end of each spring 44. The other end of each spring 44 is generally secured to a device nest 48. The device nest 48 is positioned in the external sleeve 42. The device nests 48 are generally biased in the direction of the base 29 by the springs 44. The device nests 48 preferably have a shape complementary to the shape of an exterior surface of the reconstitution device 10, allowing the reconstitution device 12 to securely rest within the device nests 48.

Figure 9:
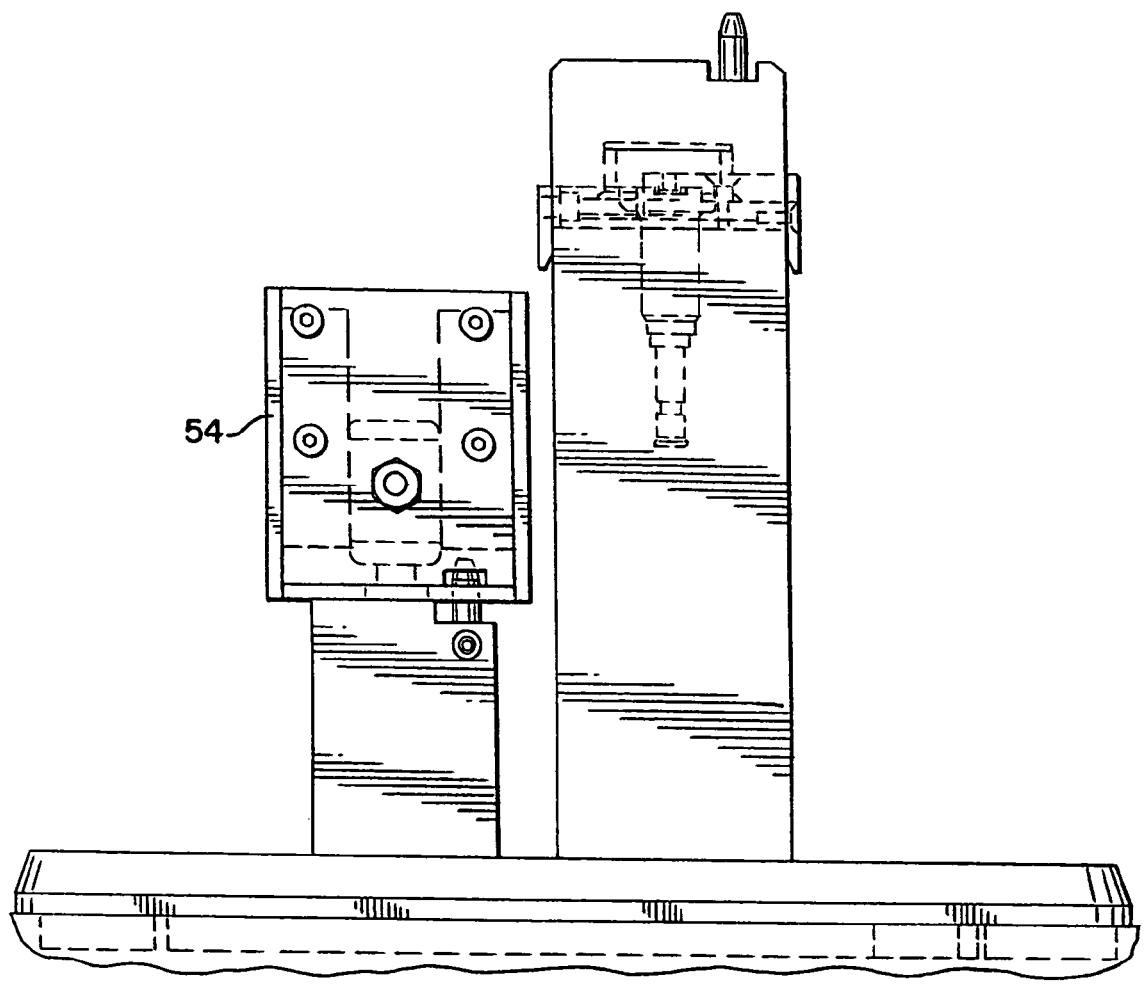
FIG. 9 is a side elevation view of the positioning assembly having a reconstitution device and drug vial loaded therein, the positioning assembly shown in an unstacked loading position according to one embodiment of the present invention.
Figure 10:
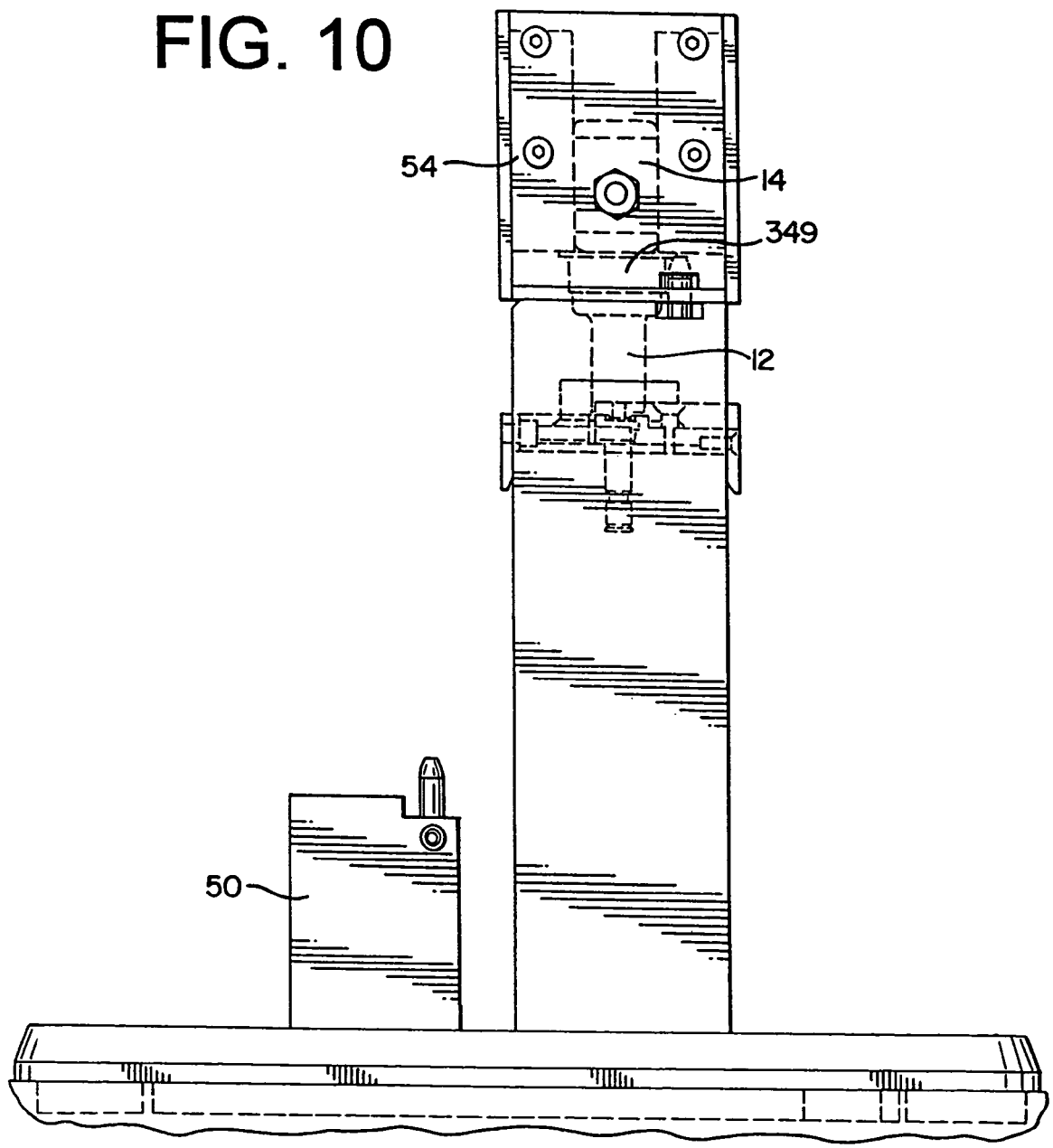
FIG. 10 is a side elevation view of the positioning assembly of FIG. 9, the positioning assembly shown in a stacked connecting position.

The container/vial holder 54 is generally a rectangular box having an open top. The vial holder 54 is preferably configured to hold four vials 14. As shown in FIG. 4, it preferably includes a housing 59 and a vial clamping mechanism 75. The vial holder 54 may generally be placed onto the vial pallet 27 in an unstacked loading position as shown in FIGS. 6 and 9, or in a stacked connecting position as shown in FIG. 10. When the vial holder 54 is loaded and in the connecting position, the reconstitution devices 10 and vials 14 are preferably coaxially positioned.

Figure 11:
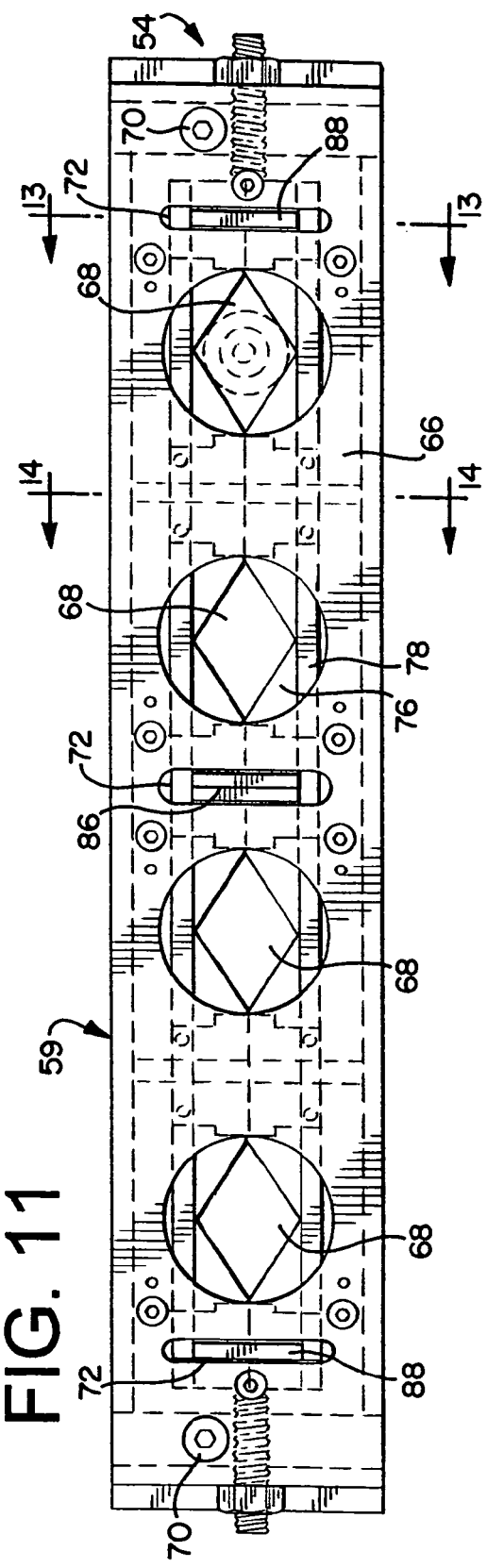
FIG. 11 is a bottom view of the container holder support of the positioning assembly.
Figure 12:
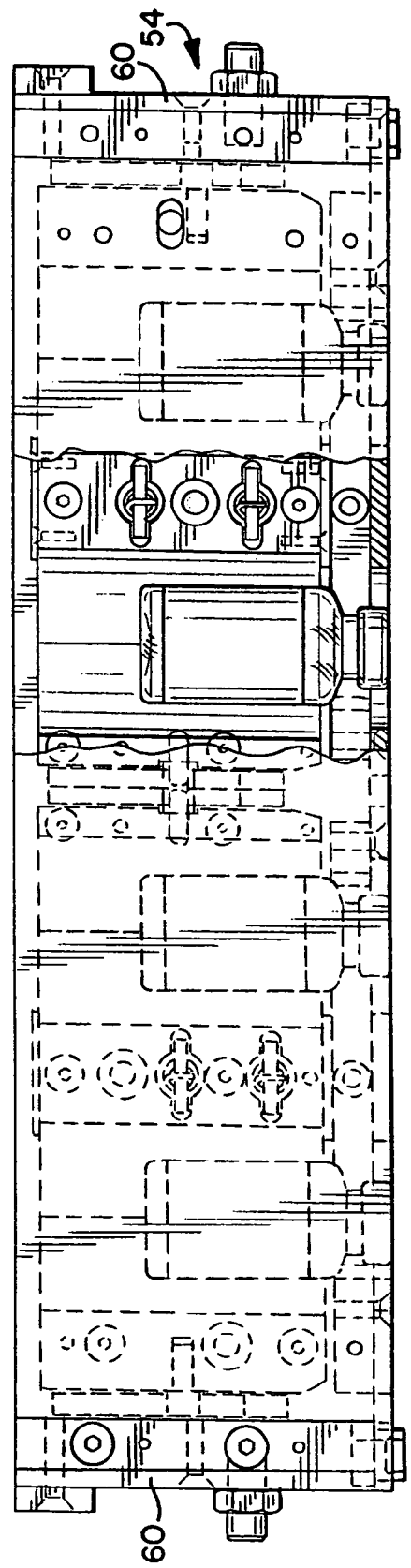
FIG. 12 is a partially cut away front elevation view of the container holder support of the positioning assembly.

As shown in FIGS. 4 and 11, the housing 59 of the vial holder 54 generally includes end plates 60. The end plates 60 are generally secured to first and second side plates 64. A bottom plate 66, as shown in FIG. 11, is secured to the end plates 60 and side plates 64 to form a rectangular box having one open side at its top. As further shown in FIG. 11, the bottom plate 66 generally includes four device openings 68. The bottom of the vial holder 54 further includes pin holes 70 for receiving the positioning pins 40 of the reconstitution device holder 31 (FIG. 4) or the positioning pins 52 of the container holder supports 50 (FIG. 6). Additional access slots 72 are preferably also formed in the bottom plate 66. Each of the end; side and bottom plates is generally formed of metal, such as steel or lead, and has sufficient thickness to give the vial holder 54 strength and to act as a radiation shield for the vial 14 when it is positioned in the vial holder 54.

In use, vials 14 positioned within the housing 59 of the vial holder 54 are preferably shielded from undesired exposure to radiation, or other sterilizing effects, used to sterilize the connection formed between the vials 14 and reconstitution devices 10. It is preferable to shield the vials 14 from unwanted exposure to sterilizing effects in order to preserve the efficacy of drugs typically stored within the vials 14. In the preferred embodiment, the housing 59 of the vial holder 54 minimizes the exposure of the vials 14 to radiation from a low energy e-beam.

As further shown in FIG. 4, the vial clamping mechanism 75 of the vial holder 54 is configured to hold up to four vials 14. The vial clamping mechanism 75 generally includes clamp pads 76 which are secured to clamp plates 78. The clamp plates 78 are biased towards one another by springs 80, as shown in FIG. 14, such that the clamp pads 76 may secure a vial 14. Dowels 82 run through the clamp plates 78 between the side plates 64 of the vial holder 54. As shown in FIG. 13, pins 87 extend from the ends of each of the clamp plates 78.

As shown in FIG. 4, the clamp pads 76 generally include v-shaped cutouts such that when two of the clamp pads 76 are pushed together in the vial holder 54, they generally form a diamond shape. Generally, there are two v-shaped cuts formed in each clamp pad 76, so that two vials 14 may be secured when the corresponding clamp pads 76 are pushed together. The vial holder 54 preferably holds four vials 14 at a time, requiring a total of four clamp pads 76. The clamp pads 76 are preferably an extruded polyurethane material.

As further shown in FIGS. 11-14, the vial clamping mechanism 75 further includes inner spreader plates 86 and outer spreader plates 88. The spreader plates 86,88 include channels 89 which receive the pin 87 (FIG. 13) from the clamp plates 78. The spreader plates 86, 88 are operably connected to the clamp plates 78 such that vertical movement of the spreader plates 86,88 translates into lateral movement of the clamp plates 78 and attached clamp pads 76. The channel 89 is angled such that when the spreader plates 86,88 are moved upward relative to the pin 87, which is fixed in the clamp plate 78, the clamp plates 78 move outward and open the vial holder 54 as shown in FIG. 13. The vial holder 54 may generally be opened either by pushing up on the spreader plates 86, 88, or by directly pulling the clamp plates 78 apart. The access slots 72 on the bottom plate 66 allow the spreader plates 86, 88 to be pushed upward from the bottom of the vial holder 54, opening the vial holder 54. As further shown in FIGS. 4 and 14, it is understood that the vial clamping mechanism 75 can hold the vial 14 in varying linear positions within the vial holder 54. Thus, the vial 14 can be placed in the vial holder 54 and held in place by the vial clamping mechanism 75 at differing vertical locations along the clamp pads 76 as desired.

As will be described in greater detail below, the vial pallet 27 receives and supports a plurality of reconstitution devices 10 and vials 14. In a preferred embodiment, the reconstitution device holder 31 holds four reconstitution devices 10, and the container holder 54 holds four vials 14. The container holder 54 is moveable on the vial pallet 27 from a first position, or unstacked position, to a second position, or stacked position wherein the vials 14 are positioned to be connected to the reconstitution devices 10. In the stacked position the coaxially arranged reconstitution devices 10 and vials 14 are easily connected by creating relative movement between the vials 14 and devices 10 and in one embodiment, by pushing on the devices 10 until the vials 14 snap into place in the gripper assemblies 28 of the reconstitution devices 10.

The vial pallet 27 may also be equipped with a dosimeter assembly for the purpose of sterility verification. The dosimeter assembly is positioned on the vial pallet 27 and allows for routine monitoring of dose in the sterile connection between the reconstitution device 10 and vial 14. The dosimeter assembly provides feedback to assure that a sterile connection has been achieved as will be described in greater detail below. The dosimeter assembly is also described in greater detail in commonly-owned U.S. application Ser. No. 10/745,466, entitled "Method And Apparatus For Validation Of Sterilization Process," filed concurrently herewith, which application is incorporated by reference and made a part hereof.

Vial Pallet Transport Assembly 90 (Vial Pallet Conveyor)

FIG. 3 shows an overview of the entire reconstitution assembly apparatus 21 including a vial pallet transport assembly 90, upon which the vial pallet 27 is supported and conveyed. The vial pallet transport assembly 90 generally includes a powered conveyor 92 for transporting and positioning the vial pallet 27 to different portions of the assembly apparatus 21. The powered conveyor 92 generally includes multiple sections of conveyor which may include belts and drive units. The preferred embodiment utilizes a power and free conveyor which is known in the relevant art.

In addition to a powered conveyor 92, the vial pallet transport assembly 90 may include additional components such as cross-transfers, lift and rotate units, lift and locate units, and lift gates positioned as necessary to position and transport the vial pallet 27 through the apparatus 21. The specific position of these components may be adjusted as necessary to move and position the vial pallet 27 as desired. The specific application of these components within a pallet transport assembly is understood by those of ordinary skill in the art. The vial pallet transport assembly 90 generally transports the vial pallet 27 between a device loading position, a vial loading position, a vial pallet stacking position, a first connecting position, a vial pallet unstacking position, and a vial and device subassembly transfer position. Each of these positions will be described in more detail below.

The vial pallet transport assembly 90 transports the vial pallet 27 between various modules and stations of the apparatus 21 that comprise the various positions mentioned above. Proximate to various pallet loading and unloading stations, and at various other queue positions along the powered conveyor 92, are soft-stop units for locating and positioning the vial pallets 27 as they proceed through the apparatus 21 along the vial pallet transport assembly 90. The position and specific function of each of these soft-stop units will be described in further detail when the use and operation of the apparatus 21 is described below.

Device Loader Module 94

The vial pallet 27 positioned on the vial pallet transport assembly 90 is preferably loaded with a reconstitution device 10 by the device loader module 94. The device loader module 94 generally handles a plurality of reconstitution devices 10 simultaneously, and in a preferred embodiment, loads four reconstitution devices 10 at a time onto the vial pallet 27. The preferred position of the device loader module 94 within the reconstitution assembly apparatus 21 is shown generally in FIG. 3. The device loader module 94 and its components are shown in greater detail in FIGS. 15-23.

Figure 18:
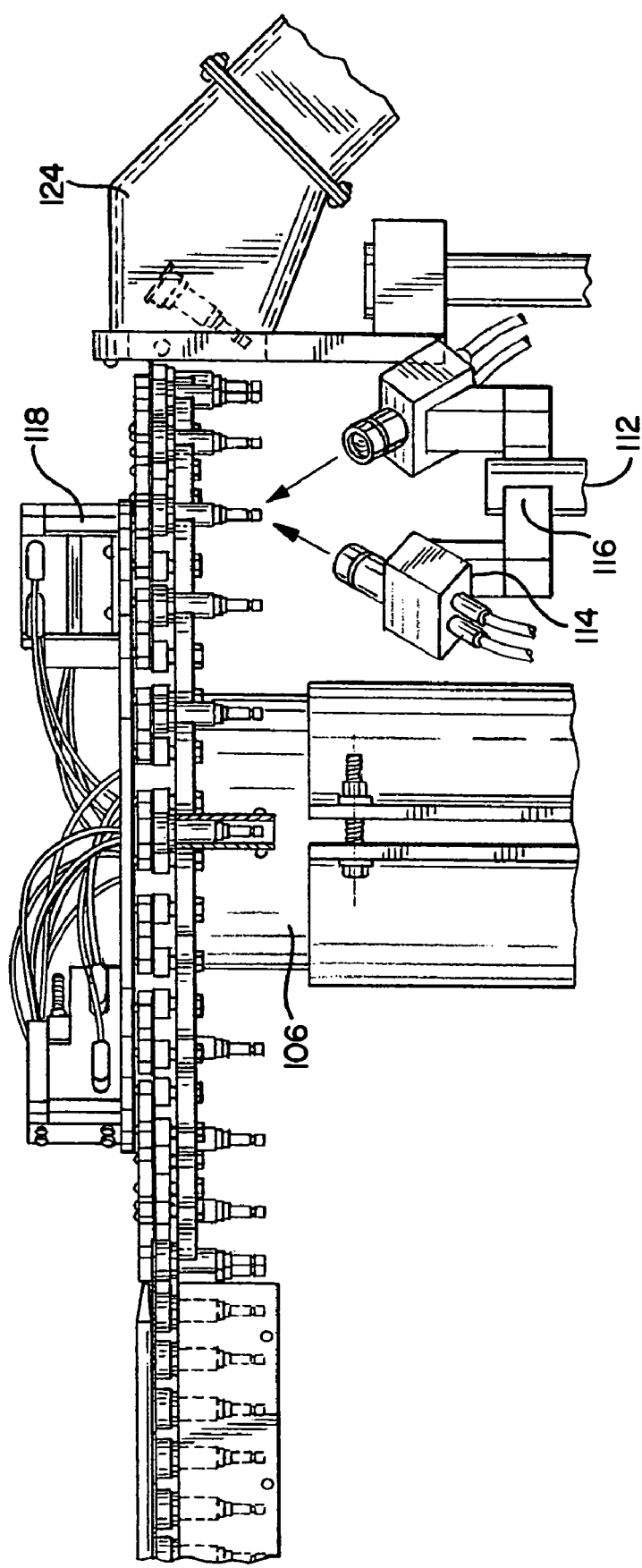
FIG. 18 is a side elevation view of the rotary dial-index table of FIG. 17 as viewed from lines 18-18 in FIG. 17.
Figure 19:
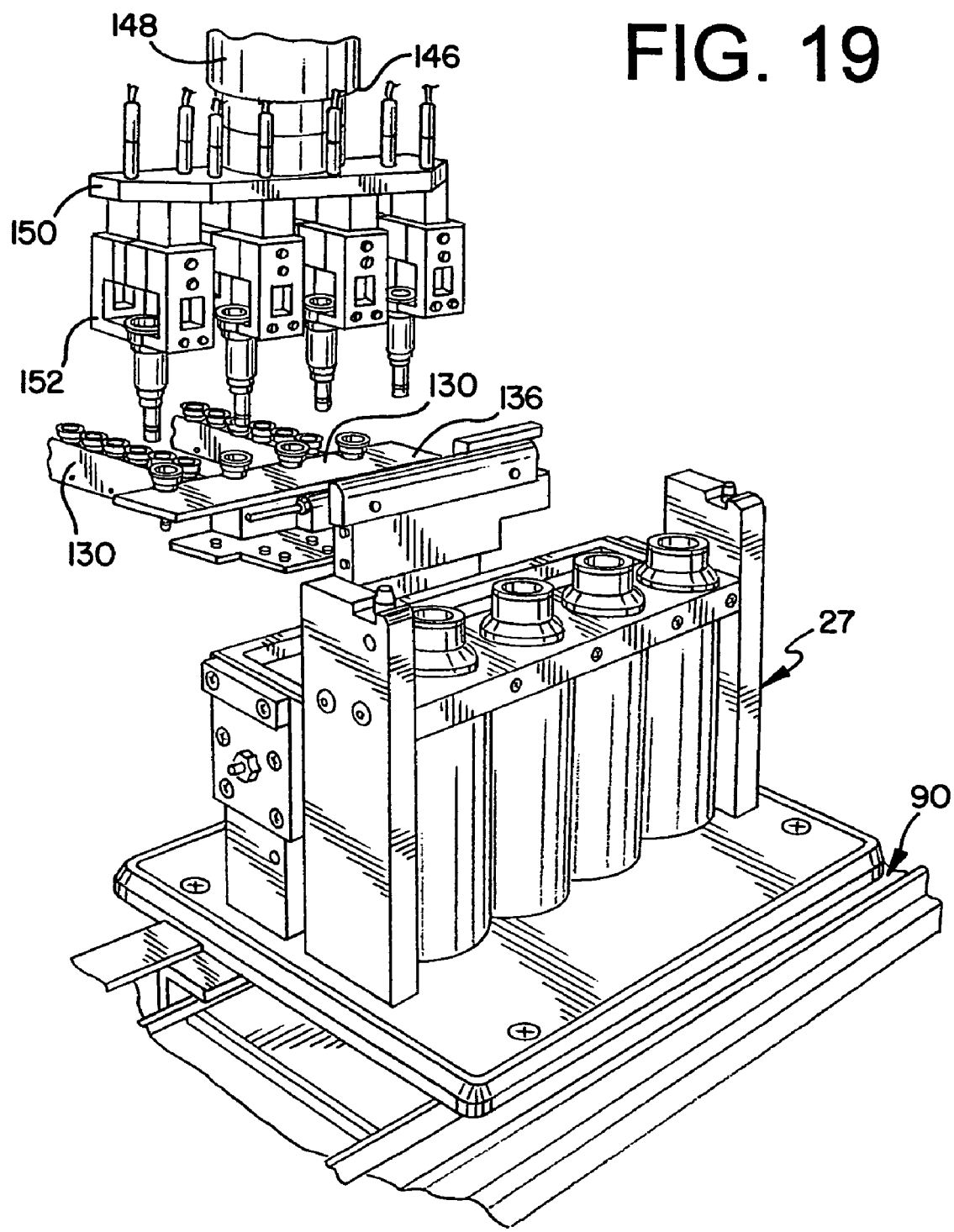
FIG. 19 is a partial perspective view of a reconstitution device transfer robot according to one embodiment of the present invention, shown transferring reconstitution devices onto the positioning assembly positioned on a conveyor.

The device loader module 94 generally includes a reconstitution device receiver 96 (FIGS. 15-16), a rotary dial-index table 104 (FIGS. 17-18), transport tracks 130 (FIG. 19), a device presentation nest 136 (FIG. 19) and a transport robot 146 (FIG. 19). Each of these components of the device loader module 94 are preferably mounted on one or more base tables to position the components at an elevation level proximate to that of the vial pallet transport assembly 90.

The reconstitution device receiver 96 is generally where reconstitution devices 10 are fed into the device loader module 94 for eventual delivery to the vial pallet 27. The reconstitution device receiver 96 is preferably a vibratory bowl feeder which generally includes a loading bin 98, a vibrating bowl 99, and a discharge chute 100. Attached to the vibrating bowl 99 is preferably a vibrating motor 102. The vibrating bowl 99 is configured to position each of the reconstitution devices fed into the loading bin 98 such that each can be fed to the discharge chute 100 in the same position. The reconstitution devices 10 are generally positioned in a vertical position by the receiver 96 wherein the gripper assembly 28 of the device 10 faces generally upwards. Once the vibrating bowl 99 delivers the devices, the discharge chute 100 generally supports the reconstitution devices 10 at the gripper assembly portion of the devices 10. The discharge chute 100 then preferably carries a continuous line of reconstitution devices 10 to the rotary dial-index table 104.

Figure 17:
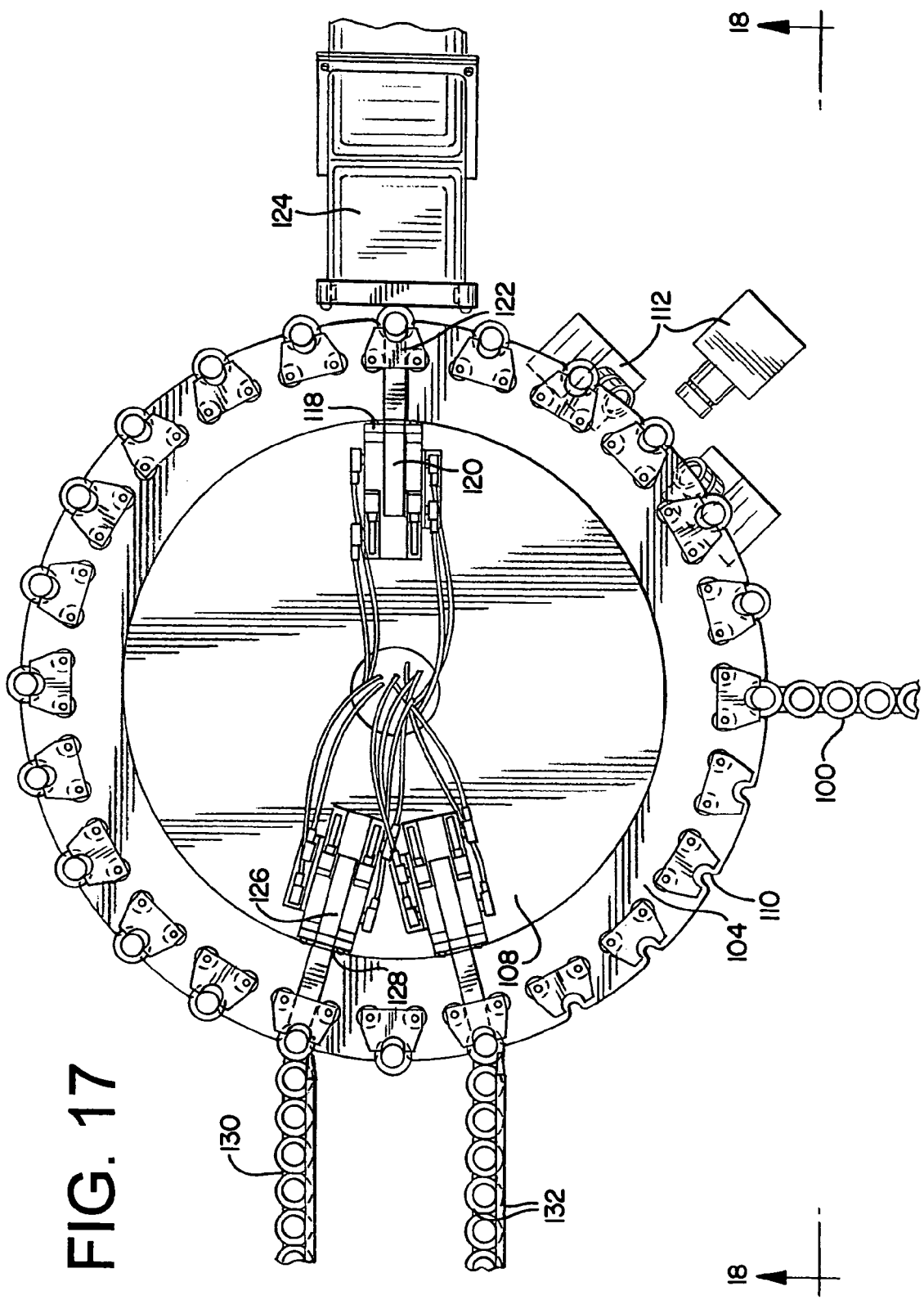
FIG. 17 is a top view of rotary dial-index table according to one embodiment of the present invention.

The rotary dial-index table 104 is shown in FIGS. 17 and 18. The table 104 generally includes a servo driver unit 106, device fixture nests 110, a reject inspection system 112 and a device off-load assembly 126. The servo driver unit 106 rotates a turntable 108 which supports the plurality of device fixture nests 110 at a radial periphery of the turntable 108. Reconstitution devices 10 are loaded into the device fixture nests 110 from the discharge chute 100.

The turntable 108 of the rotary dial-index table 104 preferably rotates in a counter-clockwise direction. The device fixture nests 110 receive reconstitution devices 10 from the discharge chute 100. As the turntable 108 rotates, the reconstitution devices 10 loaded into the device fixture nests 110 are preferably inspected by an inspection system 112. As further shown in FIGS. 17 and 18, the inspection system 112 generally includes a plurality of cameras 114 and lights 116. Cameras 114 are generally positioned both below and next to the rotary dial-index table 104. A reject shucker assembly 118 is preferably mounted to the rotary dial-index table 104. The reject shucker assembly 118 generally includes a pneumatic actuator 120 and device transfer tool 122. Rejected parts are shucked to a reject chute 124 which generally leads to a reject collection area. The device 10 may be rejected if it has not been properly preassembled to become part of the reconstitution assembly 1. For example, if a septum component has not been properly positioned in the device 10, the cameras 114 will detect this omission and indicate that the device 10 should be rejected.

The turntable 108 of the rotary dial-index table 104 continues to rotate in a counter-clockwise direction and places, in turn, each device fixture nest 110 next to the device off-load assembly 126. The device off-load assembly 126 generally includes one or more device shuckers 128, preferably two device shuckers 128. The two device shuckers 128 off load the reconstitution devices 10 to the transport tracks 130. In a preferred embodiment, there are two transport tracks 130 located proximate to the turntable 108.

The transport tracks 130 generally include two rails 132 upon which the reconstitution devices 10 are supported, generally at the gripper assembly portion of the device 10. The transport tracks 132 preferably further include a vibratory motor. As shown in FIG. 17, the devices 10 are moved along the transport tracks 130. The transport tracks 130 generally include anti-shingling features.

Figure 20:
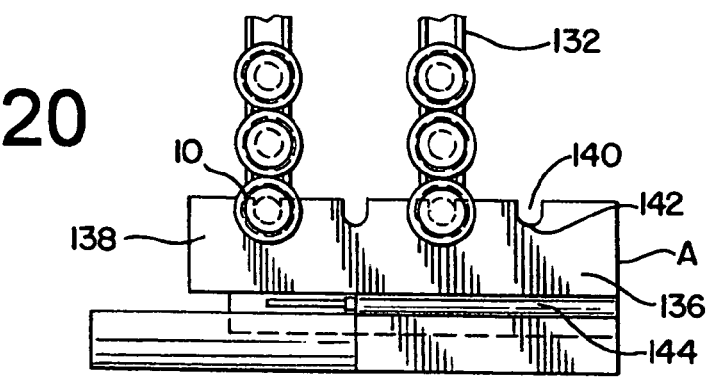
FIG. 20 is a top view of a reconstitution device presentation nest according to one embodiment of the present invention.
Figure 21:
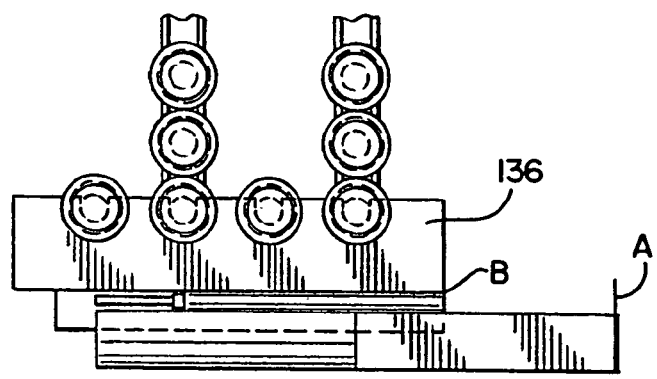
FIG. 21 is a top view of the presentation nest of FIG. 20, the nest shown in a second position.
Figure 22:
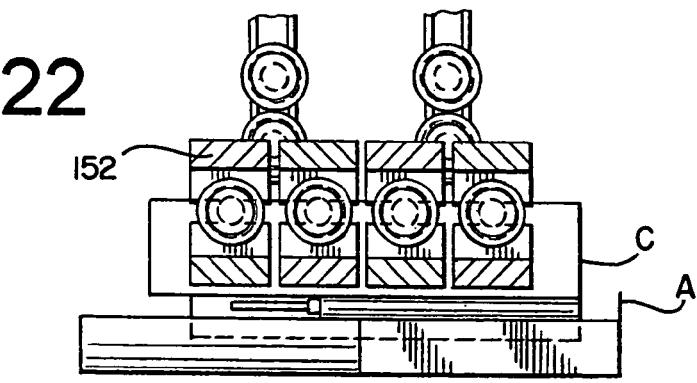
FIG. 22 is a top view of the presentation nest of FIG. 20, the nest shown in a third position.

As shown in FIG. 19, at the end of the transport tracks 130 opposite to the rotary dial-index table 104 is generally the device presentation nest 136. The device presentation nest 136 is movable to various positions to receive reconstitution devices 10 in preparation for the devices 10 to be loaded onto the vial pallet 27. The various positions are shown in FIGS. 20-22. The presentation nest 136 generally includes a base 138 with four individual device nests 140. The device nests 140 preferably include part present sensors 142. The base 138 is moved and controlled by an actuator 144. The actuator 144 is preferably a three position pneumatic actuator.

As further shown in FIG. 19, proximate to the presentation nest 136 is the transfer robot 146. The transfer robot 146 is of a type generally known in the art that is capable of grasping reconstitution devices 10 from the device presentation nest 136 and transferring the devices 10 to the vial pallet 27. The transfer robot 146 generally includes a robot arm 148 and a device picking tool 150. The device picking tool 150 generally includes part grippers 152.

Station guarding is preferably built around any potentially dangerous moving parts of the device loader module 94.

Container (Vial) Loader Module 154

After a reconstitution device 10 has been loaded onto the vial pallet 27, the vial pallet 27 is preferably conveyed by the vial pallet transfer assembly 90 to the container loader module 154. The container loader module 154 is shown generally in FIG. 3 and is located proximate the vial pallet transport assembly 90 and downstream of the device loader module 94. The container loader module 154 is also shown in FIGS. 24-33. The container loader module 154 preferably supplies and loads containers 14 to the vial pallet 27. As discussed, the containers 14 are preferably vials, and the container loader module 154 will alternatively be referred to as the vial loader module 154, although it can be appreciated that other types of containers could be used.

Figure 24:
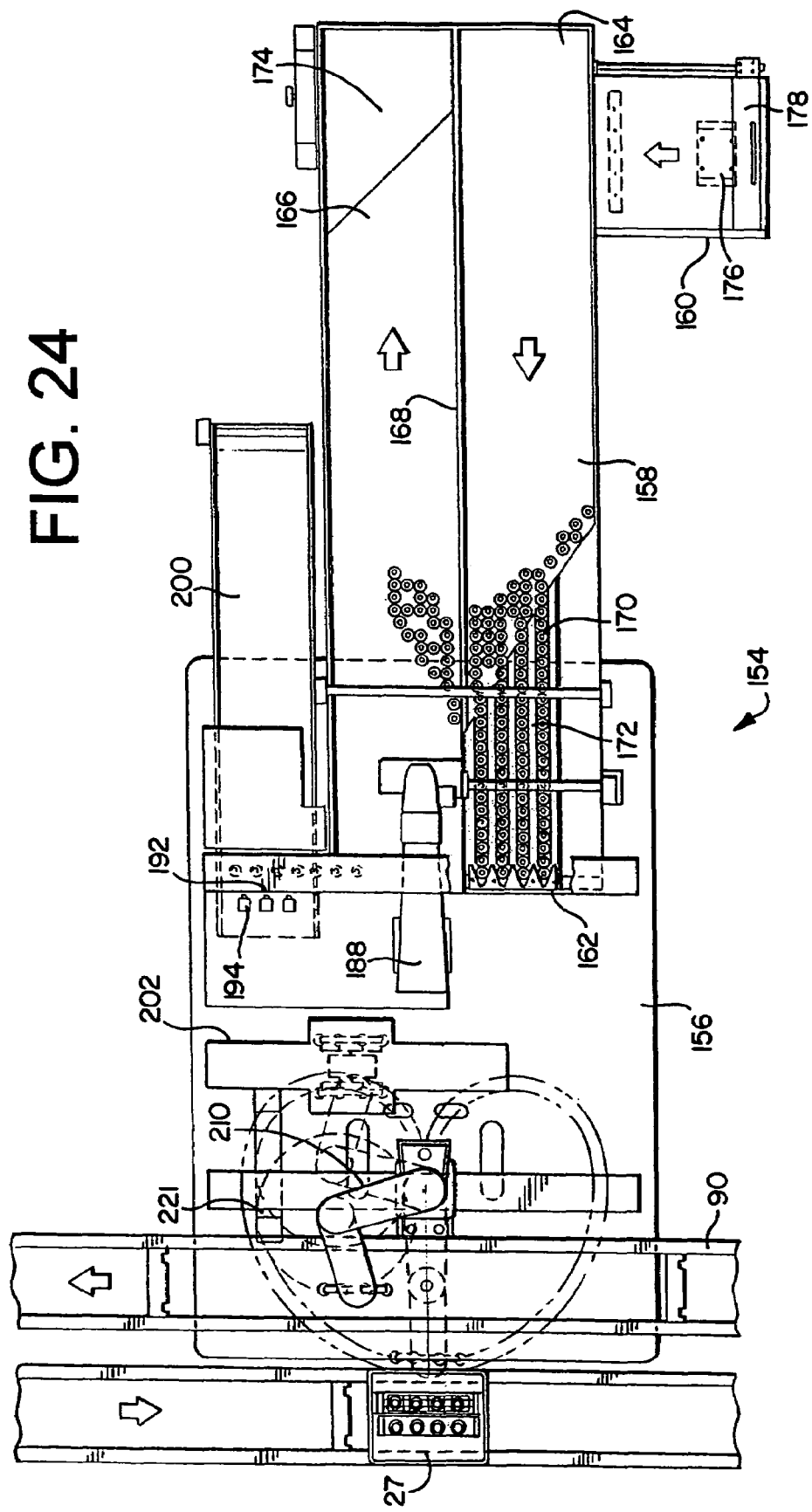
FIG. 24 is a plan view of a container loader module according to one embodiment of the present invention.

A first embodiment of the vial loader module 154 is shown in FIG. 24, and generally includes an accumulating conveyor 158, a container transfer robot 188, an inspection assembly 192, an uncap mechanism 202, a pallet load robot 210 and a vial holder opener 227.

The accumulating conveyor 158 is generally mounted on a station base table assembly 156. The accumulating conveyor 158 is preferably arranged to circulate vials 14 from a loading station 160 to a vial presentation fixture 162. The accumulating conveyor 158 generally includes a first accumulating conveyor 164 and a second accumulating conveyor 166 separated by a partition 168. Proximate to an end of the first conveyor 164 are located four separator lanes 170, each of which is sized to receive a vial 14. The entrances to the four separator lanes 170 are preferably offset from one another along an angle such that vials 14 in excess of the number required to fill the lanes 170 are conveyed to the second accumulating conveyor 166 through an opening in the partition 168. The four separator lanes 170 are generally formed by a plurality of spaced guide rails 172. The guide rails 172 are preferably adjustable to allow for different sized vials 14 which may be conveyed through the system 21. The second conveyor 166 includes an angled member 174 which conveys the vials 14 back to the first conveyor 164 through another opening in the partition 168. In this fashion, the vials 14 are circulated by the first and second accumulating conveyors 164,166.

Loading of the accumulating conveyor 158 is generally performed at the loading station 160. The loading station 160 preferably includes a container holding tray 176. Containers/vials 14 are generally placed onto the tray 176 in an upright fashion. A plow 178 generally pushes forward to introduce the vials 14 to the first accumulating conveyor 164.

Figure 25:
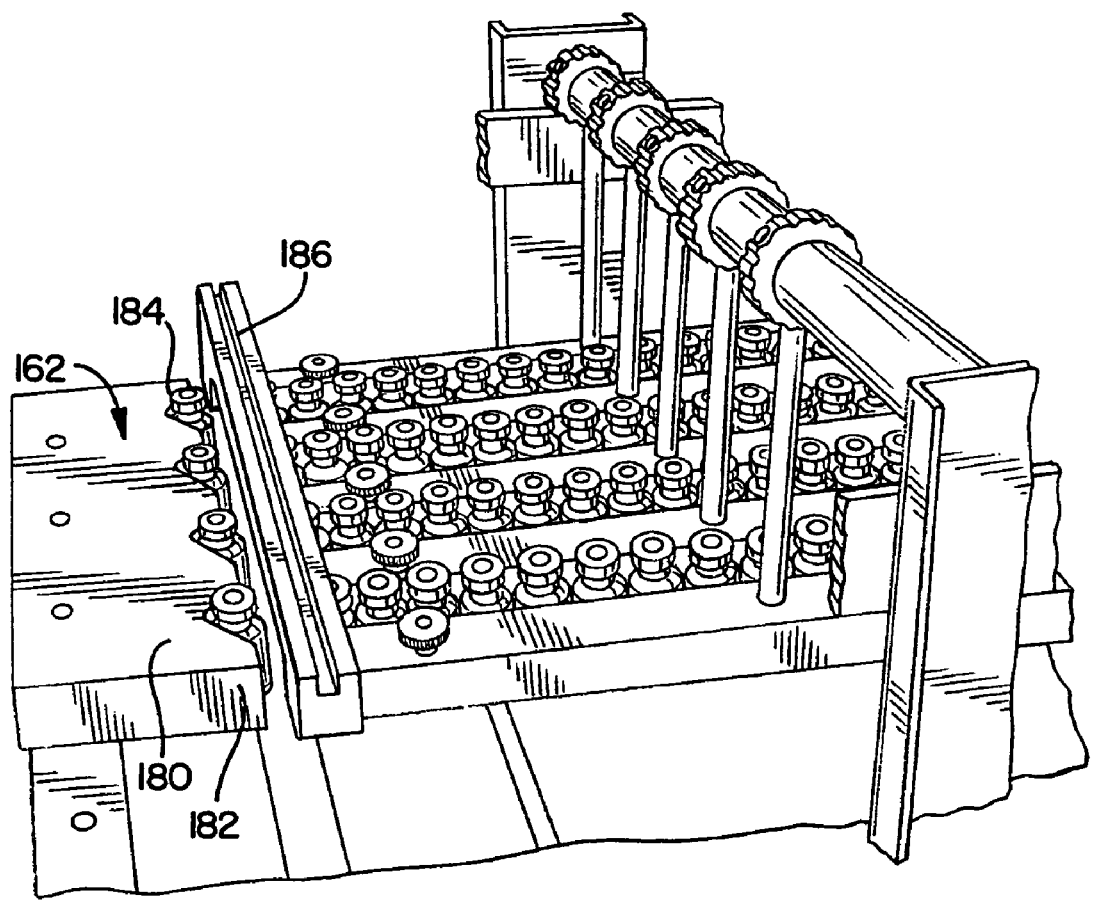
FIG. 25 is a perspective view of a portion of a container loader module according to one embodiment of the present invention.

The presentation fixture 162 is shown in more detail in FIG. 25. The presentation fixture 162 preferably includes a base 180 having extensions 182 which form v-shaped slots 184, and is generally termed a v-block fixture. The presentation fixture 162 preferably includes sensors 186 for container detection. The sensors are preferably ultra-sonic sensors. The accumulating conveyor 158 generally delivers vials 14 to the vial presentation fixture 162.

As shown in FIG. 24, the container transfer robot 188 is positioned proximate to the presentation fixture 162 for transferring the vials 14 from the vial presentation fixture 162 at the accumulating conveyor 158. The container transfer robot 188 is further shown in FIG. 26. The container transfer robot 188 generally includes a robot arm 190 and end of arm tooling 191 customized to pick the particular container being picked. Preferably, the tooling includes two gripping elements which close about a respective neck of the vials 14. The robot arm 190 raises the picked vials 14 and carries them to the inspection assembly 192. The vials 14 are generally positioned or moved by the container transfer robot 188 such that they may inspected by the inspection assembly 192 while being held by the container transfer robot 188.

As shown in FIG. 24, the inspection assembly 192 generally includes a camera 194, and more preferably a plurality of cameras 194 including three individual cameras 194. The inspection assembly 192 may also include mirrors used in conjunction with the cameras 194 to inspect the containers 14. The vials 14 are generally moved past the cameras 194 such that indicia contained on the container 14, such as a label, may be viewed by the cameras 194. The inspection assembly 192 preferably detects reject vials 14 which are damaged, or which have a damaged or incorrect label. Other embodiments of the inspection assembly may use other methods of detecting rejects such as bar code or radio frequency detection systems.

The inspection assembly 192 inspects the containers 14 and rejected containers are offloaded by the container transfer robot 188 onto a reject offload conveyor 200 for later operator attention. Vials 14 are generally inspected in batches of four vials 14. Acceptable vials 14 in a batch that contains a reject vial 14 are generally placed back onto the accumulating conveyor 158 by the container transfer robot 188 for recycling through the container loader module 154.

The container transfer robot 188 is also proximate to the uncap mechanism 202. Good batches containing no reject vials 14 are generally transported by the container transfer robot 188 to the uncap mechanism 202.

Figure 27:
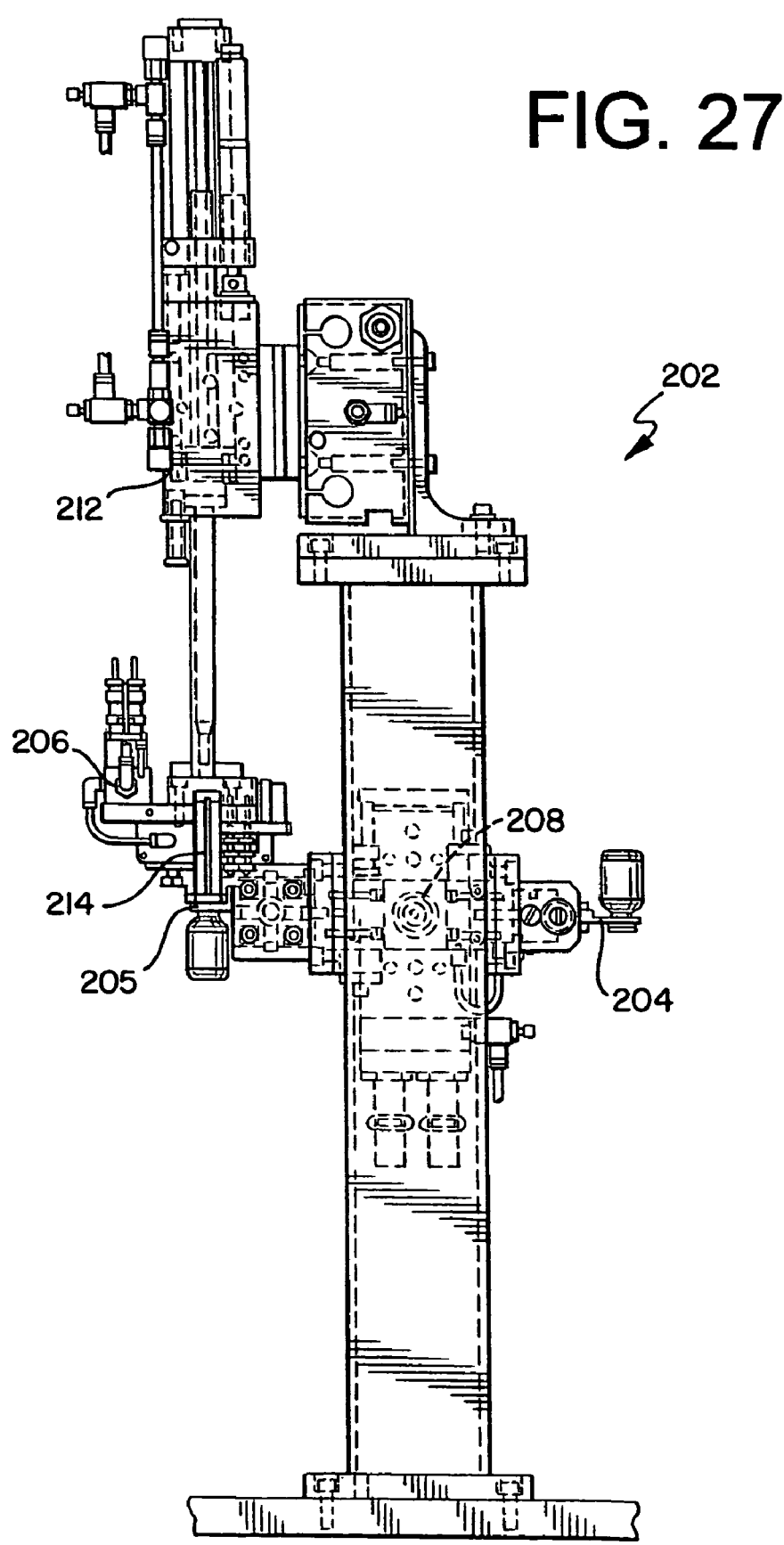
FIG. 27 is a side elevation view of an uncap mechanism assembly according to one embodiment of the present invention.

The uncap mechanism 202 is shown in greater detail in FIG. 27 and generally removes a cap that is typically part of a vial as shipped from, for example, a pharmaceutical company. The uncap mechanism 202 generally includes two container holders 204, 205 mounted on a rotary actuator 208 for inverting the vials 14 following removal of the cap from the vials 14. The uncap mechanism 202 also generally includes an opening mechanism 206.

Figure 26:
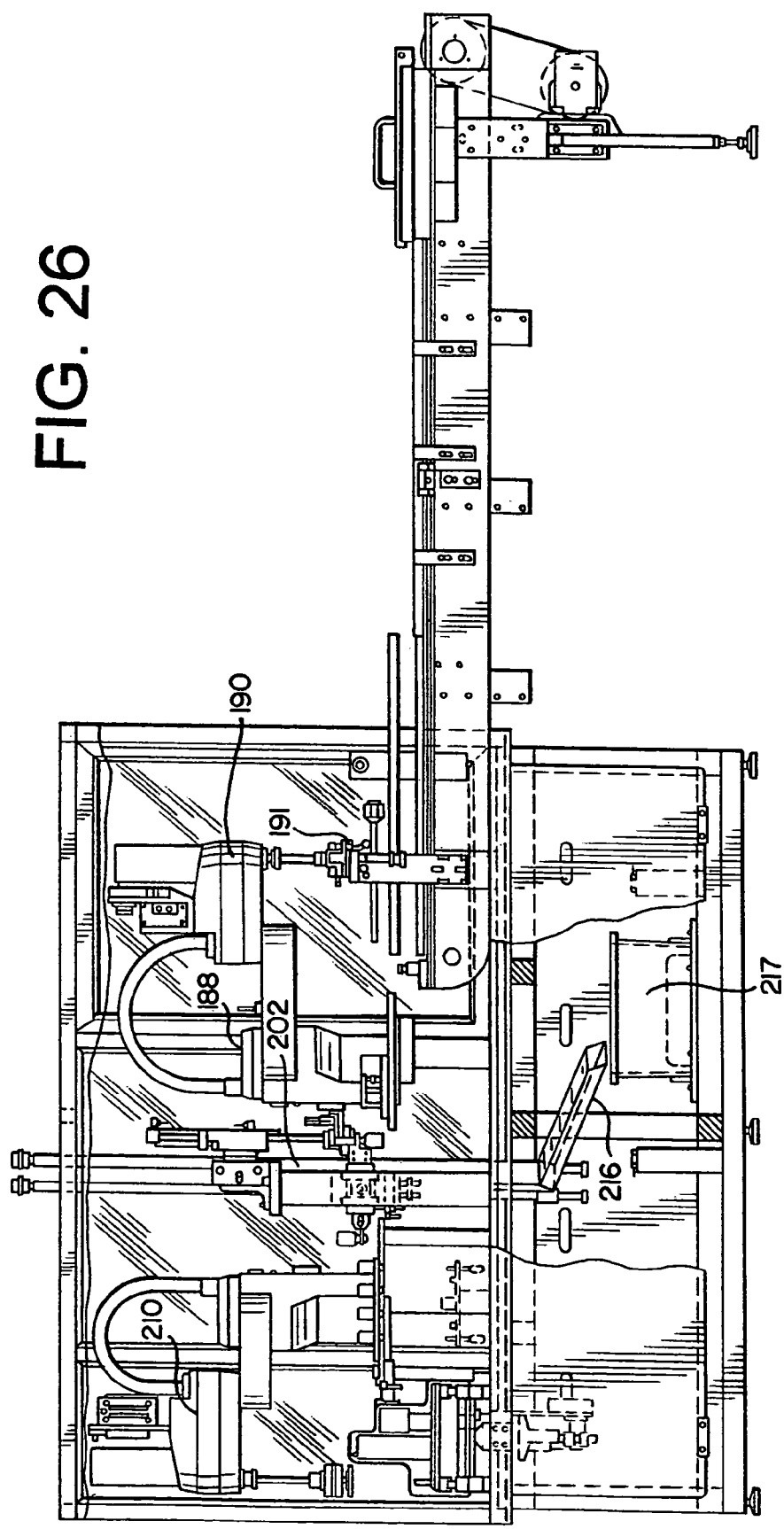
FIG. 26 is a side view of a portion of a container loader module according to one embodiment of the present invention.

The container holders 204, 205 preferably include tooling which generally grasps the neck of the vials 14 leaving the cap exposed. The cap is generally a soft metal crimp ring, such as aluminum, which crimped around the rubber stopper and neck of the vial 14. Each container holder 204, 205 generally includes tooling for gripping four vials 14 simultaneously. The container holders 204, 205 are preferably mounted opposite to one another on the rotary actuator 208 as shown in FIG. 27. The two container holders 204, 205 are positioned such that when the rotary actuator 208 is in a first operating position, vials 14 held in the first container holder 204 are proximate to and accessible by the opening mechanism 206, and at the same time vials 14 held in the second container holder 205 are proximate to and accessible by a pallet load robot 210 (FIG. 26).

The opening mechanism 206 generally includes an actuator 212 which lowers a gripper 214 to the capped vials 14. The gripper 214 generally includes fingers for gripping the cap. The gripper 214 removes the cap, or a portion of the cap, and places it into a disposal chute 216 which leads to a cap collection bin 217 (FIG. 26). The actuator 212 then preferably actuates and returns the gripper 214 to its original position. The actuator 212 is preferably a pneumatic actuator. It is understood that the cap may be in different forms and may be removable in different forms. For example, the vial 14 may have a cap that is removable to expose the crimp ring wherein the crimp ring has an opening to define a target site on the stopper of the vial 14.

After the caps have been removed from the vials 14, the rotary actuator 208 rotates. This rotation inverts the now uncapped vials 14 in the first container holder 204 and positions the vials 14 proximate to the pallet load robot 210. The rotation at the same time places the second container holder 205 proximate to the container transfer robot 188 for the loading of inspected, but still capped vials 14. The uncapped vials 14 positioned in the first container holder 204 in an inverted position are then transferred to the pallet load robot 210.

The pallet load robot 210 is shown and described in conjunction with FIGS. 28-31. The pallet load robot 210 generally moves vials 14 from the uncap mechanism assembly 202 into the vial pallet 27. The pallet load robot 210 generally includes a robotic arm 218, an end of arm tooling assembly 220, and may include a vacuum and blow-off assembly 221 (FIG. 24). The robotic arm 218 generally allows for moving the tooling assembly 220 between the container holder 204 holding uncapped vials 14 in an inverted position, and the vial holder 54 of the vial pallet 27 located on the vial pallet transport assembly 90. The pallet load robot 210 is preferably fixed to a station base table assembly on a pedestal.

Figure 31:
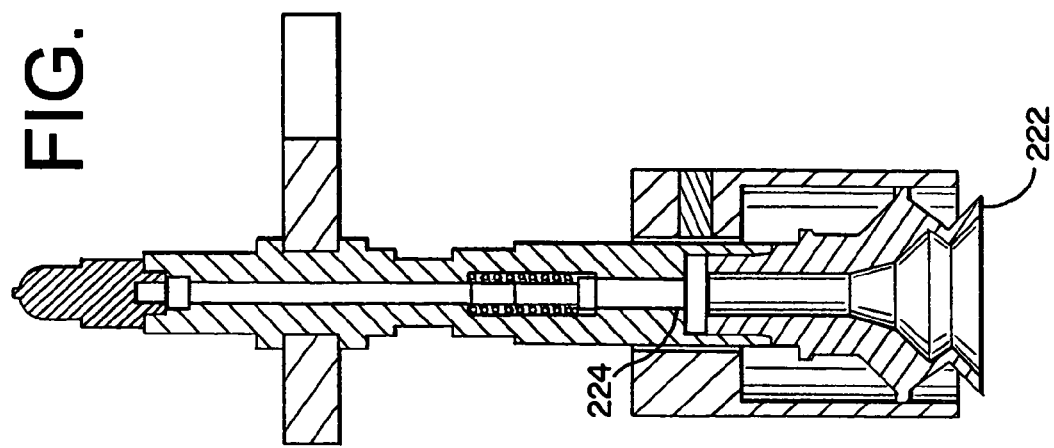
FIG. 31 is a cross-sectional view of a suction cup of the end of arm tooling of FIG. 30.
Figure 30:
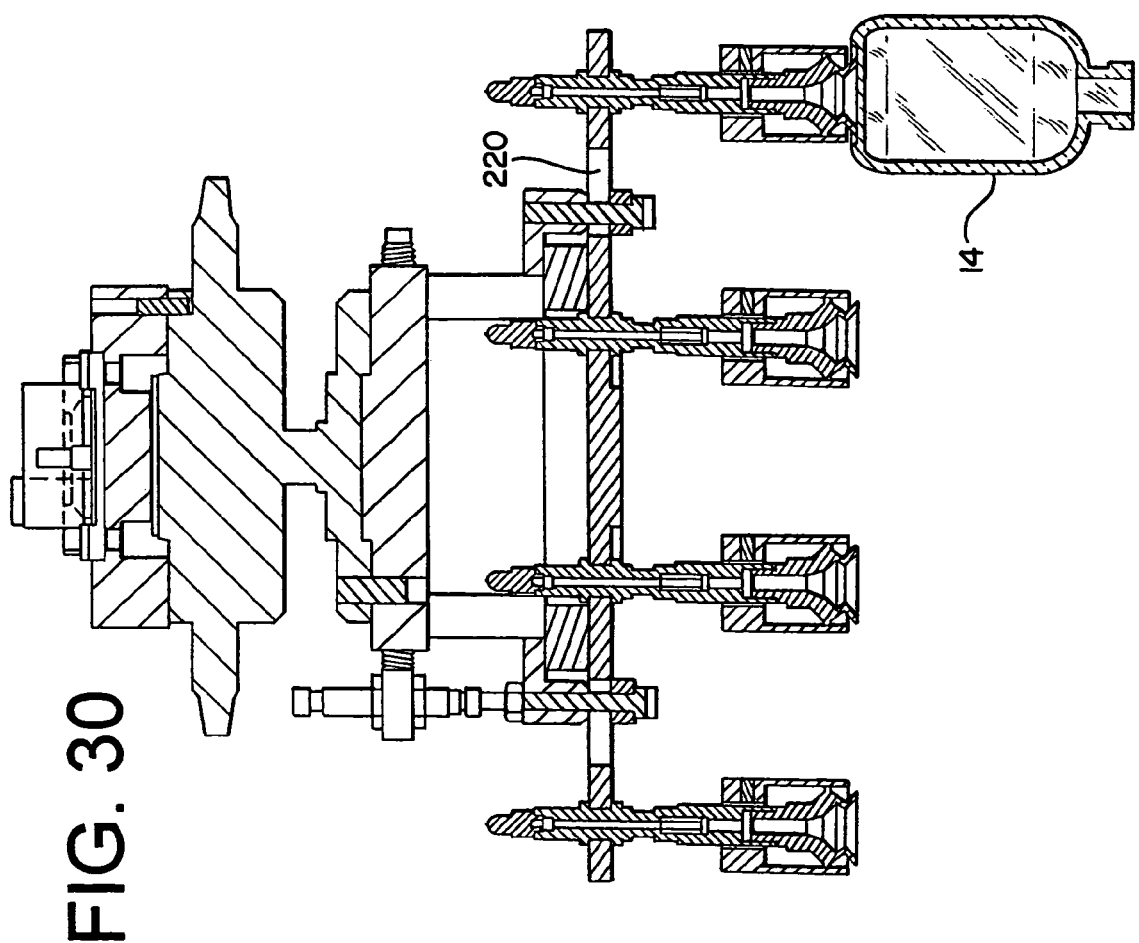
FIG. 30 is a cross-sectional view of an end of arm tooling for the pallet load robot of FIG. 29 according to one embodiment of the present invention.

As shown in FIGS. 30 and 31, the end of arm tooling assembly 220 generally includes suction cups 222, for securing the vials 14. A positive vacuum is applied through a line 224 in the suction cups 222. Preferably there are four suction cups 222 aligned in a row on the end of arm tooling assembly 220. The suction cups 222 are supported by the pallet load robot 210. The robot arm 218 positions the end of arm tooling 220, and an actuator 226 raises and lowers the suction cups 222 as needed. The suction cups 222 preferably form a tight seal with the bottom surface of the vials 14, and holds them securely while the end of arm tooling assembly 220 is moved. The end of arm tooling assembly 220 preferably can be easily changed out to accommodate vials 14 of different sizes.

As shown in FIG. 24, the vacuum and blow-off assembly 221 is generally positioned between the uncap mechanism 202 and the vial pallet transport assembly 90 on the station base table assembly 156. The vacuum and blow-off assembly 221 removes any contaminants or undesirable matter on the vials 14 after uncapping.

Figure 28:
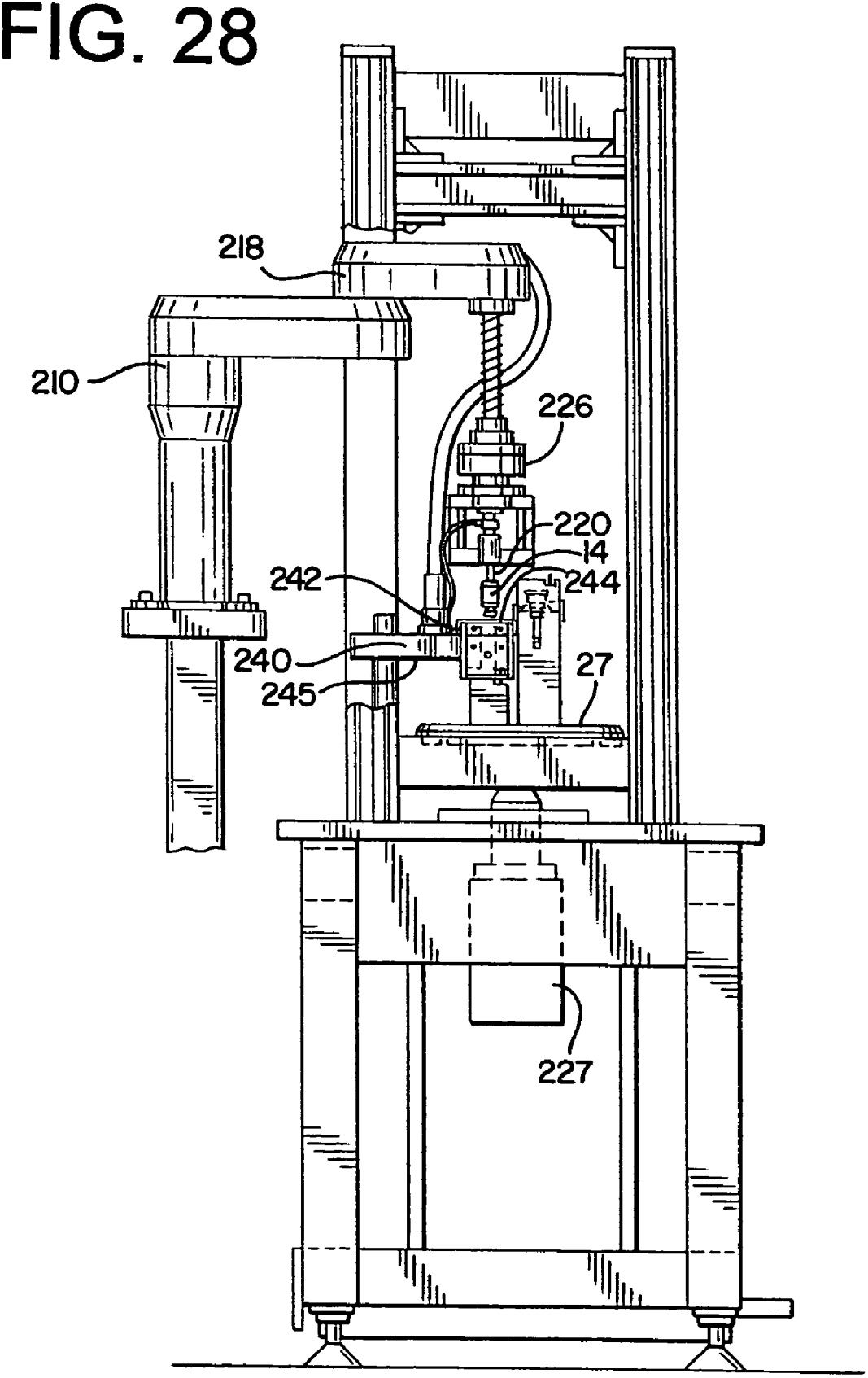
FIG. 28 is a side elevation view of a pallet load robot according to one embodiment of the present invention.
Figure 32:
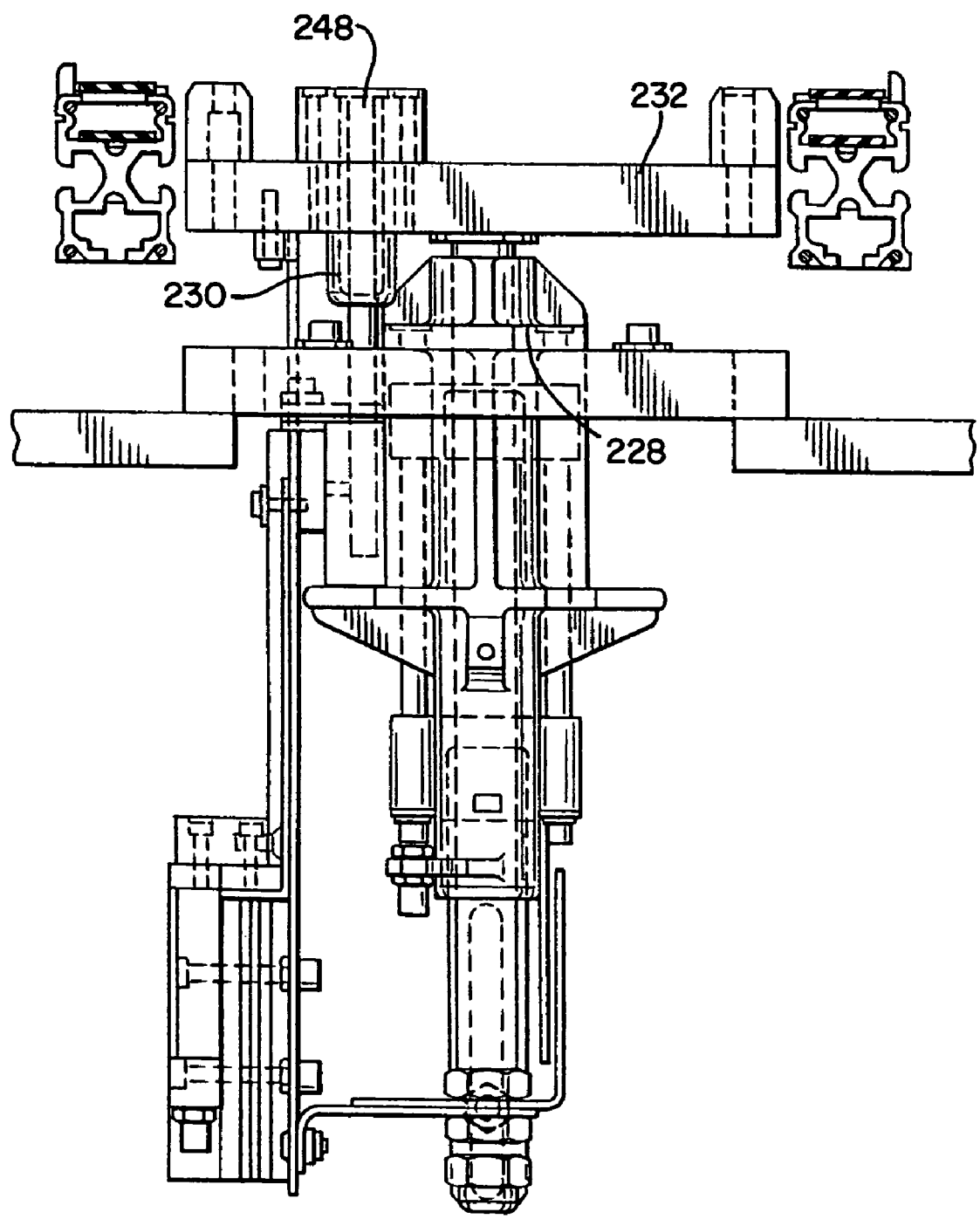
FIG. 32 is a side elevation view of a pallet lift in a first position according to one embodiment of the present invention.
Figure 33:
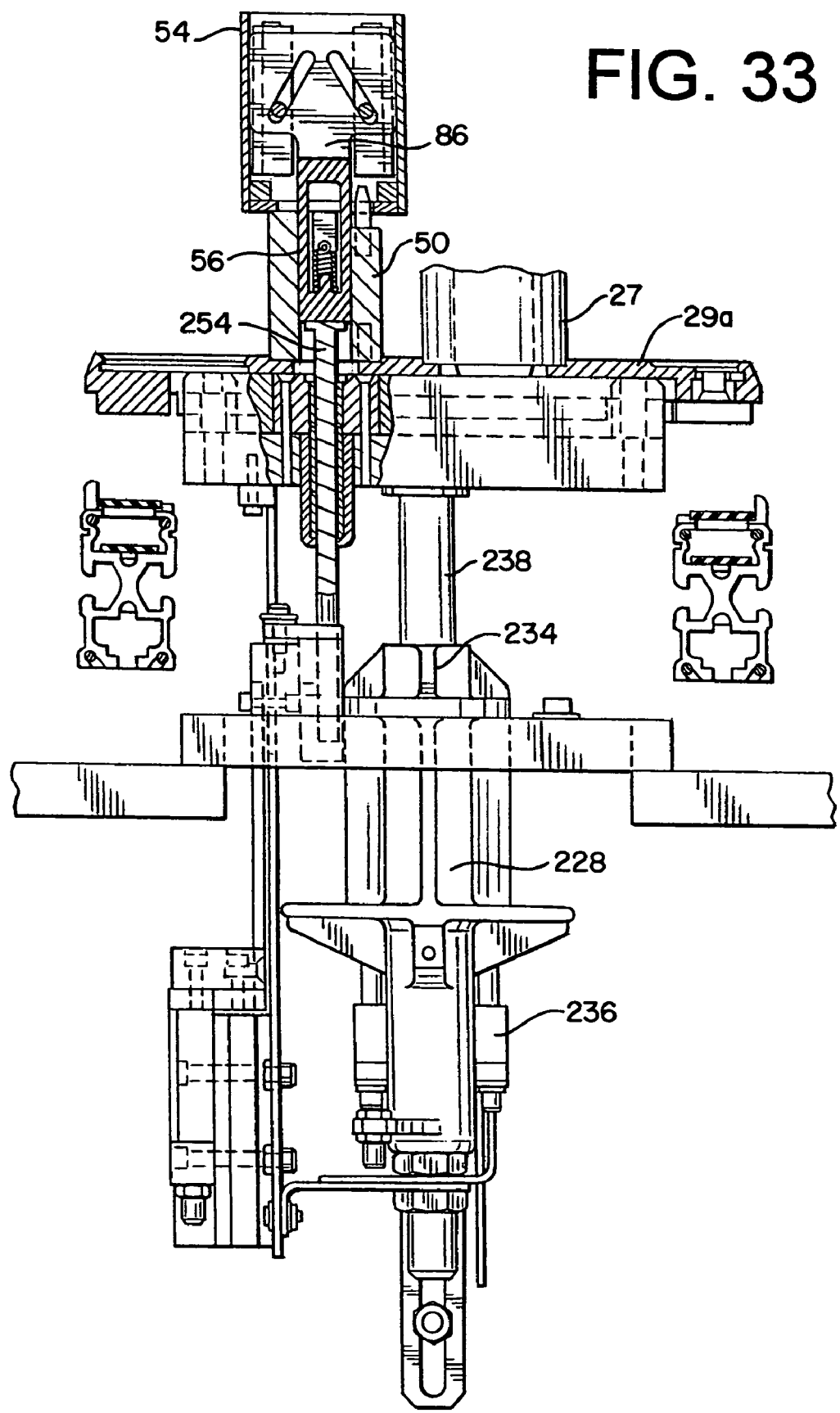
FIG. 33 is a partially cut away side view of the pallet lift of FIG. 32 in a second position.

As shown in FIG. 28, the vial pallet 27 is generally positioned proximate to the pallet load robot 210 for loading of the vial 14 onto the vial pallet 27. The container loader module 154 also generally includes the vial holder opener 227 which is positioned beneath the vial pallet transport assembly 90. As shown in FIGS. 32-33, the vial holder opener 227 generally includes a pallet lift 228 and a vial holder release mechanism 230, both of which are positioned below the powered conveyor 92.

The pallet lift 228 is shown in more detail in FIGS. 32 and 33 and generally includes a pallet support 232, a lift assembly 234 and a pallet hold down 240 (FIG. 28). The lift assembly 234 generally includes a pneumatic actuator 236 that actuates the raising and lowering of the pallet support 232 by a lift shaft 238. The pallet hold down 240, as shown in FIG. 28, generally defines the upper limit of movement for the vial pallet 27 when it is lifted by the pallet lift 228. The pallet hold down 240 generally holds the vial pallet 27 securely in conjunction with the pallet support 232. The pallet hold down 240 generally includes brackets 242 each with a horizontal extension 244 which contacts a top surface of the vial holder 54 of the vial pallet 27 when the pallet lift 228 is in a raised position. As shown in FIG. 28, the pallet hold down 240 is generally supported by a support bar 245.

The vial holder release mechanism 230, as shown in FIGS. 32 and 33 generally includes an unlatch mechanism 248. The vial holder release mechanism 230 preferably moves in conjunction with the pallet lift 228. In other embodiments, the vial holder release mechanism 230 may move independently of the pallet lift 228. The unlatch mechanism 248 generally includes an extending rod 254 (FIG. 33). The extending rod 254 is movable from a retracted position to an extended position. In the extended position the extending rod 254 preferably extends through the base plate 29a of the vial pallet 27 and engages the internal slide 56 of the container holder supports 50. The internal slide 56 is then forced upwards into the spreader plates 86,88 within the vial holder 54, opening the vial holder 54 so the vials 14 may be loaded. After the vials 14 have been loaded, the vial holder release mechanism 230 retracts and the clamp pads 76 of the vial holder 54 close around the vials 14. It is understood that the pallet load robot 210 can be programmed and adjusted so as to place the vials 14 within the vial holder 54 at a certain desired vertical location within the vial holder 54. Thus, the particular position at which the clamp pads 76 engage and hold the vials 14 can be varied and controlled as desired. Such ability to control the placement and position of the vials 14 within the vial holder 54 enhances the sterile connection between the vials 14 and the devices 10 as will be described in greater detail below.

Figure 24A:
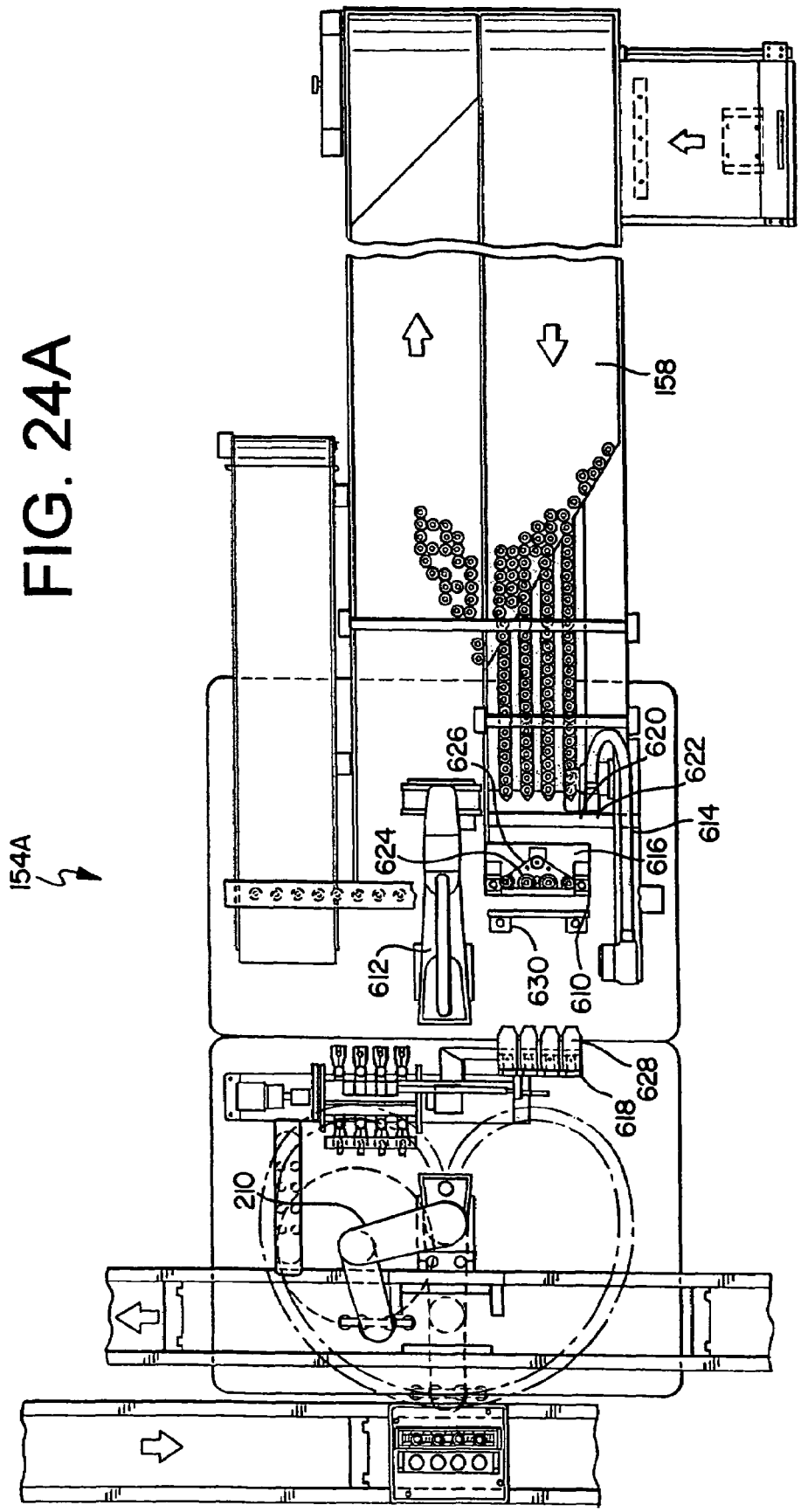
FIG. 24A is a plan view of a container loader module according to another embodiment of the present invention.
Figure 26A:
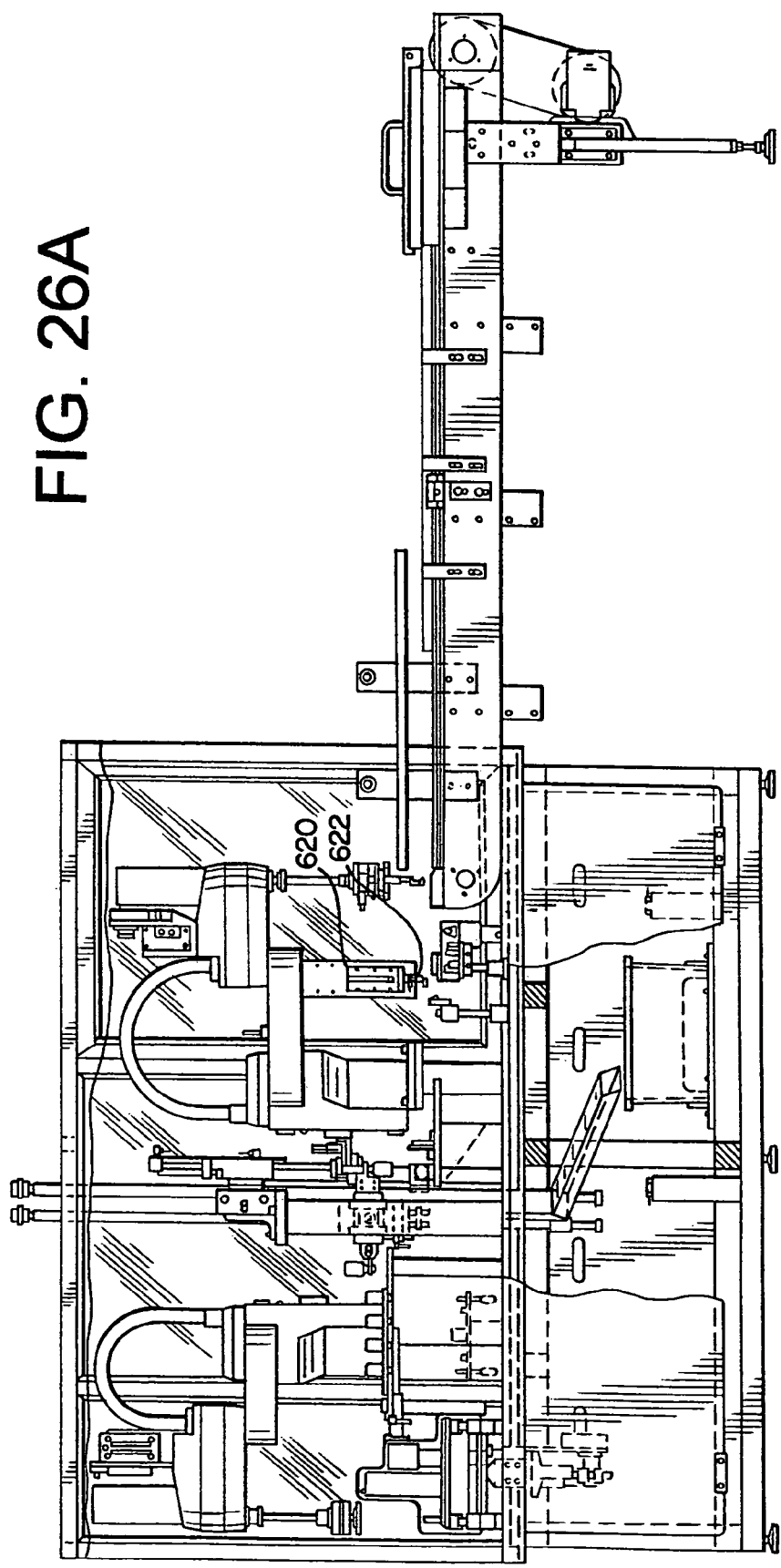
FIG. 26A is a side view of a portion of a container loader module according to one embodiment of the present invention.

FIGS. 24A and 26A show another embodiment of a container loader module 154A. This second embodiment is similar to the first embodiment described in detail above, with the exception of a modified inspection assembly 610 and container transfer robot 612. The container loader module 154A of FIGS. 24A and 26A generally includes an accumulating conveyor 158, the modified inspection assembly 610, the modified container transfer robot 612, an uncap mechanism 202, a pallet load robot 210 and a vial holder opener 227.

Each of the components of the container loader module 154 of FIGS. 24A and 26A, with the exception of the modified inspection assembly 610 and container transfer robot 612, have been previously described, and are generally similar in this second embodiment.

The modified inspection assembly 610 generally includes an inspection load robot 614, a vial rotator 616, and a camera assembly 618.

The inspection load robot 612 generally includes a robot arm 620 and an end of arm tooling 622. The inspection load robot 612 moves the robot arm 620 such that the end of arm tooling 622 is positioned above the vial presentation fixture 162 of the accumulating conveyor 158. The end of arm tooling 622 picks vials 14 from the vial presentation fixture 162, preferably four at a time. The robot arm 620 then moves the end of arm tooling 622 and vials 14 to the vial rotator 616.

The vials 14 are generally then deposited into the vial rotator 616. The vial rotator 616 generally includes a vial receiver 624 and a rotating belt 626. The vial receiver 624 receives and secures the vials 14 from the end of arm tooling 622. While positioned in the vial receiver 624, the vials 14 are preferably rotatable 360° such that a label on the vials 14 may be fully viewed and inspected by the camera assembly 618.

The camera assembly 618 generally includes cameras 628 and lights 630. Generally one camera 628 is provided for each vial 14, and here, four cameras 628 are present. The lights 630 cast illumination upon the vials 14 to facilitate inspection by the cameras 628. Vials 14 are generally loaded into the vial rotator 616, inspected by the camera assembly 618, and then picked by the modified container transfer robot 612. The container transfer robot 612 moves rejected containers onto the reject offload conveyor 200 for later operator attention. Vials 14 are generally inspected in batches of four vials 14. Acceptable vials 14 in a batch that contains a reject vial 14 are generally placed back onto the accumulating conveyor 158 by the container transfer robot 612 for recycling through the container loader module 154A.

The container transfer robot 612 is also proximate to the uncap mechanism 202. Good batches containing no reject vials 14 are transported by the container transfer robot 612 directly to the uncap mechanism 202. From the uncap mechanism 202 the vials 14 are loaded unto the vial pallet 27.

Generally, the station includes guarding built around the unit to keep personnel safely away from potentially hazardous moving parts.

Vial Holder Placement Module 260

Figure 34:
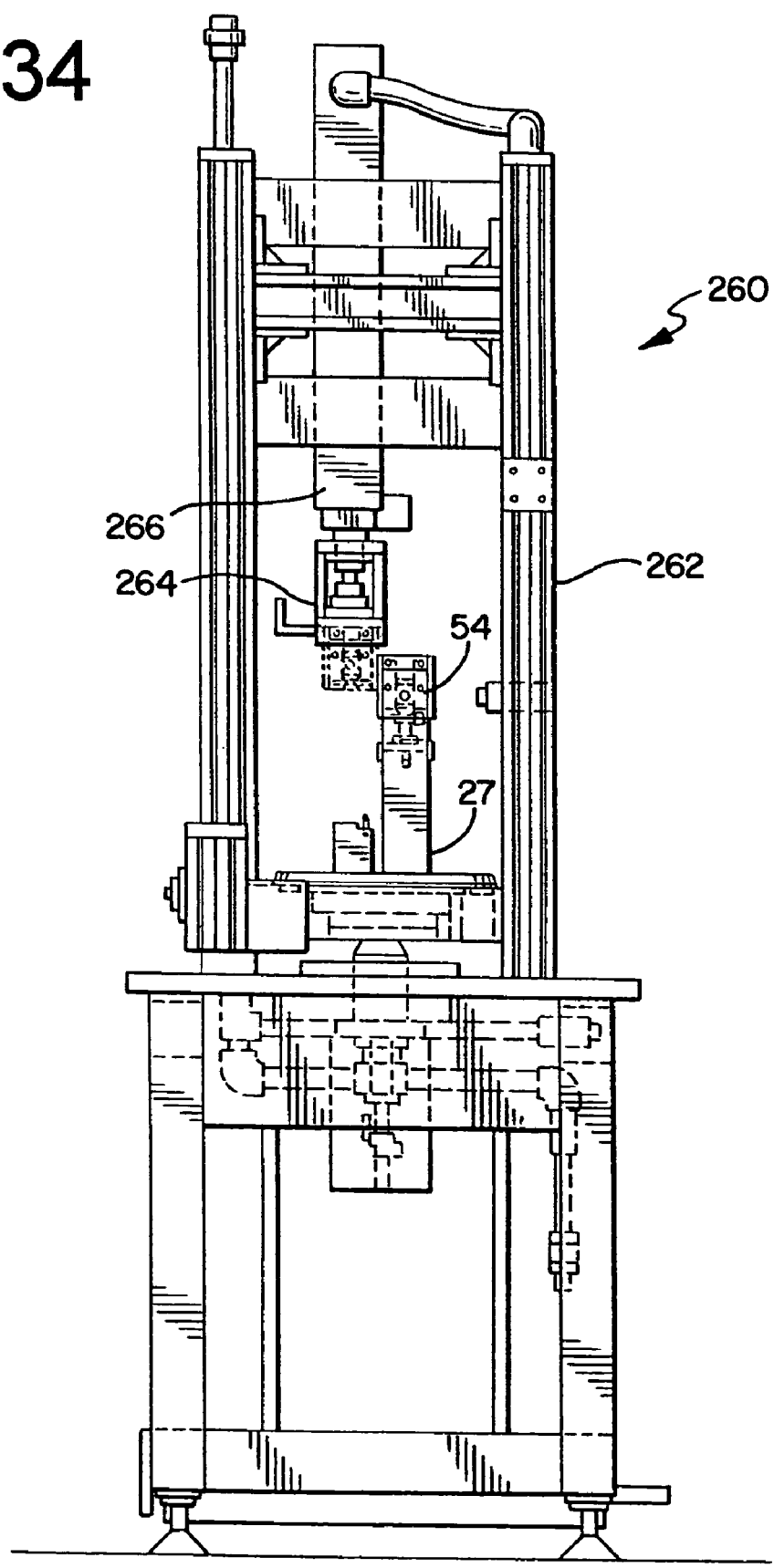
FIG. 34 is a side elevation view of a vial holder placement module according to one embodiment of the present invention.

Once the reconstitution device 10 and vial 14 are loaded onto the vial pallet 27, the pallet 27 is preferably transported by the vial pallet transport assembly 90 to a vial holder placement module 260 as shown in FIGS. 3 and 34. As shown in FIG. 3, the vial holder placement module is positioned generally downstream of the container loader module 154 and before the vial/device sterilization booth 270. As shown in FIG. 34, the vial holder placement module 260 generally includes a station base frame 262, a pick and place unit 264 and a lift and locate unit 266. As will be described in greater detail below, the vial holder placement module 260 moves the vial holder 54 with vials 14 from its initial position to the stacked or connecting position in preparation for the vials 14 to be connected to the respective reconstitution devices 10.

Vial/Device Sterilization Booth 270

Figure 35:
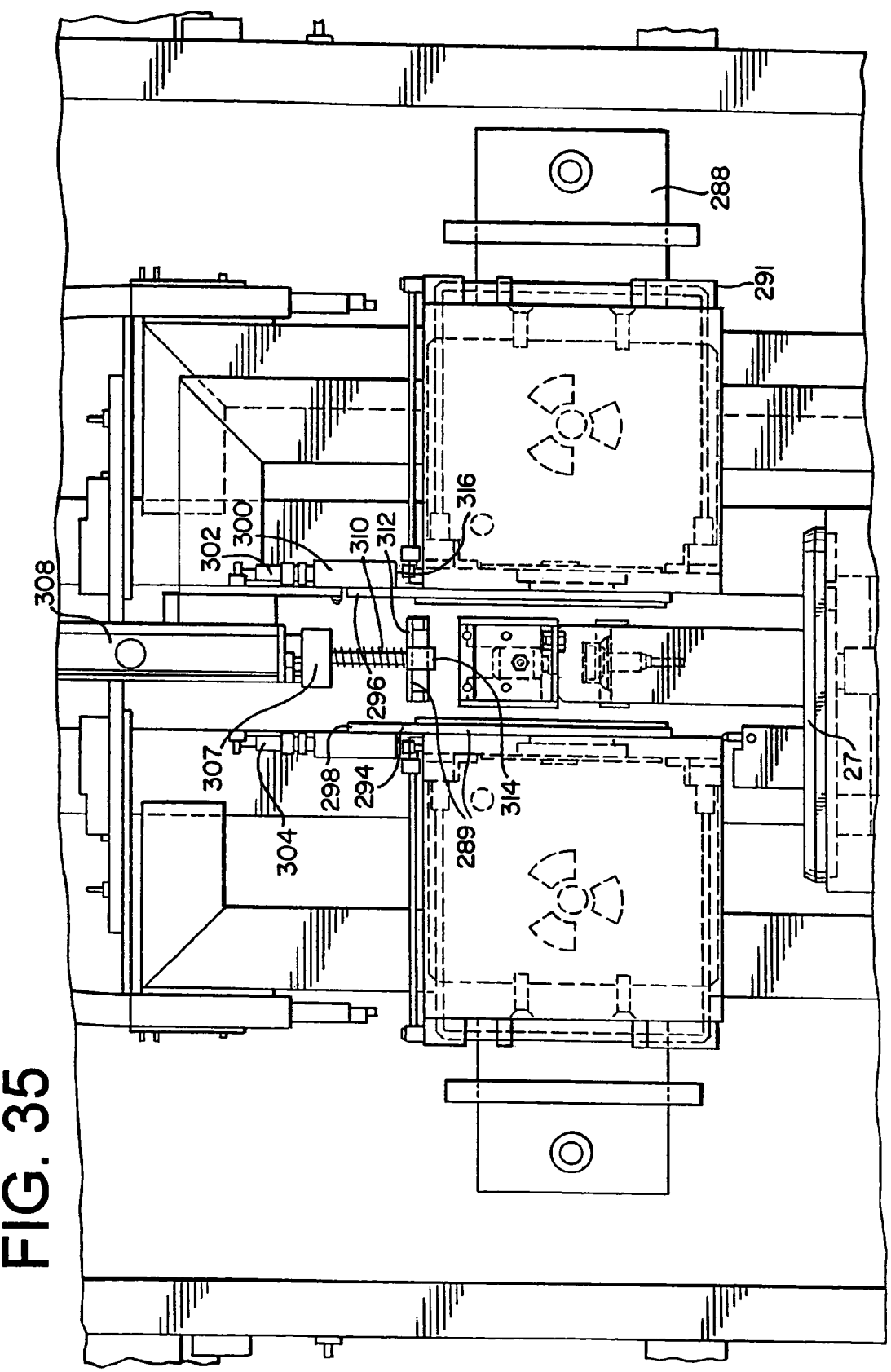
FIG. 35 is a side view of a sterilization chamber according to one embodiment of the present invention.
Figure 55:
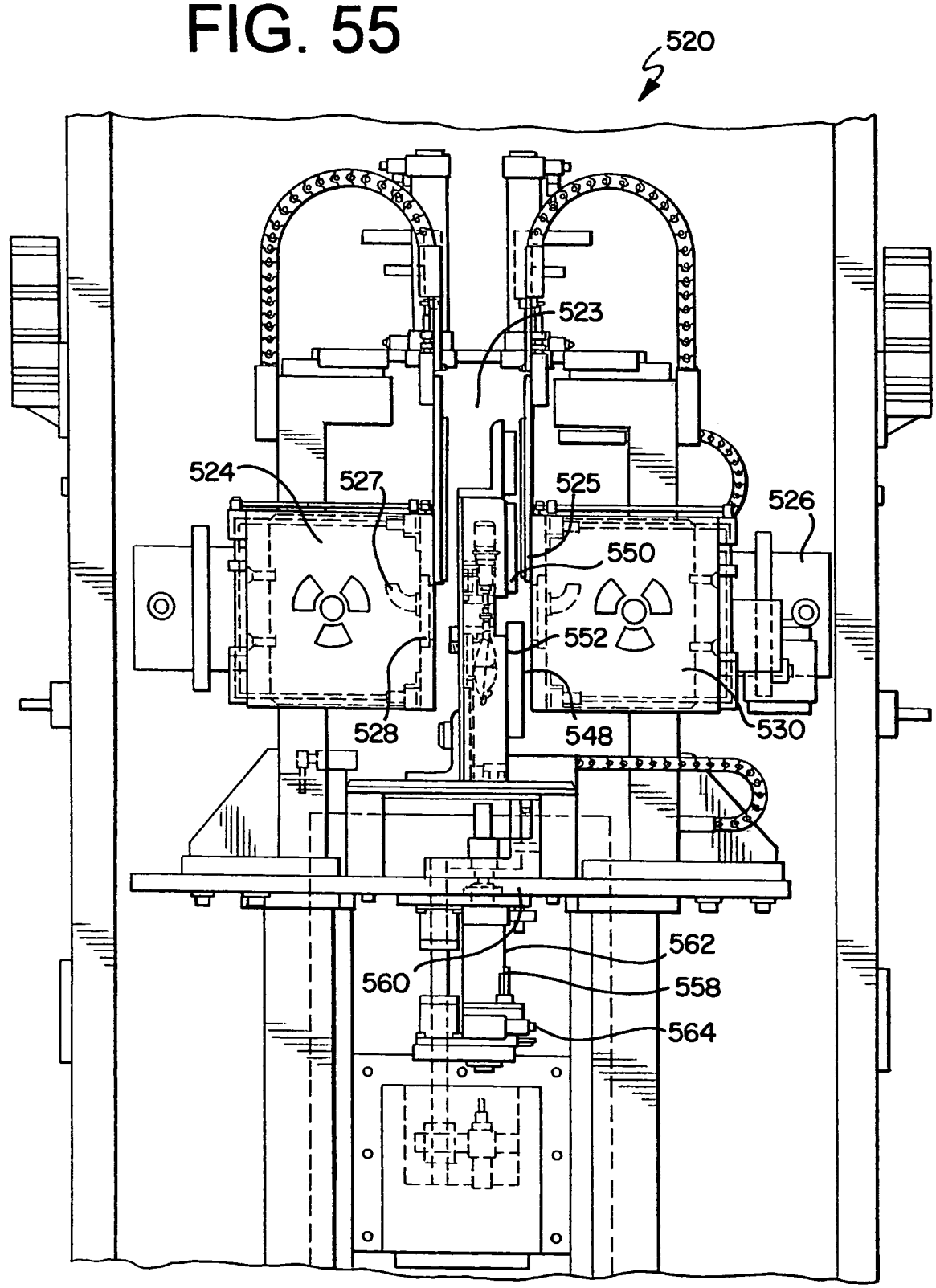
FIG. 55 is a partial side view of a second sterilization chamber according to one embodiment of the present invention.

In the preferred embodiment of the sterilization system 21, the system 21 comprises two sterilization booths: a vial/device sterilization booth 270 as shown in FIG. 35, and a bag/device sterilization booth 520, as shown in FIG. 55. The two booths 270, 520 are similar in many respects. However, differences exist between the booths 270, 520. The vial/device sterilization booth 270 will be described in detail here, and the bag/device sterilization booth 520 will be described separately, making reference to those features which are similar and those which are different.

It is important to note that there are different levels of sterilization. Therefore, a discussion on the topic must begin with the selection of a desired sterility assurance level (SAL), a measure of the probability that one unit in a batch will remain non-sterile after being exposed to a specific sterilant. For example, an SAL of $10^{-3}$ means that one device in a thousand may be non-sterile. Selecting the proper SAL may occur during a dose-setting phase of radiation sterilization validation. In many cases, the intended use of the device to be sterilized will dictate the need for a particular SAL. The commonly accepted SAL for invasive medical devices is $10^{-6}$. However, some European countries only recognize $10^{-6}$ SAL for a claim of "sterile." In such cases, the country of intended use will dictate the SAL as much as the device's intended use. It is understood that the sterilization sources are selected according to the desired or required levels of sterility assurance.

Referring to FIGS. 35-38, a preferred embodiment of the system 21 for sterilely connecting a container 14 and a reconstitution device 10 comprises a vial/device sterilization booth 270. The sterilization booth 270 generally includes a housing 277, a sterilization source or sterilizing emitter assembly 285, and a connecting mechanism 306.

Figure 36:
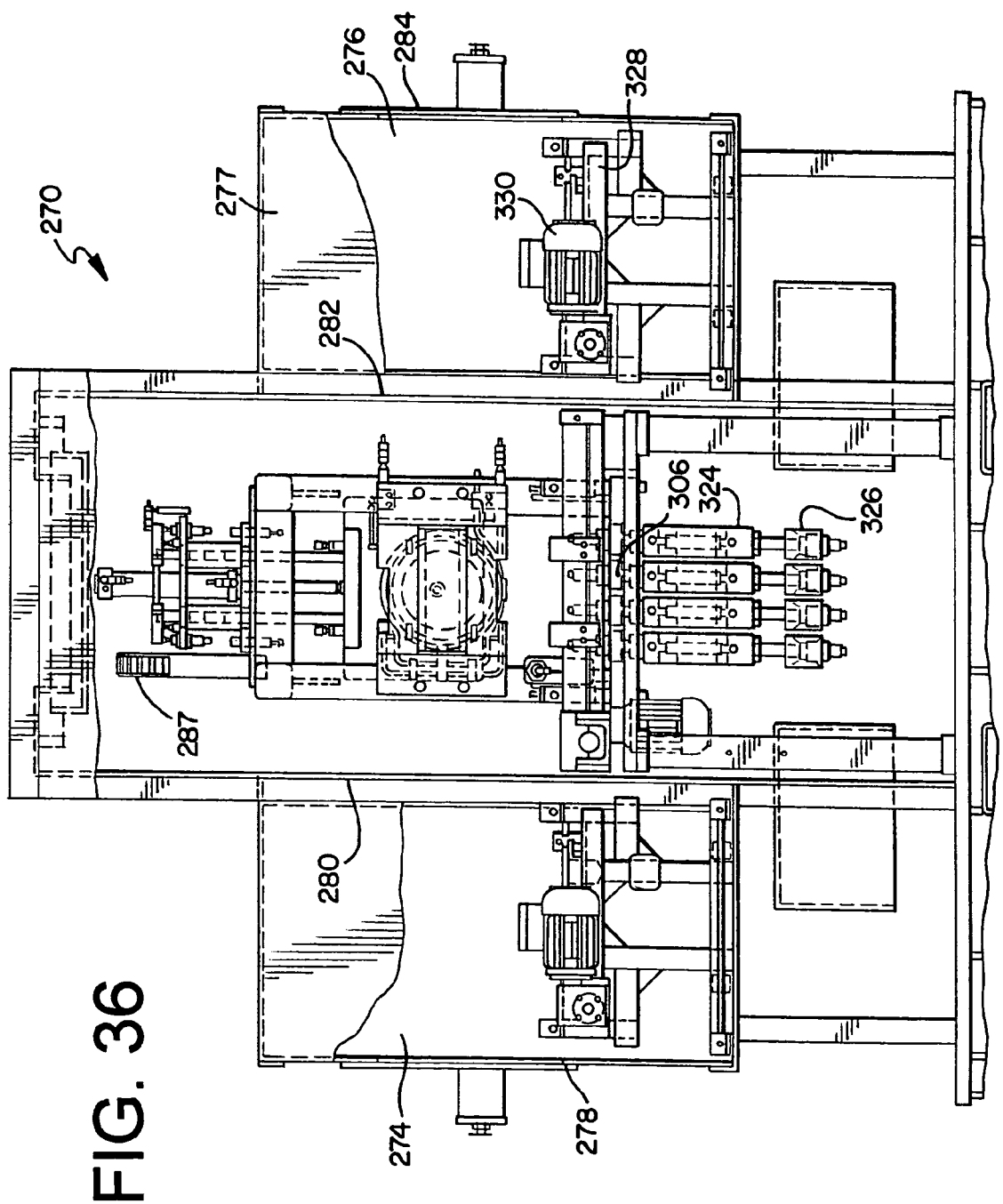
FIG. 36 is a front cross-sectional view of one embodiment of a sterilization booth of the present invention.

As shown in FIG. 36, the sterilization booth 270 generally is divided into three chambers, a sterilization chamber 272, a pre-sterilization chamber 274, and a post sterilization chamber 276. The housing 277 of the sterilization booth 270 divides the booth 270 into the sterilization chamber 272, pre-sterilization chamber 274, and post sterilization chamber 276, and generally provides shielding from the environment external to the sterilization booth 270.

Each chamber generally includes doors, generally a set of entrance doors and a set of exit doors. In the preferred embodiment, each individual door includes two panels which slide apart to open the door. The panels are preferably comprised of a lead core with a stainless steel exterior lining.

Referring to FIG. 36, the entrance doors 278 for the pre-sterilization chamber 274 are shown. The exit doors 280 for the pre-sterilization chamber 274 also act as the entrance doors for the sterilization chamber 272. Likewise, the sterilization chamber exit doors 282 also function as the post-sterilization chamber entrance doors. The exit doors 284 for the post-sterilization chamber 276 are also shown. The doors are preferably sliding doors actuated by, for example, a hydraulic source reacting to a sensor (not shown) and a control system (not shown). These components are well known by those skilled in the relevant art and implementation of such components would be well understood.

The sterilization booth housing 277 is preferably arranged to prevent exposure outside of the sterilization booth 270 to the sterilization source 285. In a preferred embodiment, radiation created by a low-energy electron beam (e-beam) source functions as the sterilization source 285, and the sterilization booth housing 277 includes shielding to prevent undesired outside exposure. Use of a higher energy source may require additional shielding. The housing 277 is also comprised of an appropriate ventilator 287 due to the creation of exhaust, generally ozone, from the sterilization source.

The sterilizing emitter assembly 285 (FIG. 37) generally includes a low energy e-beam source 286 and a vial pallet shielding 289. The e-beam source 286 is arranged to provide a sterilizing dose of e-beam radiation at a location contemplated for the connecting of the vial 14 and the reconstitution device 10.

In one preferred embodiment, the e-beam source 286 generally comprises two oppositely positioned low-energy e-beam tubes 288. Suitable e-beam tubes are commercially available from a number of different sources. These presently preferred e-beam tubes generally operate in the range of 60 to 150 KeV. The resulting electron field, or cloud, produced by each e-beam tube has been estimated at approximately 5 cm×25 cm×5 cm (h×w×d), but may vary considerably within the preferred range of energies and other factors. Other suitable electron beam tubes may exist and those skilled in the art would understand what modification would be necessary to implement such tubes into an embodiment of the present system.

The e-beam tubes 288 are generally supported by tube holders 291. The tube holders 291 position the e-beam tubes such that an electron cloud or sterilizing field may be formed within the sterilization chamber 272.

While two electron beam tubes are preferred for the present embodiment, it is contemplated that a single electron beam could be used in some applications. For example, the engaged components to be connected could be rotated within the resulting electron cloud to effect sterilization, or the source beam could revolve about the components for the same effect. Additionally, any number of electron beam tubes may be used in an array fashion to further address shadowing of very complicated connections or oddly shaped components.

While the preferred sterilization source 250 comprises low energy e-beams, other sterilization sources are contemplated for use in conjunction with the present invention. For example, alternative embodiments may include the use of a high energy e-beam sterilization source, a chemical vapor sterilization source, a gas discharge sterilization source, a steam sterilization source, and a pulse light sterilization source, among others.

FIG. 35 shows the sterilization chamber 272 with a vial pallet 27 contained therein. As explained in greater detail below, the vials 14 may have two positions within vial holder to enhance the sterilization process associated with the connection between the vial 14 and the device 10. Within the sterilization chamber is a connection area to which the vial pallet 27 is conveyed and positioned for the contemplated sterile connection of the vial 14 and reconstitution device 10. The e-beam tubes 288 are preferably positioned on two sides of the sterilization chamber 272. The e-beam tubes 288 are arranged to form a sterilizing field within the connection area.

The vial pallet shielding 289 generally comprises movable shutters 294, 296 and a vial back-up mechanism 307. The movable shutters 294, 296 are mounted on shutter support structures 298, 300. The shutters include actuators 302, 304 which slide the shutters 294, 296 upward on demand. The shutters 294, 296 block the e-beam radiation from reaching the sterilization chamber 272 until they are moved upwards, preferably exposing the vial pallet 27, to the e-beam radiation sterile field. The actuators 302,304 are preferably pneumatic cylinders. The shutters 294, 296 preferably include coolant ports 316 which provide a flow of a coolant through the shutters 294, 296. The coolant preferably travels through each of the shutters in a boustrophedonic pattern.

The vial pallet shielding 289 also generally includes the vial back-up mechanism 307, preferably positioned within the sterilization chamber 272. The vial back-up mechanism 307 includes an electric servo-driven actuator 308. A positioning shaft 310 extends downward from the actuator 308. A vial holder shield 312 is mounted to the positioning shaft 310. The vial holder shield 312 is a shielding metal such as steel, lead, or combinations thereof. The shield 312 is sized to fit in a top opening of the vial holder 54, and shield the top of the vial holder 54. A vial positioning tool 314 preferably extends downward from the vial holder shield 312. The vial positioning tool 314 generally includes four extensions which fit into the diamond shaped openings of the vial holder 54 to access the vials 14 and further position the vials 14 as necessary or desired.

Figure 35A:
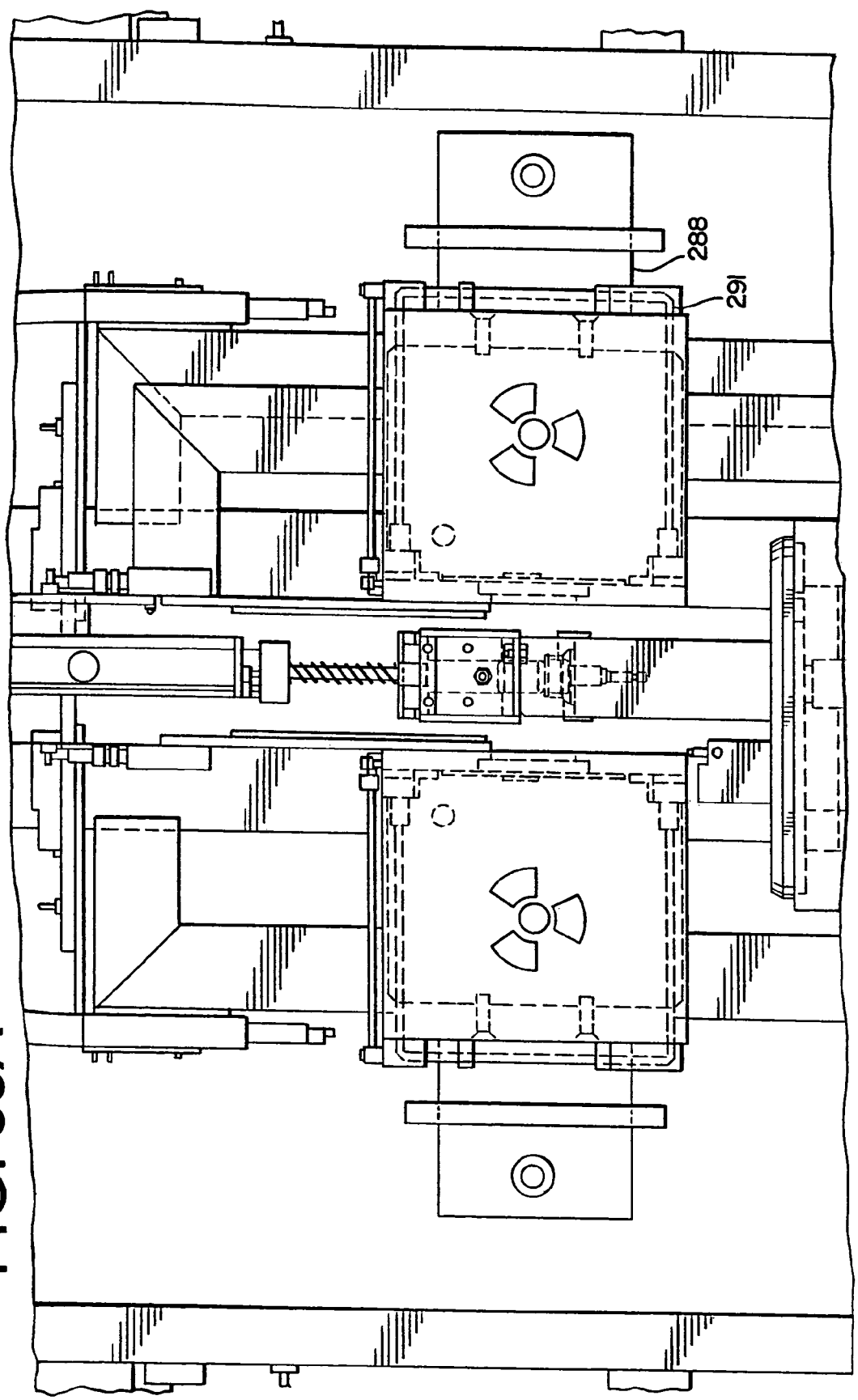
FIG. 35A is a side view of the sterilization chamber of FIG. 35 in a connecting position.

The vial pallet shielding 289 works cooperatively with the vial pallet 27 to shield the body of the vials 14 from the radiation while exposing a neck of the vials 14 such that the vials 14 may be connected to the reconstitution devices 10 within a sterilizing field. In particular, and as shown in FIGS. 4, 35 and 35A, the housing 59 of the vial holder 54 on the vial pallet 27, and the vial holder shield 312 shield the vials 14. In this manner, the vial pallet 27 and sterilization booth 270 work cooperatively to shield those parts of the containers that should be shielded while exposing those parts that are contemplated for connection within the sterilizing field.

Figure 37:
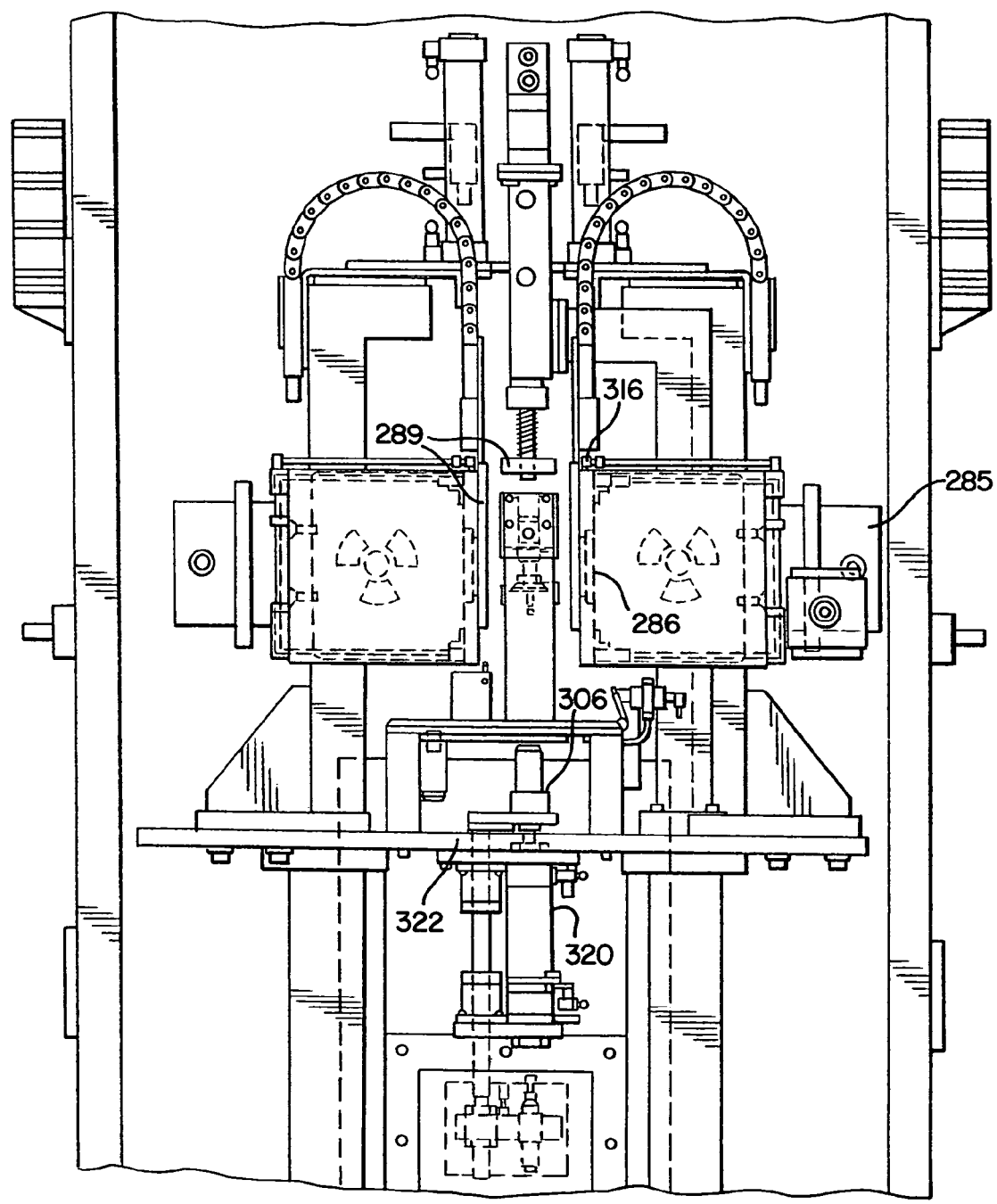
FIG. 37 is a side cross-sectional view of the sterilization booth of FIG. 36.
Figure 38:
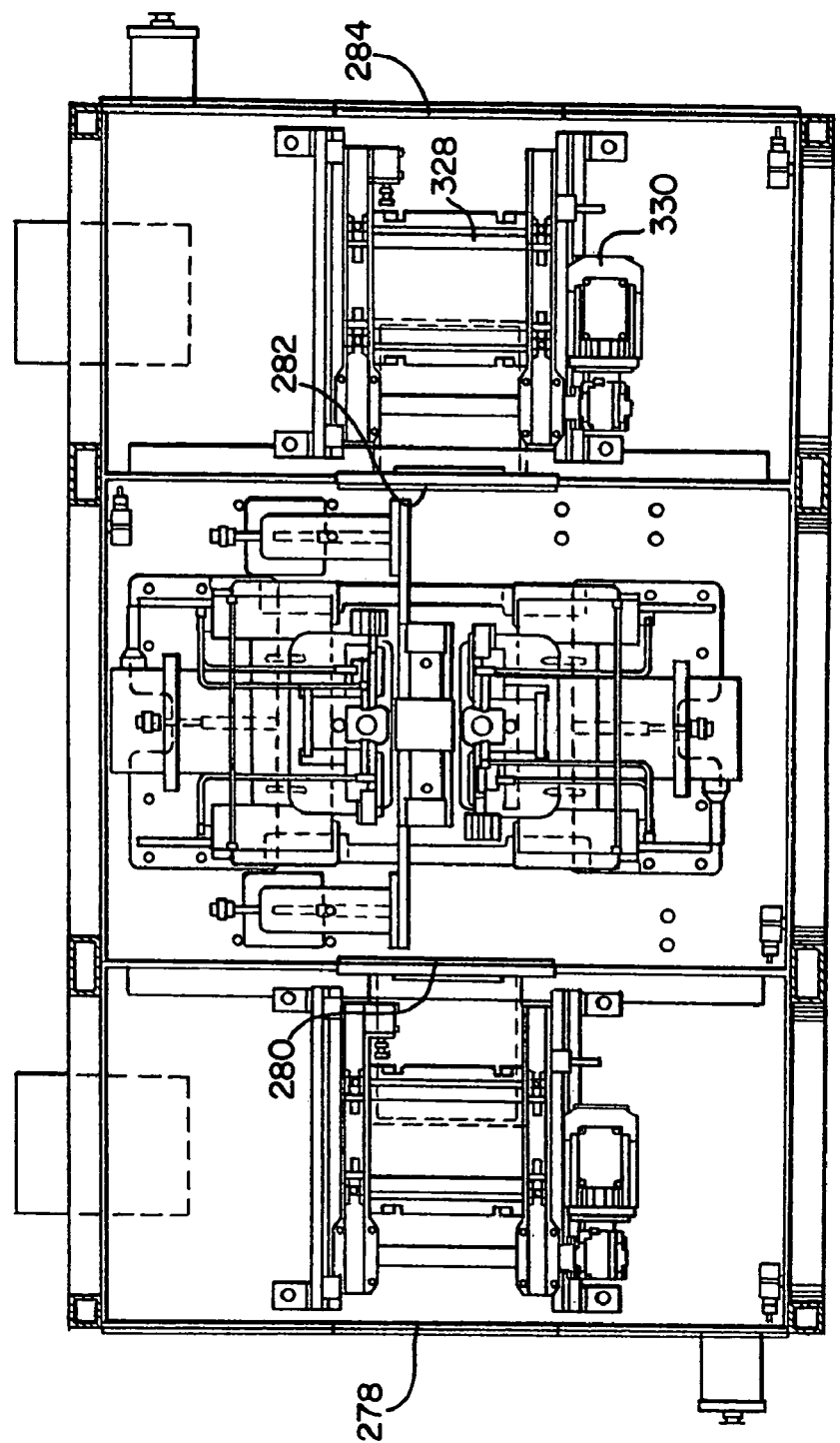
FIG. 38 is a top cross-sectional view of the sterilization booth of FIG. 36.

As shown in FIG. 37, the sterilization booth 270 also includes the connecting mechanism 306 for connecting the vials 14 to the reconstitution devices 10. The connecting mechanism 306 generally includes a snap-closure mechanism 320. The snap-closure mechanism 320 is generally mounted to a base-plate 322 underneath the sterilization chamber 272. The snap-closure mechanism 320 preferably includes four independent pneumatic cylinders 324. The pneumatic cylinders 324 preferably include electronic position feedback sensors 326 (FIG. 36).

The pre-sterilization chamber 274, sterilization chamber 272, and post-sterilization chamber 276 each preferably include an individual conveyor 328. Each conveyor 328 moves the vial pallet 27 through a chamber of the sterilization booth 270. The conveyors 328 may be considered as part of the vial pallet transport assembly 90. The conveyors 328 are preferably toothed-belt type conveyors, but may be of any type. Preferably, each conveyor 328 includes its own motor 330.

Vial Holder Removal Module 340

Figure 39:
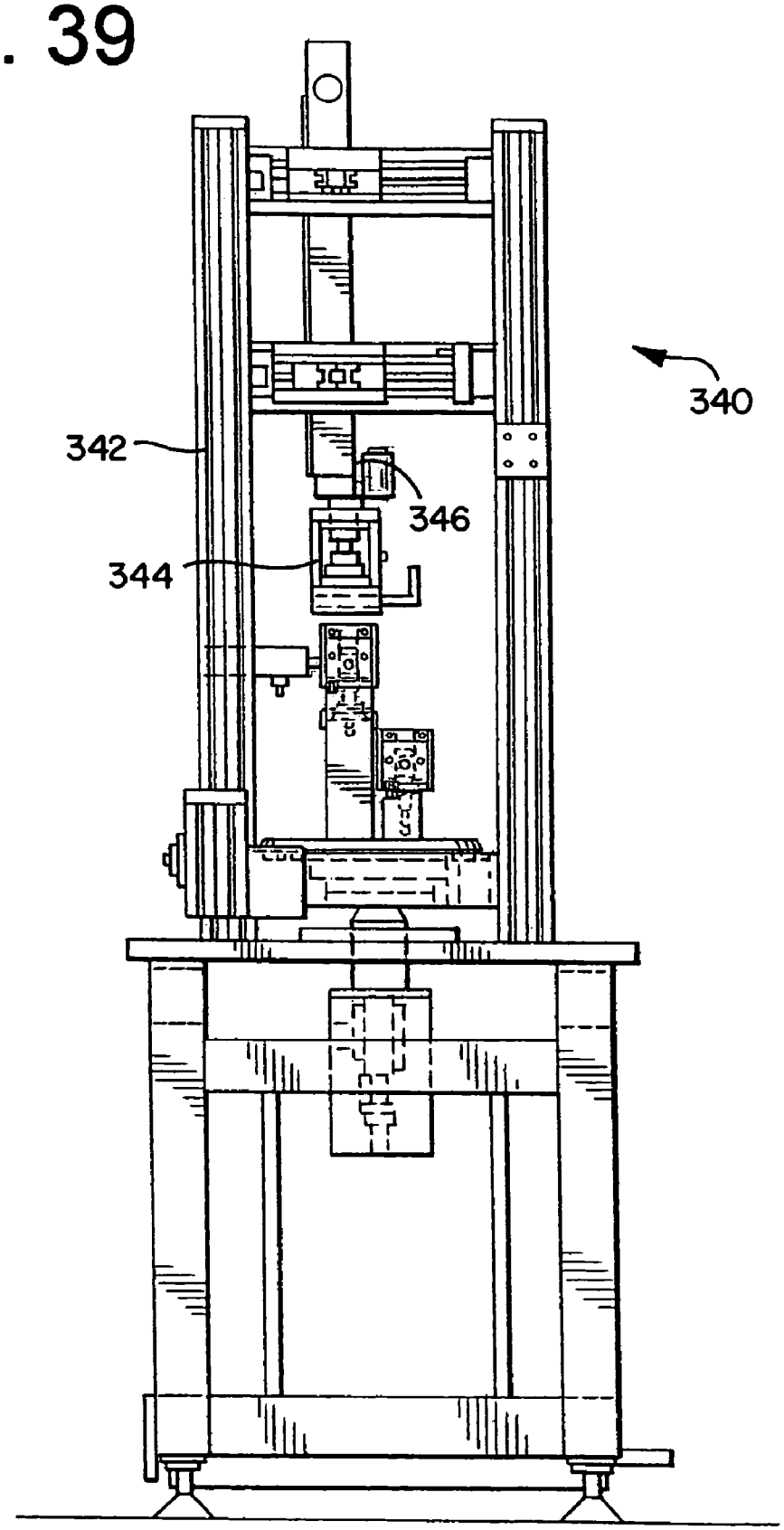
FIG. 39 is a side elevation view of a vial holder removal module according to one embodiment of the present invention.

Preferably, after exiting the post-sterilization chamber 274 of the sterilization booth 270, the vial pallet 27 is conveyed by a section of the vial pallet transfer assembly 90 to a vial holder removal module 340 as shown in FIG. 39. The vial holder removal module 340 generally moves the vial holder 54 of the vial pallet 27 from the stacked connecting position to its original unstacked position on the vial pallet 27. The vial holder removal module 340 is similar to the vial holder placement module 260 of FIG. 34. The vial holder removal module 340 also generally includes a station base frame 342, a pick and place unit 344 and a lift and locate unit 346.

Figure 40:
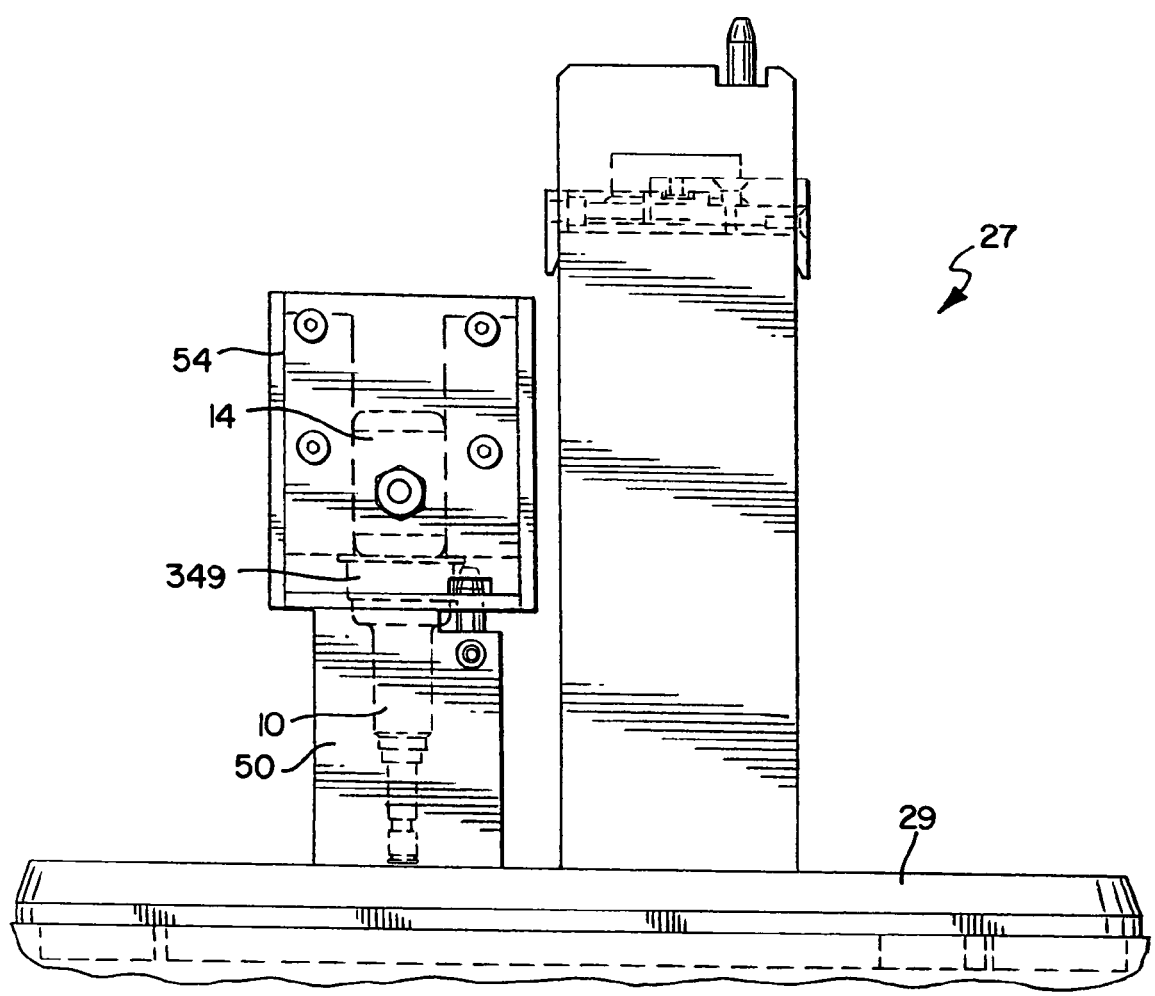
FIG. 40 is a side view of a loaded positioning assembly after connection in an unstacked loading position.
Figure 41:
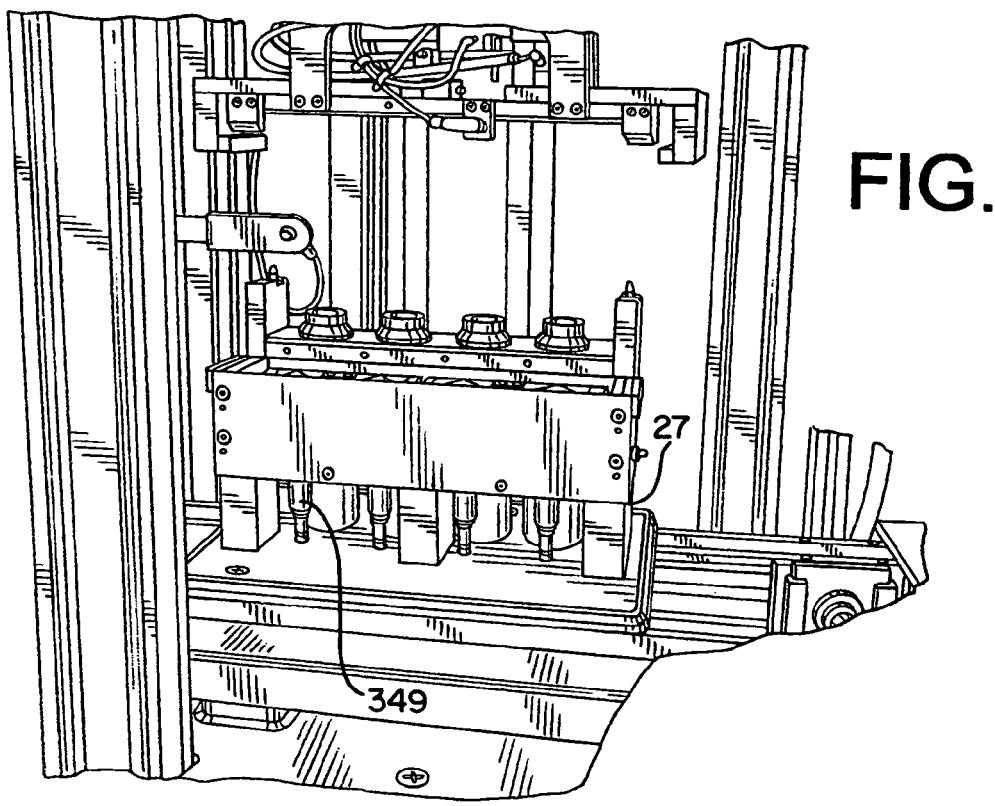
FIG. 41 is a partial perspective view of a depalletizing device and vial station according to one embodiment of the present invention.

Preferably, when the vial holder 54 of the vial pallet 27 is placed into an unstacked unloading position, a reconstitution device/vial subassembly 349 remains in the vial holder 54 portion of the vial pallet 27 as shown in FIGS. 40 and 41. The reconstitution device/vial subassembly 349 is formed when the reconstitution device 10 and vial 14 are connected.

Depalletize Device/Vial Module 350

After the reconstitution device 10 and vial 14 are connected to form the reconstitution device/vial subassembly 349, and the vial holder removal module 340 has moved the vial holder 54 onto the container holder supports 50 on the vial pallet, the vial pallet 27 is then preferably transferred by the vial pallet transport assembly 90 to the depalletize device/vial module 350, as shown in FIG. 41-44.

The depalletize device/vial module 350 generally comprises a vial holder opener 351 and a transfer robot 354. The vial holder opener 351 is preferably the same as the vial holder opener 227 discussed above in conjunction with the container loader module 154 and detailed in FIGS. 32-33. The vial holder opener 351 generally includes a pallet lift 352 and a vial holder release mechanism (not shown), both of which are positioned below the powered conveyor 92.

The transfer robot 354 generally includes a robotic arm 356 and an end of arm tooling assembly 358. The robotic arm 356 generally allows for moving the tooling assembly 358 between the vial holder 54 of the vial pallet 27 and the shrinkband applicator 360. The transfer robot 354 is preferably fixed to a station base table assembly 361.

The end of arm tooling assembly 358 generally includes suction cups 362 for securing the reconstitution device/vial subassemblies 349. A positive vacuum is preferably applied through the suction cups 362. Preferably there are four suction cups 362 aligned in a row on a support 364 which is then secured to the transfer robot 354. Generally, the station includes guarding built around the unit to keep personnel safely away from potentially hazardous moving parts.

Shrinkband Applicator 360

Figure 43:
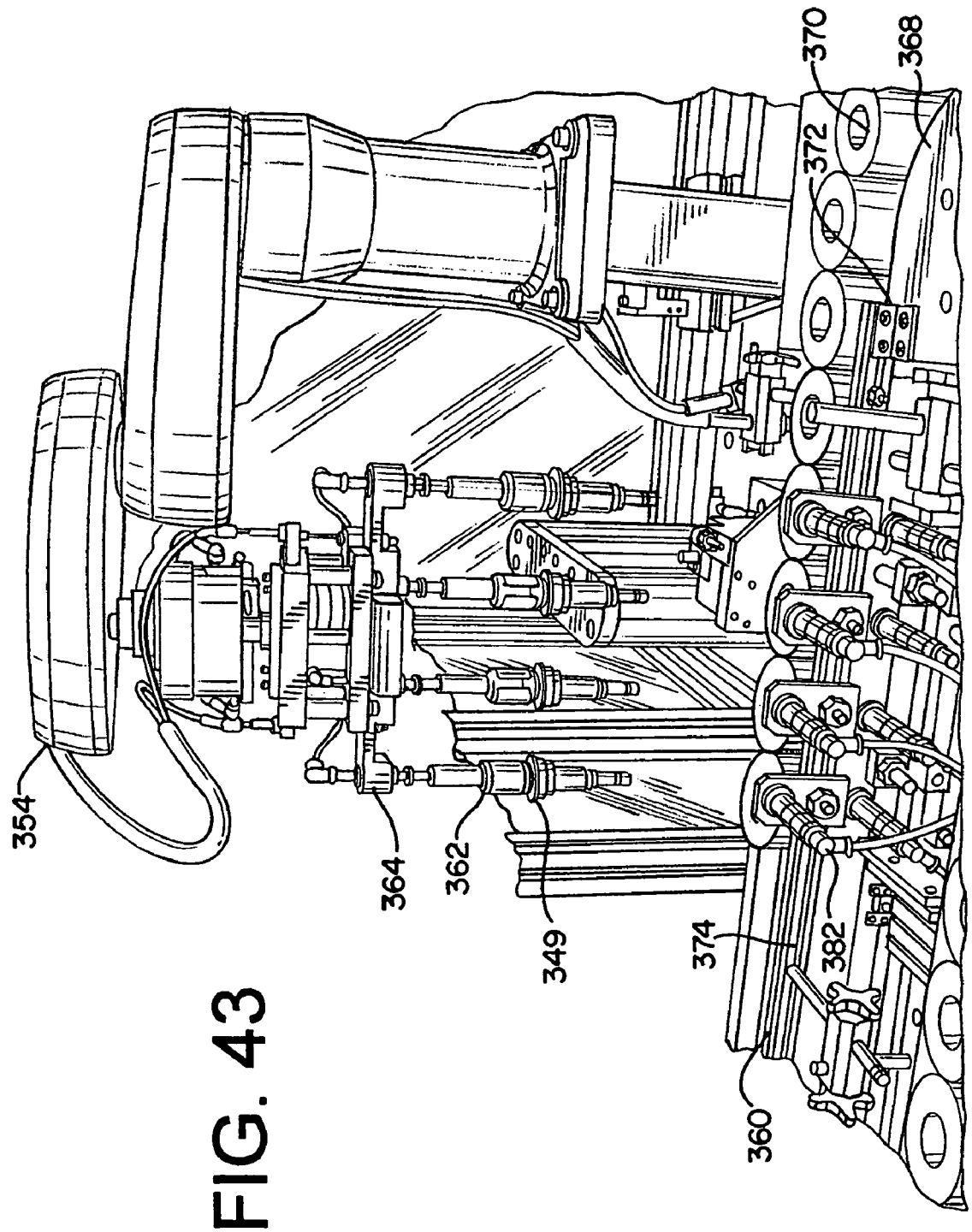
FIG. 43 is another partial perspective view of the depalletizing device and vial station of FIG. 41.
Figure 44:
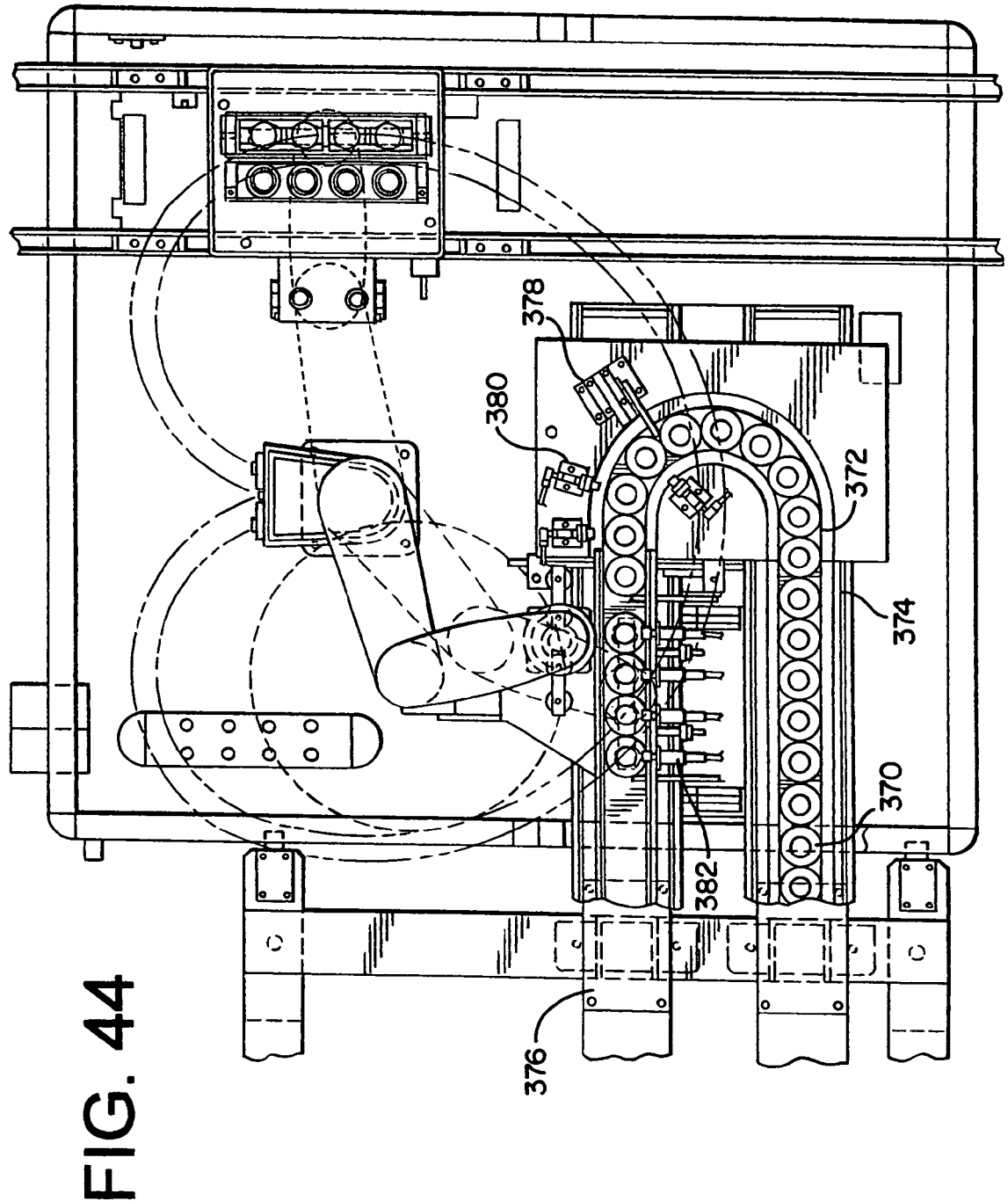
FIG. 44 is a top view of the depalletizing device and vial station of FIG. 41.

The shrinkband applicator 360 generally includes a power and free puck conveyor 368, a shrinkband application station 365 and an oven 367, as shown in FIGS. 3, 43, and 44. The puck conveyor 368 generally includes individual pucks 370 which are supported between guide rails 372 on a conveyor 374. The individual pucks 370 receive reconstitution device/vial subassemblies 349 and transports them through the shrinkband application station 365 and the oven 367. The puck conveyor 368 preferably includes a puck stop and locate assembly 378. This assembly 378 preferably includes puck stops 380 and part present sensors 382. As described in greater detail below, the shrinkband applicator 360 applies a shrinkband around the vial 14 and portion of the gripper assembly of the reconstitution device 10, as shown in FIG. 2A.

Second Cell: Bag/Device Subassembly Connection System 25

In one embodiment of the present invention the reconstitution assembly apparatus 21 includes a second cell 25 wherein the reconstitution device/vial subassembly 349 is sterilely joined to the first container 12, preferably a flexible diluent container 12 as discussed. The flexible diluent container 12 is preferably a bag 12 as shown in FIGS. 1 and 2. The connection of the device/vial subassembly 349 to the bag 12 is preferably an automated process wherein the device/vial subassembly 349 and bag 12 are joined in a sterile manner.

As shown generally in FIG. 3, the second cell 25, or bag/device subassembly connection system 25 generally includes a second positioning assembly, or bag pallet 402, a bag pallet transport assembly 444, a palletize device/vial subassembly module 448, a bag load module 478, a nozzle blow-off module 500, a bag/device subassembly sterilization booth 520 and a depalletize reconstitution assembly module 568.

While all of the modules will be described, it is appreciated that some modules could be altered or removed without moving out of the concept of the invention as claimed in the appended claim set. This understanding also applies to the modules described with respect to the vial/device connection system 23.

Second Positioning Assembly 402 (Bag Pallet)

Figure 45:
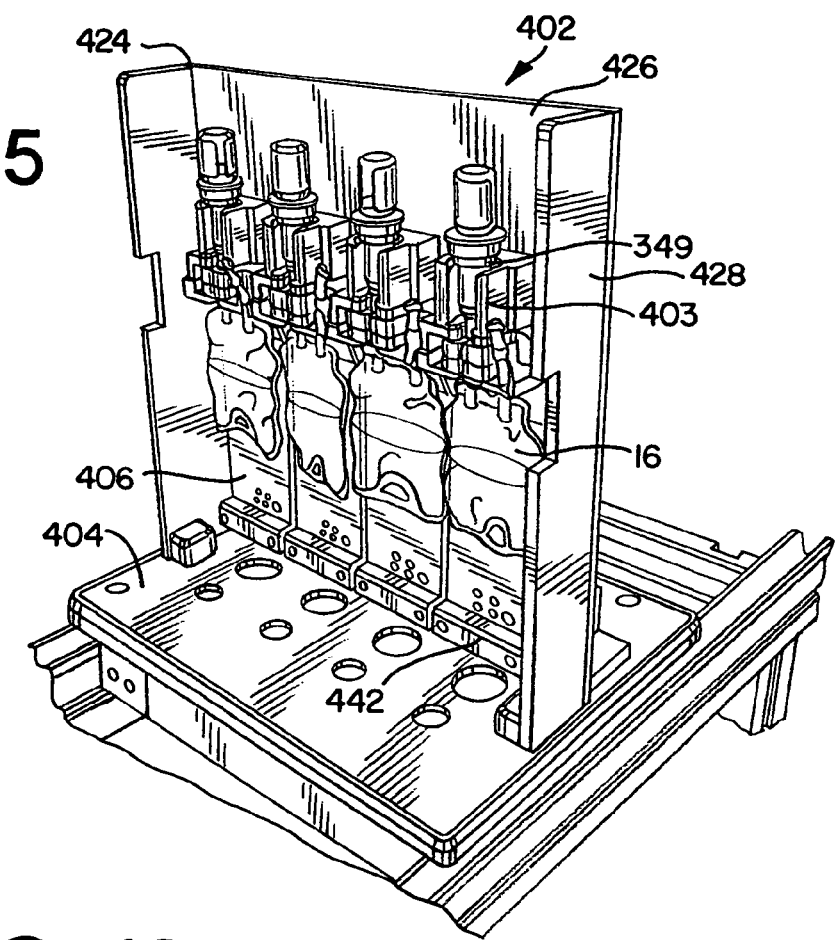
FIG. 45 is a perspective view of second positioning assembly according to one embodiment of the present invention.
Figure 46:
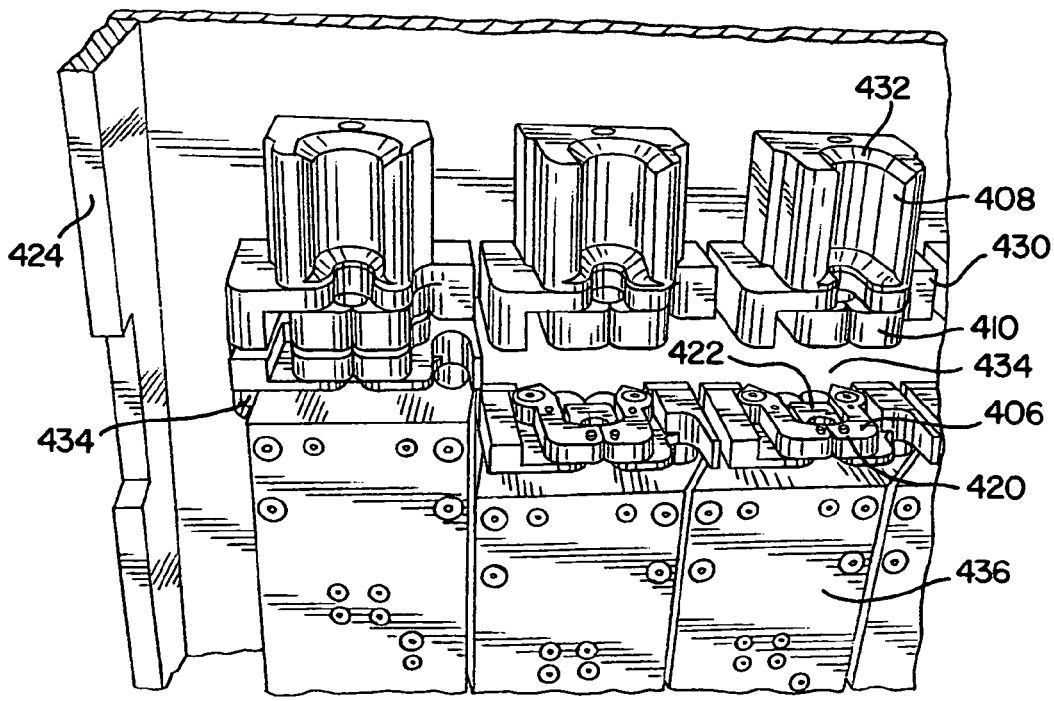
FIG. 46 is a partial perspective view of the second positioning assembly of FIG. 45.

The bag pallet 402 is generally shown in FIGS. 45-50. As shown in FIGS. 45 and 46, the bag pallet 402 generally includes a pallet base 404, a device/vial subassembly holder 408, a container or bag holder 406, and a support frame 424. The various components of the bag pallet 402 are generally supported on the pallet base 404 and move through the second cell 25 on the pallet base 404. The pallet base 404 generally has holes which pass through it aligned with the bag holder 406 such that the bag holder 406 may be pushed upwards by accessing it through the pallet base 404.

The device and vial subassembly holder 408 of the bag pallet 402 generally includes a device gripper 410, a device support block 430, and a vertical mounting support 432. The device/vial subassembly holder 408 is generally attached to the frame 424. It should be understood that in other embodiments, the device/vial subassembly holder 48 may be simply a reconstitution device holder. This may occur when it is desirable to not attach a vial or other drug container to the reconstitution device, but only to connect the first container 12 to the reconstitution device 10.

Figure 48:
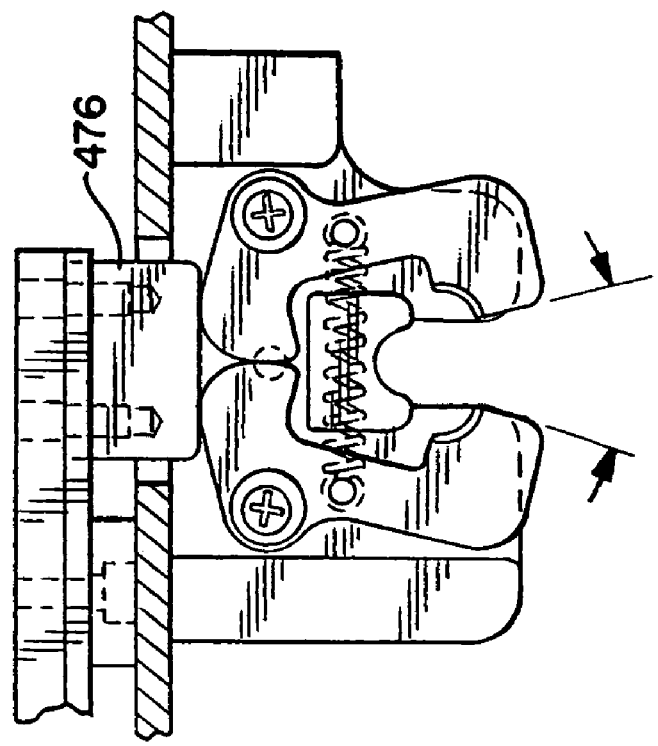
FIG. 48 is a top view of the device gripper of FIG. 47, the device gripper shown in an opened position.
Figure 47:
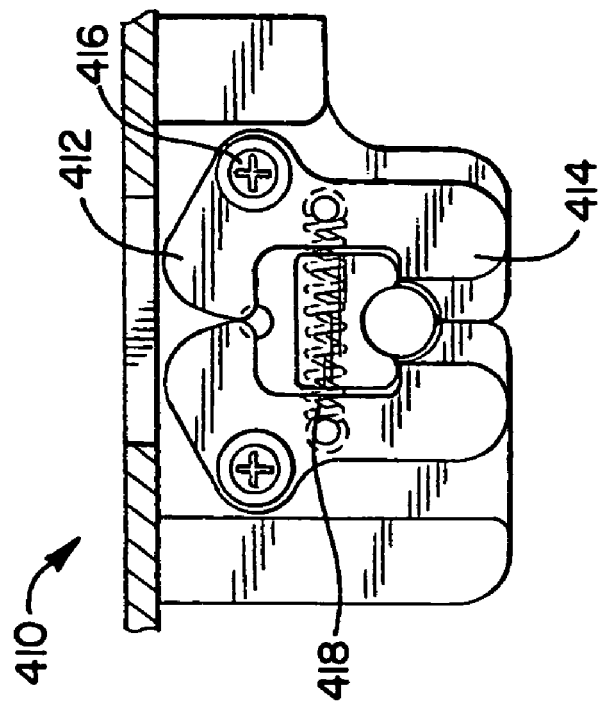
FIG. 47 is top view of a device gripper of the second positioning assembly according to one embodiment of the present invention.

The device gripper 410 is shown in greater detail in FIGS. 47-48. The device gripper 410 is preferably sized to grasp a portion of the reconstitution device 10 of the device/vial subassembly 349 generally proximate to an end which is to be sterilely connected to the bag 12. In this embodiment, the device gripper 410 generally includes activation members 412 and gripping members 414 pivotally joined to one another. As shown in FIG. 47, the activation members 412 are joined at a pivot 416 to the gripping members 414. The activation members 414 and gripping members 414 are preferably formed from a continuous piece of material, preferably stainless steel. Attached to each of the gripping members 414 is a tension spring 418 which biases the device gripper 410 into a closed position.

The device support block 430 and the vertical mounting support 432 of the device/vial subassembly holder 408 are generally located above the device gripper 410. The vertical mounting support 432 generally has a shape complementary to the shape of the device/vial subassembly 349 such that it provides support about a portion of the device/vial subassembly 349 when one is placed into the bag pallet 402.

As also shown in FIGS. 45 and 46, the bag holder 406 generally includes a bag gripper 420 and a bag back support plate 436 arranged to hold the bag 16 within the bag pallet 402. The bag gripper 420 preferably operates by the same pivoting mechanism of the device gripper 410 used to secure the device/vial subassembly 349. The bag gripper 420 preferably also includes a shielding plate 422 positioned between the gripping members. The bag gripper 420 is generally mounted to the bag back support plate 436. As shown in FIG. 45, the bag 12 is preferably suspended from the bag gripper 420.

The bag back support plate 436 is preferably slidingly mounted to the frame 424 such that it may slide up and down within the bag pallet 402. This is generally the mechanism by which a bag 12 placed into the bag holder subassembly 406 may be moved into contact with the device/vial subassembly 349 placed in the device/vial subassembly holder 408.

Figure 49:
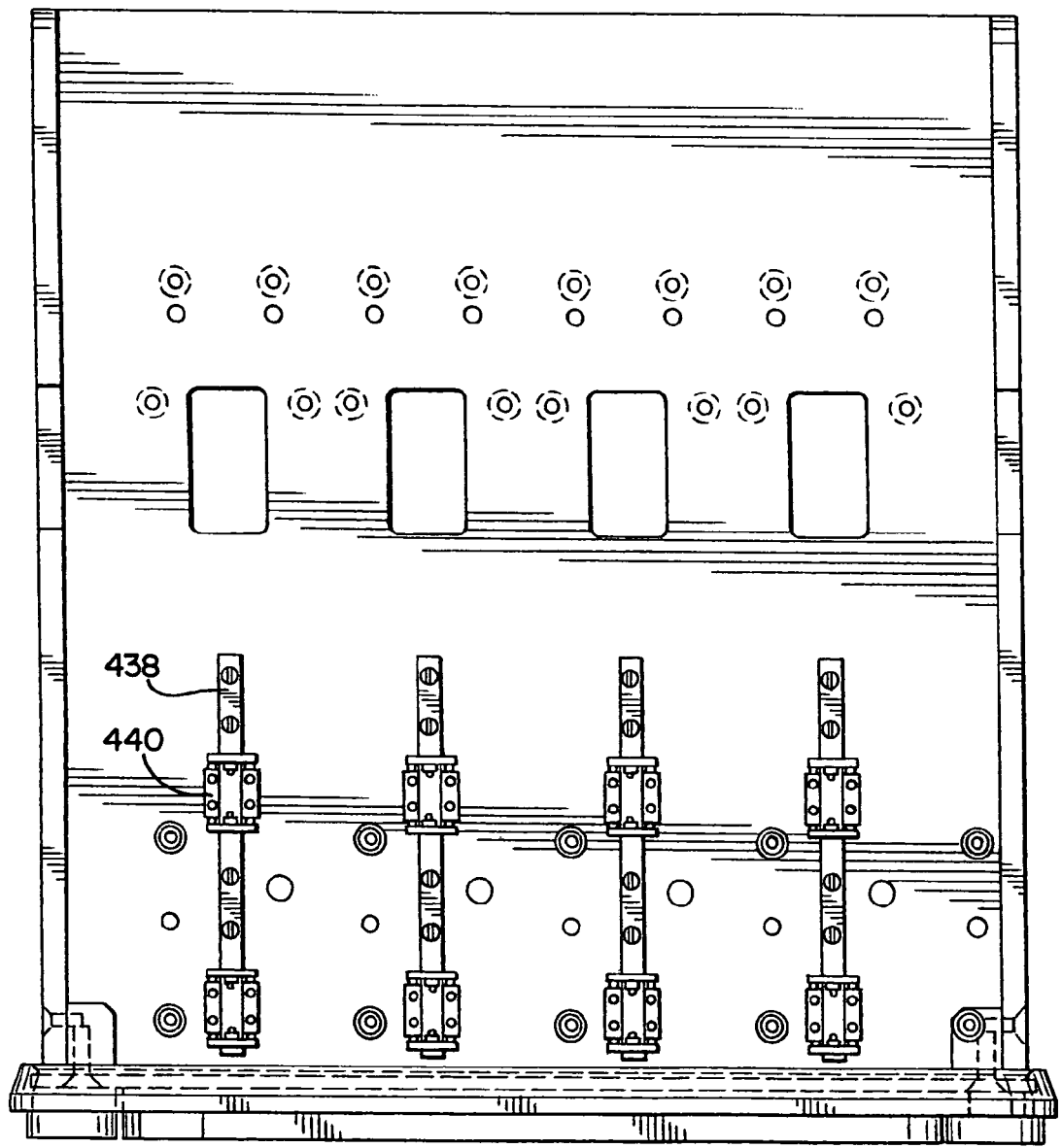
FIG. 49 is front elevation view of the second positioning assembly according to one embodiment of the present invention.
Figure 50:
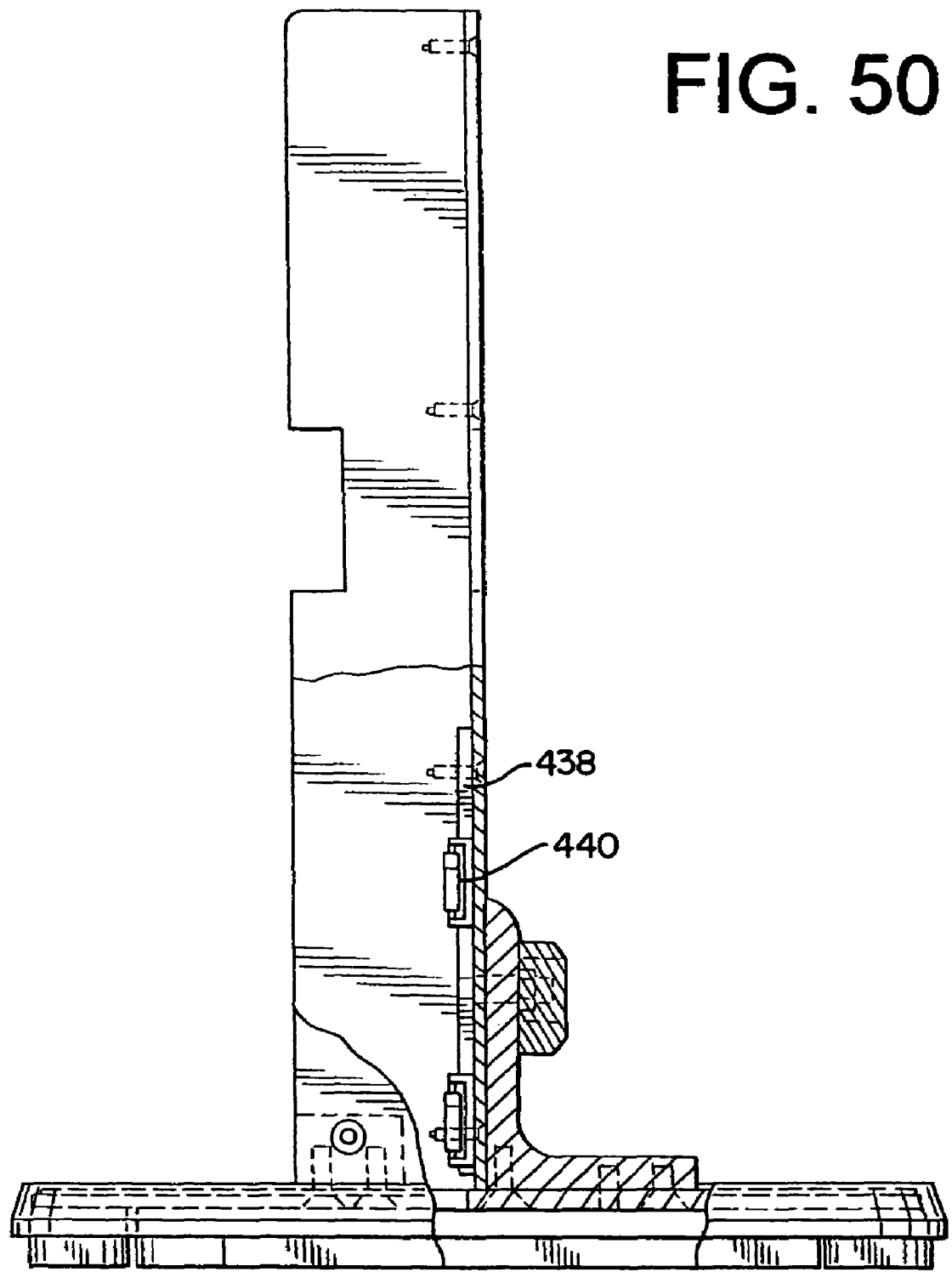
FIG. 50 is a side elevation view of the second positioning assembly of FIG. 49.

As shown in FIGS. 49 and 50, the bag back support plate 436 generally includes a slide rail 438 and slide blocks 440 as shown in a disassembled bag pallet 402. The slide rail 438 is generally secured to the frame 424. The slide blocks 440 ride along the slide rail 438, preferably on ball bearings, and are fixedly attached to the bag back support plate 436. As further shown in FIG. 45, proximate to the bottom of the bag back support plate 436, a bag support foot 442 is generally mounted to the bag back support plates 436. Bumpers are generally secured to the bottom of each of the bag back support plates 436.

The frame 424 is preferably fixed to the pallet base 404. The frame 424 generally includes a rear shielding plate 426 and side shielding plates 428 which extend upwards from the base 404. The rear shielding plate 426 and side shielding plates 428 are generally constructed of steel having sufficient thickness to shield the vial 14 and bag 12 from radiation and excessive heat. The bag pallet 402 generally is arranged to either on its own, or in cooperation with shielding components of a sterilization booth, shield the bag 12 and vial 14 in order to preserve the efficacy of the drugs or diluents typically stored therein. Exposure to radiation or other sterilizing effects can damage the safety and efficacy of many of the drugs typically stored in these containers.

The rear shielding plate 426 preferably includes a window 434. The window 434 is generally simply an opening in the rear shielding plate 426. The bag holder subassembly 406 is generally mounted to the rear shielding plate 426. In the preferred embodiment, the bag pallet 402 allows for the mounting of four bag holder subassemblies 406 to the rear shielding plate 426 and four corresponding device and vial subassembly holders 408.

Similar to the vial pallet 90, the bag pallet 402 may also be equipped with a dosimeter assembly for the purpose of sterility verification. The dosimeter assembly is positioned on the bag pallet 402 to allow for the routine monitoring of dose in the sterile connection between the reconstitution device/vial subassembly 349 and the bag 12. The dosimeter assembly provides feedback to assure that a sterile connection has been achieved as will be described in greater detail below. The dosimeter assembly is also described in greater detail in commonly-owned U.S. application Ser. No. 10/745, 466, entitled "Method And Apparatus For Validation Of Sterilization Process," filed concurrently herewith, which application has previously been incorporated by reference and made a part hereof.

Bag Pallet Transport Assembly 444

The bag pallet 402 is generally supported on, and conveyed through the second cell 25 by the use of a bag pallet transport assembly 444, or bag pallet conveyor 444. The bag pallet conveyor 444 is generally similar to the vial pallet transport assembly 90 of the first cell 23 in its component parts. It preferably includes a powered conveyor 446. The powered conveyor 446 generally includes multiple sections of conveyor which include belts and drive units.

In addition to a powered conveyor 446, the bag pallet transport assembly 444 preferably includes additional components such as cross-transfers, lift and rotate units, lift and locate units and lift gates positioned as necessary to transport the bag pallet 402 through the system. The specific position of these components may be adjusted as necessary to move and position the bag pallet 402 as required. The specific application of these components within a pallet transport assembly is understood by those of ordinary skill in the art.

The bag pallet transport assembly 444 transports the bag pallet 402 between various component loading and unloading stations. These generally include a bag loading position, a palletize device/vial subassembly position, a nozzle blow-off position, a connecting position, and a depalletize reconstitution assembly position. Proximate to these stations and at various other queue positions along the powered conveyor 446 are soft-stop units for locating and positioning the bag pallets 402 as they proceed through the system 21. The position and specific function of each of these soft-stop units will be described in further detail when the operation of the system is described below.

Palletize Device/Vial Subassembly Module 448

Figure 51:
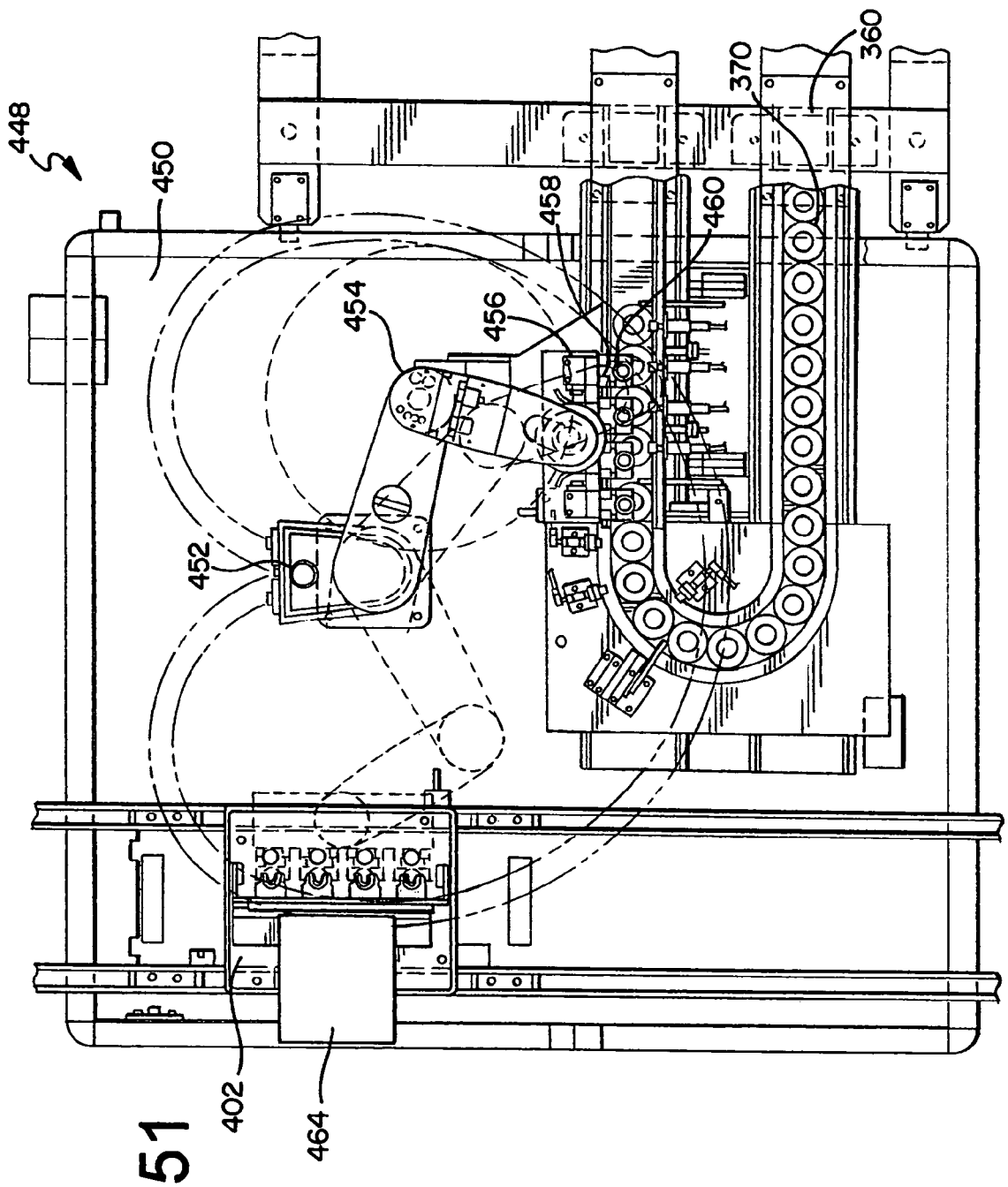
FIG. 51 is a plan view of a palletizing device and vial sub-assembly according to one embodiment of the present invention.

The palletize device/vial subassembly module 448 generally loads the reconstitution device/vial subassemblies 349 onto the bag pallets 402 as shown in FIG. 51. The palletize device/vial subassembly module 448 generally includes a transfer robot 454 and a pallet release mechanism 464. These components are generally mounted on a station base table 450.

The transfer robot 452 generally includes a robot arm 454 and end of arm tooling 456. The transfer robot 454 is generally positioned proximate to the shrinkband applicator station 360 which generally includes the power and free puck conveyor 368. A puck stop and locate assembly 462 generally positions the pucks 370 on the power and free puck conveyor 360 to allow the transfer robot 454 to remove the device/vial subassemblies 349, now with shrinkband applied, from the pucks 370.

The end of arm tooling 456 of the transfer robot 452 preferably includes grippers 458 for grasping the device/vial subassemblies 349. The end of arm tooling 456 preferably includes four grippers 458 on a single support 460 for the simultaneous loading of four device and vial subassemblies 349. Actuators preferably control the positioning of the grippers 458 and the opening and closing of the grippers 458.

Figure 52:
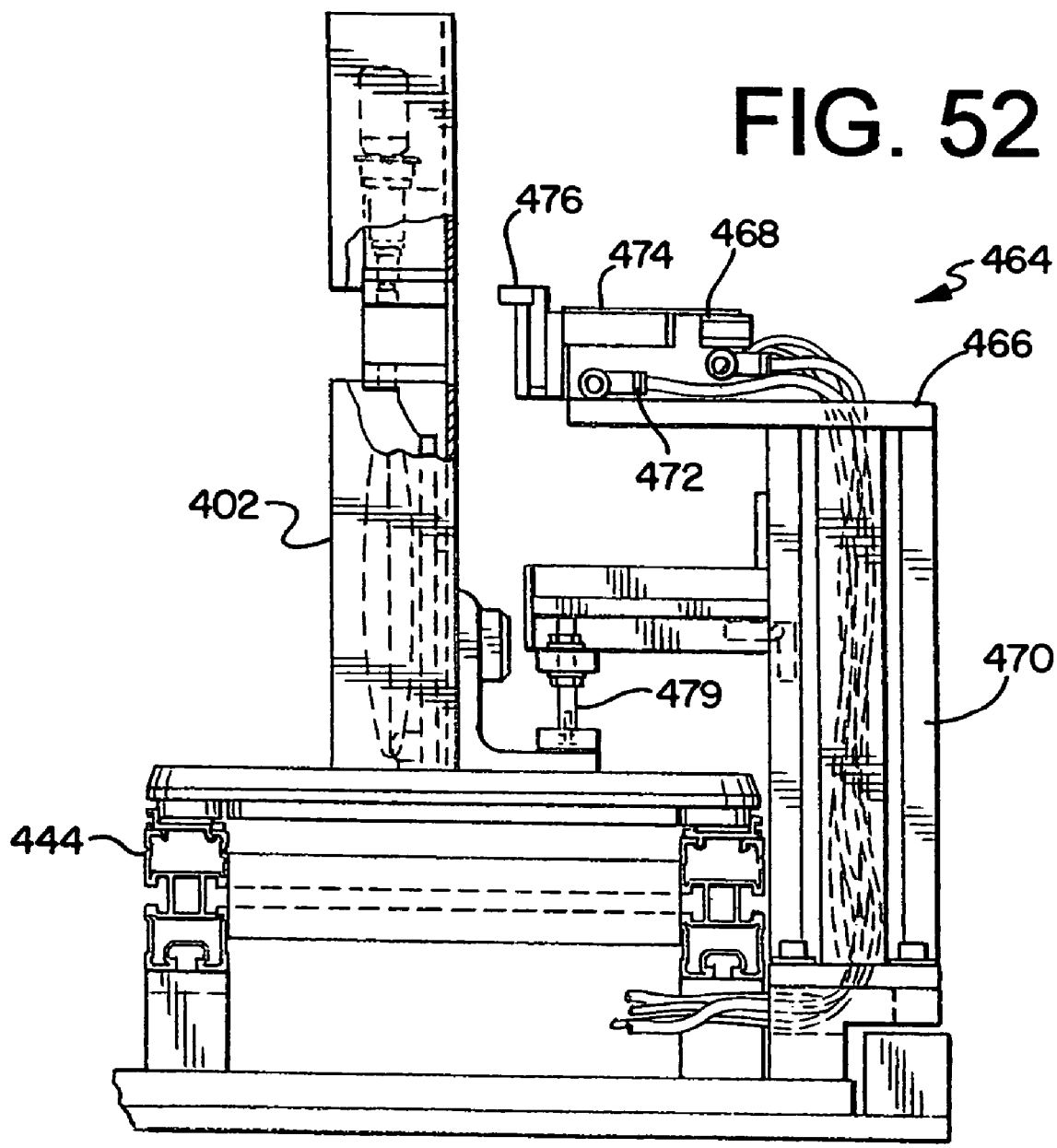
FIG. 52 is a side elevation view of a pallet release mechanism according to one embodiment of the present invention.

The pallet release mechanism 464 of the palletize device/vial subassembly module 448 generally opens the device/vial subassembly holder 408 on the bag pallet 402. The pallet release mechanism 464 is shown in FIG. 52. It preferably includes a positioning mechanism 466, a release tool 468 and a bag pallet clamp 479. The bag pallet claim 479 clamps down on the bag pallet 402 and prevents it from moving off of the bag pallet conveyor assembly 444.

The positioning mechanism 466 generally includes a support 470 and a bag pallet sensor 472. The release tool 468 generally includes an extendable cylinder 474 and a pushing member 476. The extendable cylinder 474 preferably includes a pneumatic actuator which causes the extendable cylinder 474 to extend, placing the pushing member 476 into the gripper 410 of the device and vial subassembly holder 408, opening the gripper 410 as shown in FIG. 48. The transfer robot 452 then preferably loads the device/vial subassembly 349 onto the bag pallet 402. Station guarding is generally provided to shield moving parts of the palletize device and vial subassembly station 448.

Bag Load Module 478

As shown in FIG. 3, bags 12 are generally loaded onto the bag pallet 402 at the bag load module 478. The bag load module 478 generally includes a pallet loader 479, a bag-offload station 480, a label application conveyor 482 and a bag transfer conveyor 486.

Preferably, the bag load station 478 includes two pallet loaders 479, each of which generally includes a pneumatically driven bag pallet opener 488. The bag pallet opener 488 generally opens the bag holder 406 of the bag pallet 402 to allow loading of the bags 12. The bag pallet opener 488 is generally similar to the pallet release mechanism 464 for opening the device/vial subassembly holder 408 on the bag pallet 402 as shown in FIG. 52. One difference is generally in the positioning of the release tool, which is adjusted to open the bag gripper 496 rather than the device gripper 410.

The pallet loaders 479 preferably utilize operators to manually load the bags 12 onto the bag pallet 402. Other embodiments may replace the operator with an automated pallet loader, which generally includes a robot which places the bags onto the bag pallet after it has been opened by the bag pallet opener. It is understood that the bag 12 preferably is loaded with the port connector assembly of the device 10 pre-connected to the bag 12. As will be shown, the port connector assembly of the device 10 is attached to the sleeve assembly of the vial/device subassembly 349.

The bag-offload station 480 generally is supplied bags 12 from a label application conveyor 482. The bags 12 may be labeled with a variety of different identification labels, including bar code, RFID or other types of identifying indicia. The label application conveyor 482 moves labeled bags 12 to a pick and place unit 484. The pick and place unit 484 preferably includes a vacuum tooling used to grip the bags 12. The pick and place unit 484 transfers the bags to the bag transfer conveyor 486. The bag transfer conveyor 486 is preferably a chain link conveyor. The bags 16 then move along the bag transfer conveyor 486 to the pallet loaders 479.

Nozzle Blow-Off Module 500

Figure 53:
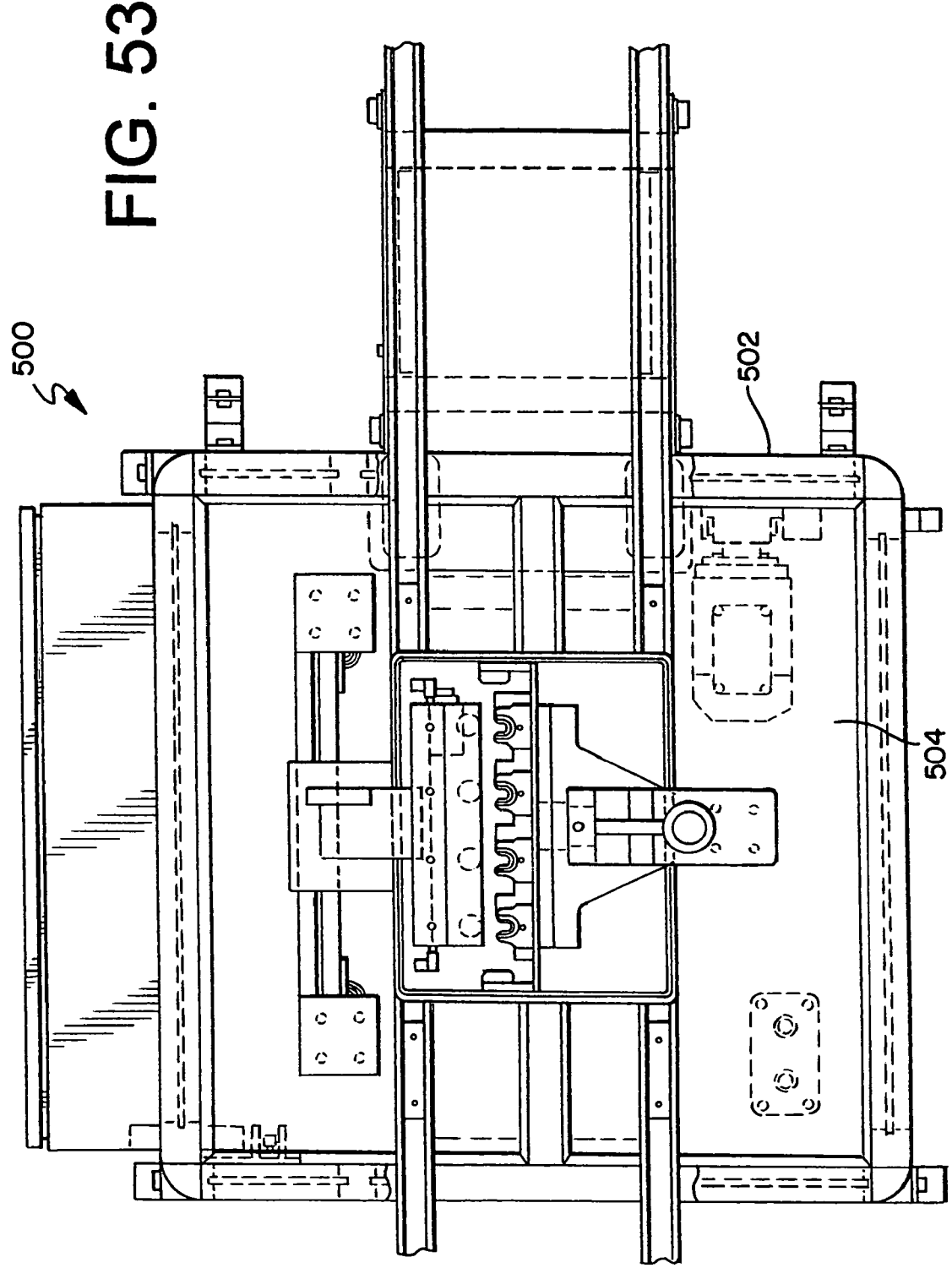
FIG. 53 is a plan view of a nozzle blow off station according to one embodiment of the present invention.
Figure 54:
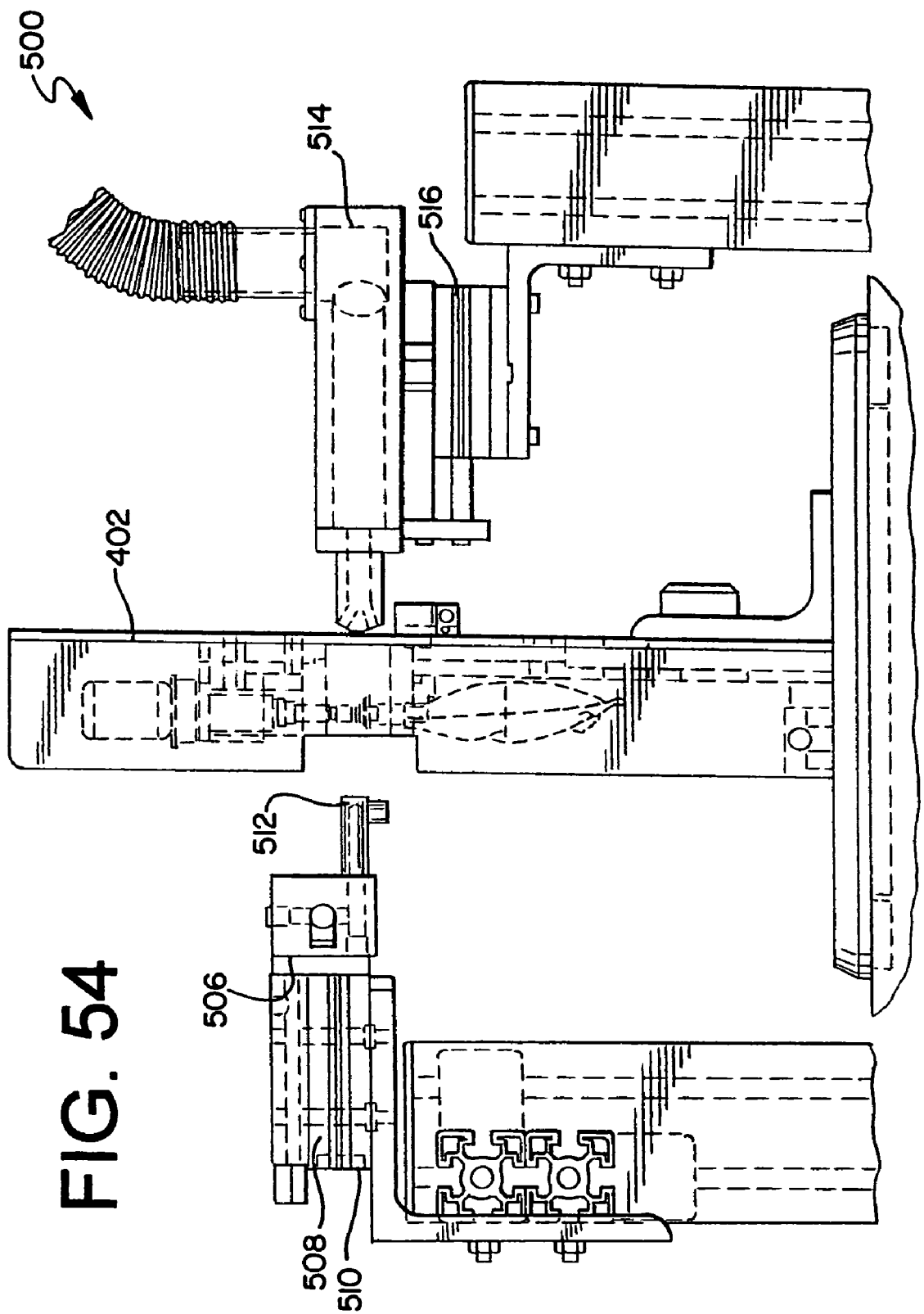
FIG. 54 is a partial side view of the nozzle blow off station of FIG. 53.

The loaded bag pallet 402 generally proceeds along the bag pallet conveyor assembly 444 to a nozzle blow-off module 500, as shown in FIGS. 53-54. The nozzle blow-off module 500 removes any water droplets or particulate contaminants from a port connector 30 of the bag 12, and optionally also from the reconstitution device 10. The nozzle blow-off module 500 generally includes a housing 502 and a blower assembly 506.

The housing 502 generally includes a base table assembly 504 and a shield cover. The base table assembly 504 generally supports the other components of the nozzle blow-off module 500 and positions them generally level with the bag pallet 402 as it is conveyed by the bag pallet conveyor 444. The shield cover is generally a plastic cover which surrounds the other components of the nozzle blow-off module 500. The shield cover is generally supported on the base table assembly 504.

The blower 506 is preferably contained within the housing 502. The blower assembly 506 generally includes a blower 508 and a vacuum 514. The blower 508 is supported on a movable automated support 510. The automated support 510 generally includes an actuator which positions the blower 508 proximate to the bag 12, which is supported on the bag pallet 402 as shown in FIG. 54. The blower 506 preferably includes four nozzles 512 to correspond to the four bags 12 which are generally positioned in the bag pallet 402. The actuator is preferably a pneumatic actuator.

The vacuum 514 of the blower assembly 506 is also preferably supported on a movable automated support 516 having an actuator which moves the vacuum 514 proximate to the bag pallet 402 such that the bag 16 is positioned between the blower nozzle 512 and the vacuum 514. The vacuum automated support 516 actuator is also preferably a pneumatic actuator.

Bag/Device Subassembly Sterilization Booth 520

The loaded bag pallet 402 is generally conveyed to the bag/device subassembly sterilization booth 520 as shown in FIGS. 55-58. The bag/device sterilization booth 520 is similar to the previously described vial/device sterilization booth 270. The bag/device sterilization booth 520 generally includes a housing 519, a sterilizing emitter assembly 524, a heat shield 548, and a connecting mechanism 557.

Further, as stated previously, there are different levels of sterilization. Therefore, a discussion on the topic must begin with the selection of a desired sterility assurance level (SAL), a measure of the probability that one unit in a batch will remain non-sterile after being exposed to a specific sterilant. For example, an SAL of $10^{-3}$ means that one device in a thousand may be non-sterile. Selecting the proper SAL may occur during a dose-setting phase of radiation sterilization validation. In many cases, the intended use of the device to be sterilized will dictate the need for a particular SAL. The commonly accepted SAL for invasive medical devices is $10^{-6}$. However, some European countries only recognize $10^{-6}$ SAL for a claim of "sterile." In such cases, the country of intended use will dictate the SAL as much as the device's intended use. It is understood that the sterilization sources are selected according to the desired or required levels of sterility assurance.

The housing 519 of the bag/device sterilization booth 520 is similar to the housing of the vial/device sterilization booth 270. The housing 521 generally shields the external environment from any radiation generated by the sterilizing emitter assembly 524. The housing 519 divides the bag/device sterilization booth 520 into a pre-sterilization chamber 521, a post-sterilization chamber 522, and a sterilization chamber 523. The pre-sterilization chamber 521 and post-sterilization chamber 522 are similar to those of the vial/device sterilization booth 270 previously discussed. The sterilization chamber 523 of the bag/device sterilization booth 520 is different from that of the vial/device sterilization booth 270, and is described in detail below. Each of the chambers preferably includes its own individual conveyor 565. The bag/device sterilization booth 520 conveyors 565 are similar to those previously described in conjunction with the vial/device sterilization booth 270. The conveyors 565 can be considered as part of the bag pallet conveyor 444. The bag/device sterilization booth 520 also generally includes doors which are similar to those of the vial/device sterilization booth 270.

The sterilization chamber 523 is generally arranged to accommodate the bag pallet 402 which is a second positioning assembly for properly positioning the bag 12 and reconstitution device/vial subassembly 439 for a sterile connection.

The sterilizing emitter assembly 524 generally includes a bag pallet shielding 525 and an e-beam source, which is preferably a pair of low energy e-beam tubes 527. The e-beam source is generally arranged to provide a sterilizing dose to the bag pallet 402 at a location contemplated for the connecting of the bag 12 and reconstitution device/vial subassembly 439. The location contemplated for the connecting of the bag 12 and the reconstitution device/vial subassembly 439 is the connection area. The e-beam tubes 527 preferably continuously emit, and the bag pallet shielding 525 generally shields the bag pallet 402 and the associated bag 12 and reconstitution device/vial subassembly 349 from undesired exposure.

The e-beam tubes 527 are generally two oppositely positioned low-energy e-beam tubes 527. The preferred e-beam tubes 527 are generally similar to those used in conjunction with the viaudevice sterilization booth 270. The e-beam tubes 527 are preferably positioned in tube holders 528. The tube holders 528 position the e-beam tubes such that an electron cloud or sterilizing field may be formed within the connection area of the sterilization chamber 522. While two e-beam tubes are the preferred arrangement, other arrangements can be used while achieving the same beneficial results as described in conjunction with the vial/device sterilization booth 270.

Figure 56:
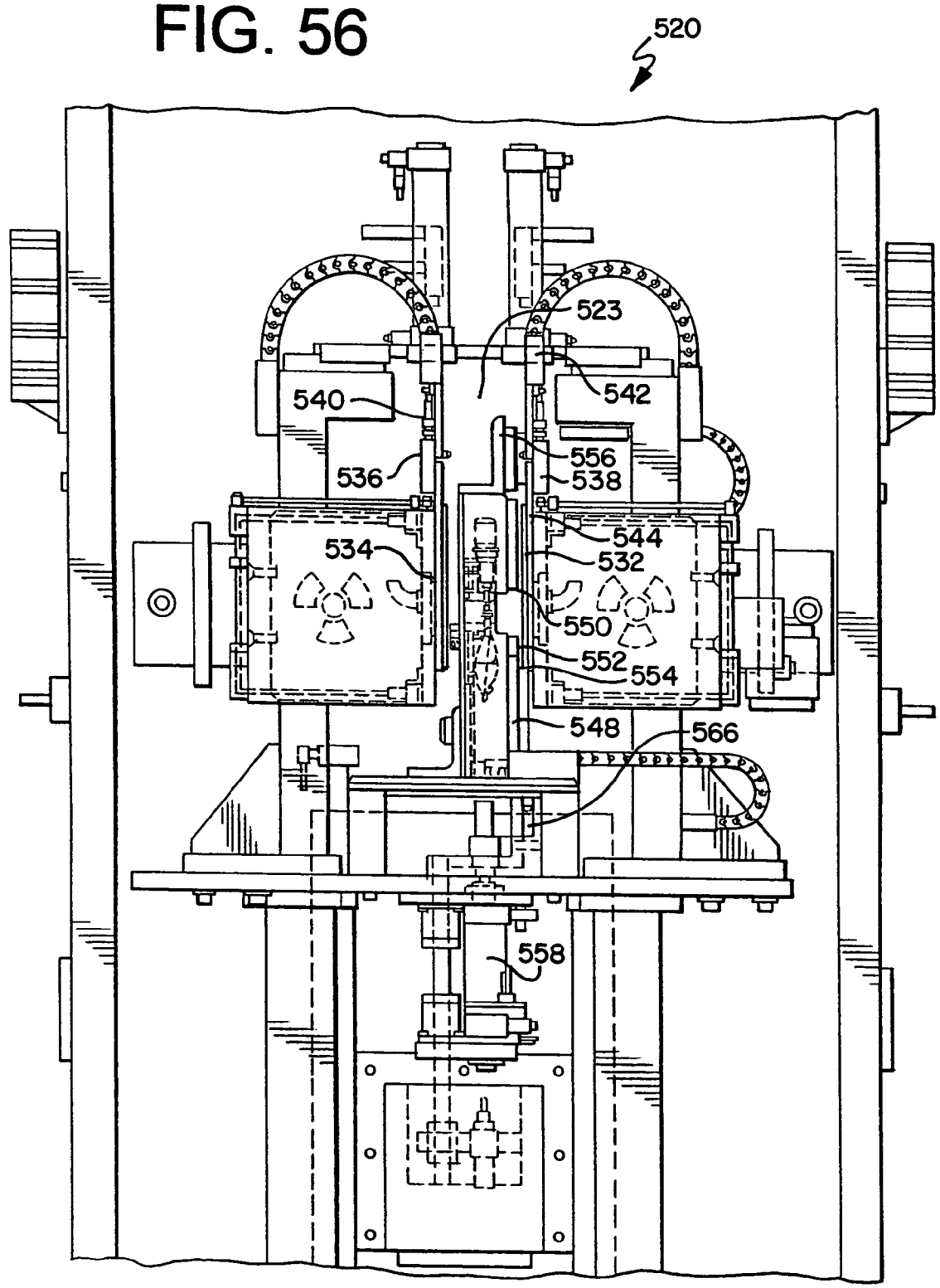
FIG. 56 is a partial side view of the second sterilization chamber of FIG. 55.
Figure 57:
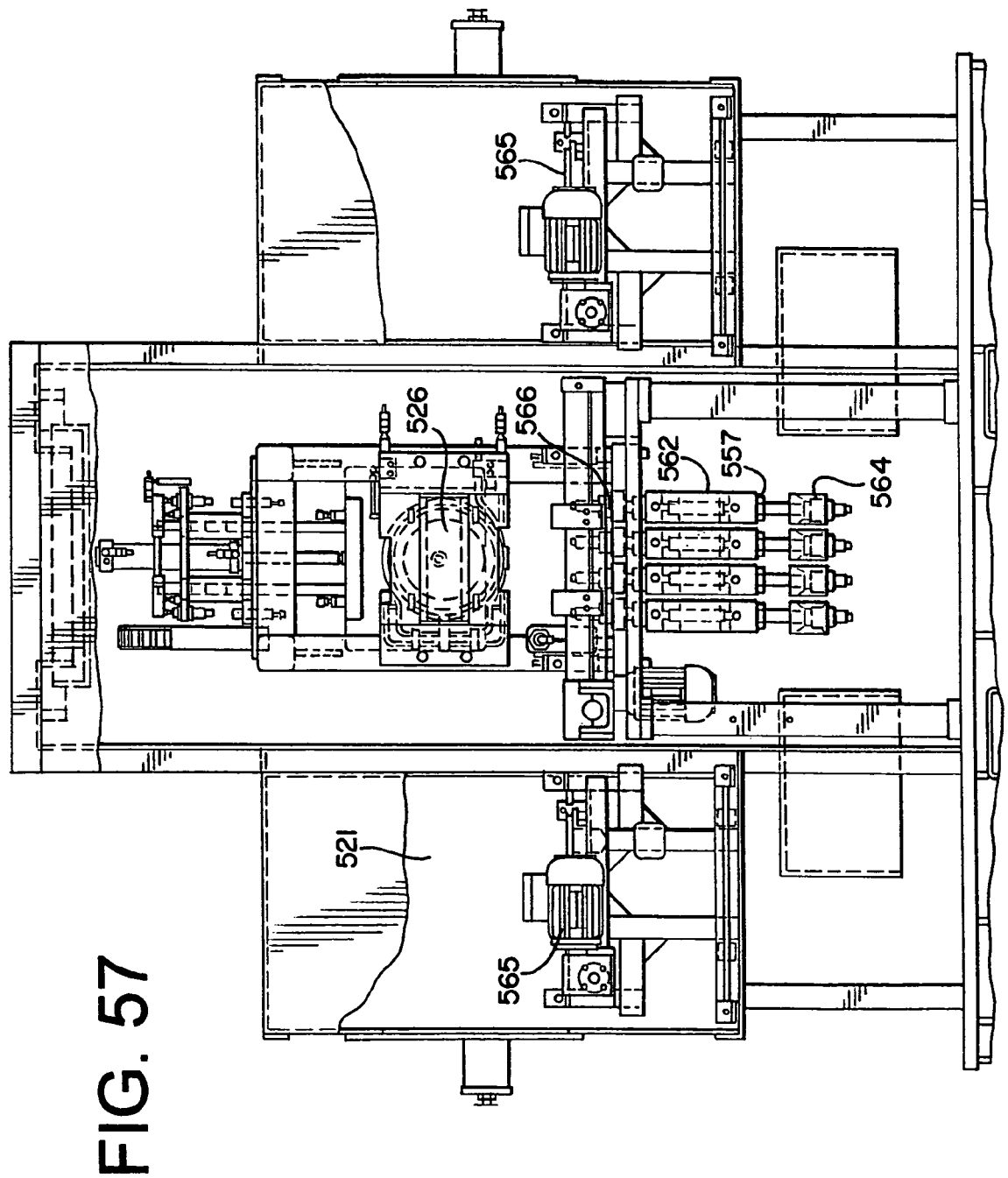
FIG. 57 is a front cross-sectional view of the second sterilization chamber of FIG. 55.
Figure 58:
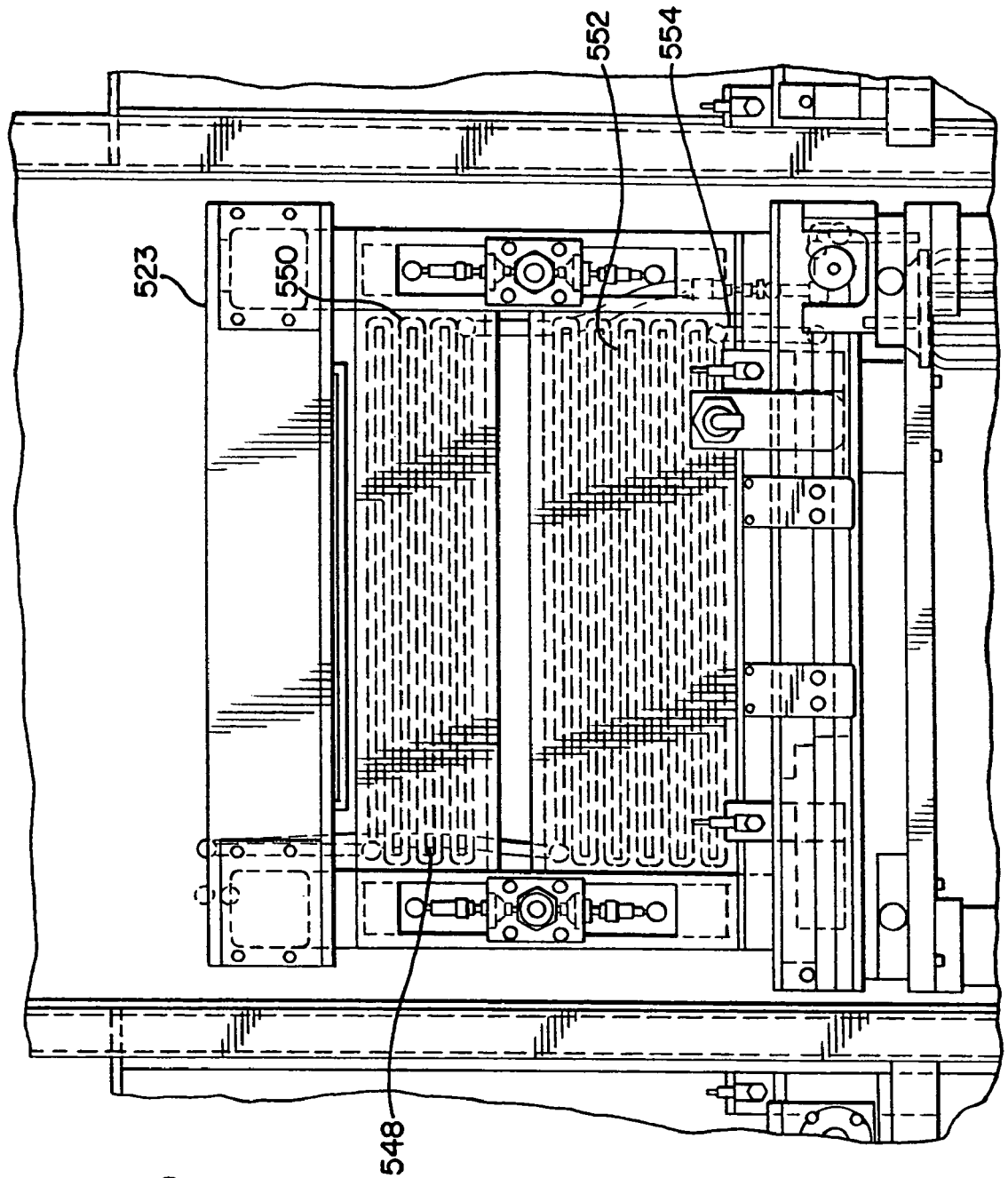
FIG. 58 is a partial front cross-sectional view of the second sterilization chamber of FIG. 55.

FIGS. 55-56 show the sterilization chamber 522 with a bag pallet 402 positioned in the chamber. The e-beam tubes 527 are preferably positioned on two sides of the sterilization chamber 522.

The bag pallet shielding 525 generally comprises shutters 532,534. The shutters 532, 534 are generally mounted on shutter support structures 536,538. The shutters 532,534 generally include actuators 540, 542 which generally slide the shutters 536, 538 upward on demand. The shutters 536, 538 block the e-beam radiation from reaching the sterilization chamber 522 until they are moved upwards, preferably exposing a positioning assembly, such as the bag pallet 402, to the e-beam radiation. The actuators 540,542 are preferably pneumatic cylinders. The shutters 536,538 preferably include coolant ports 544 which provide a flow of a coolant through the shutters 536,538.

The bag/device subassembly sterilization booth 520 preferably also includes a heat shield 548. The heat shield 548 generally includes an upper plate 550 and a lower plate 552. The plates 550, 552 generally include cooling ports 554, and are cooled by coolant flowing through the heat shield. The coolant preferably travels through the heat shield plates in a boustrophedonic pattern.

The heat shield 548 is generally sized to cooperatively engage the bag pallet 402 to protect the bag 12 and vial 14 contained in the bag pallet. The rear and sides of the bag pallet 402 are protected by the rear plates 426 and the side plates 428. The top portion and front portion are exposed until the bag pallet 402 enters the sterilization chamber 522. In the sterilization chamber 522 the front of the bag pallet 402 is shielded by the heat shield 548. The top of the bag pallet 402 is generally shielded by a shielding bracket 556 in the sterilization chamber 522. The shielding bracket 556 is preferably moved into a shielding position by an actuator after the bag pallet 402 is positioned in the sterilization chamber 522. In this manner, the bag pallet and sterilization booth 520 work cooperatively to shield those parts of the containers that should be shielded while exposing those parts that are contemplated for connection within a sterile field.

The lower plate 552 of the heat shield is preferably movable vertically during the sterile connecting process. The lower plate 522 is generally pushed upwards by a connecting mechanism 557 when the bag 16 and device 12 are connected.

The connecting mechanism 557 generally includes a snap closure mechanism 558. The snap closure mechanism 558 is generally mounted to a base plate 560 underneath the sterilization chamber 522. The snap-closure mechanism 558 preferably includes four independent pneumatic cylinders 562. The pneumatic cylinders 562 preferably include electronic position feedback sensors 564. Additionally, extending members 566 are generally attached to the pneumatic cylinders 562, and move in conjunction with the pneumatic cylinders 562. The extending members 566 generally contact the lower plate 552 of the heat shield 548 and move it upward when the pneumatic cylinder 562 is actuated.

Locking Clip Placement Module 688

Figure 65:
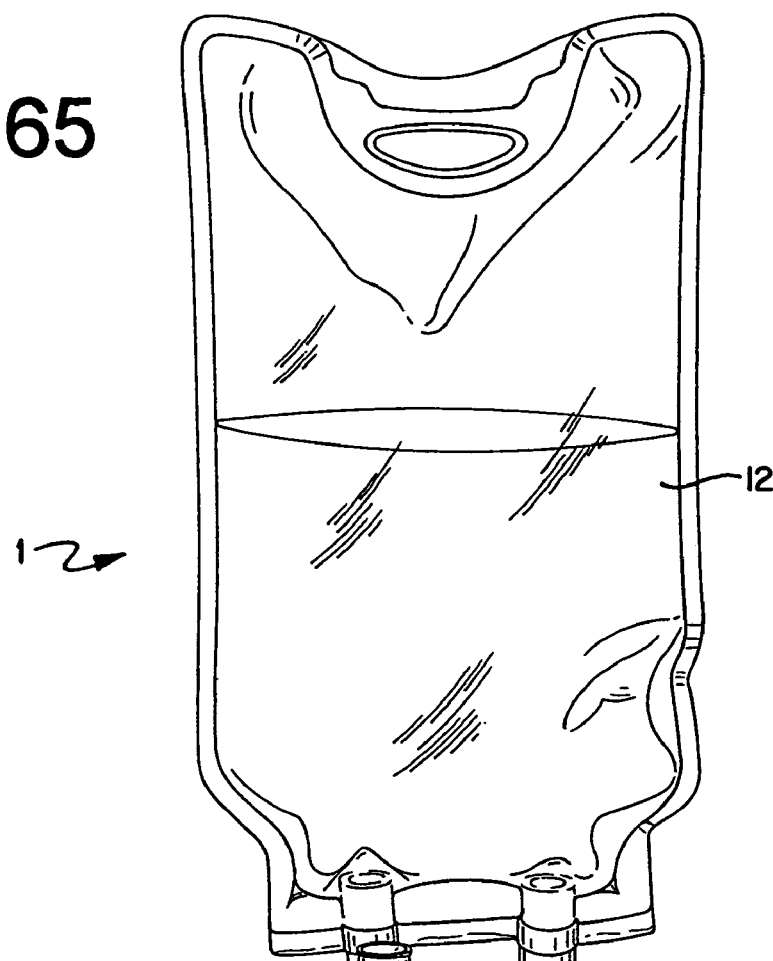
FIG. 65 is a perspective view of another embodiment of a reconstitution assembly according to the present invention.
Figure 66:
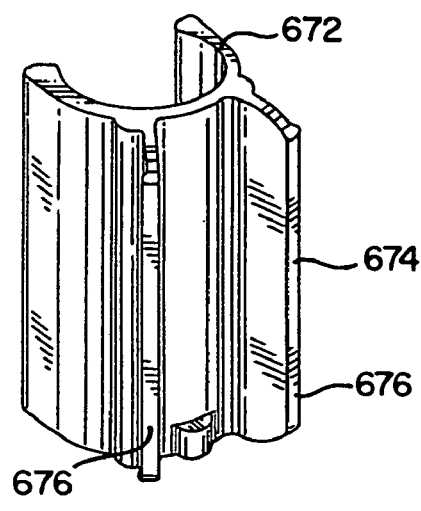
FIG. 66 is a perspective view of a locking device for use in conjunction with the reconstitution assembly shown in FIG. 65.

As shown in FIGS. 2A, 65, and 66, in certain embodiments of the invention it may be desirable to place a locking device 670 onto the reconstitution device assembly 1. In the preferred embodiment the locking device is a clip. Such a clip is shown in detail in FIG. 66, and is described in further detail in commonly-owned U.S. application Ser. No. 10/746, 238, entitled "Sliding Reconstitution Device For a Diluent Container," filed concurrently herewith, the contents of which have previously been incorporated by reference into this specification.

As shown in FIG. 65, the locking device 670 generally functions as a means for preventing the premature activation of the reconstitution device 10 by restricting the relative movement of the sleeves of the reconstitution device.

The locking device 670 of FIG. 66 generally includes a securing portion 672 and a gripping portion 674. The securing portion 672 is that portion of the locking device 670 which attaches to the reconstitution device 10. The securing portion 672 preferably extends about a portion of a first sleeve 32 (FIG. 2A). The securing portion 672 generally comprises a penannular cylinder having a radius generally equal to the radius of the exterior of the first sleeve 32. The penannular cylinder has an opening sized to allow the first sleeve 32 to be snapped into and out of the penannular cylinder.

The gripping portion 674, shown in FIG. 66, facilitates the securing and removal of the locking device 670 onto, or off of, the first sleeve 32. The gripping portion generally includes two fins 676 which may be grasped simultaneously by a person using the thumb and forefinger of a single hand. The fins 676 preferably extend at an angle away from one another from where they are joined to a base portion of the locking device 670.

The locking device 670 structure operates to maintain the sleeves in an axially fixed relative position. The locking device 670 has a portion that abuts the second sleeve 34 of the reconstitution device 10 and another portion that abuts a structure associated with the first sleeve 32, or the first container 12. Generally the locking device 602 abuts a flange of the port connector assembly 30 of the first container 12. The other end of the locking device 670 abuts an end, or end flange of the second sleeve 34, when the locking device 670 is secured to the reconstitution device 10. Thus, the locking device 670 prevents the first sleeve 32 and the second sleeve 34 of the reconstitution device 10 from relative axial movement.

The locking device 670 is generally pushed onto the reconstitution device 10 at an optional locking clip placement module 688, as shown in FIG. 3. The locking clip placement module 688, when used, is preferably automated, but may simply position the reconstitution device assembly 1 such that the locking clip 670 may be positioned on the reconstitution device assembly 1 manually.

Depalletize Reconstitution Assembly Module 568

Figure 59:
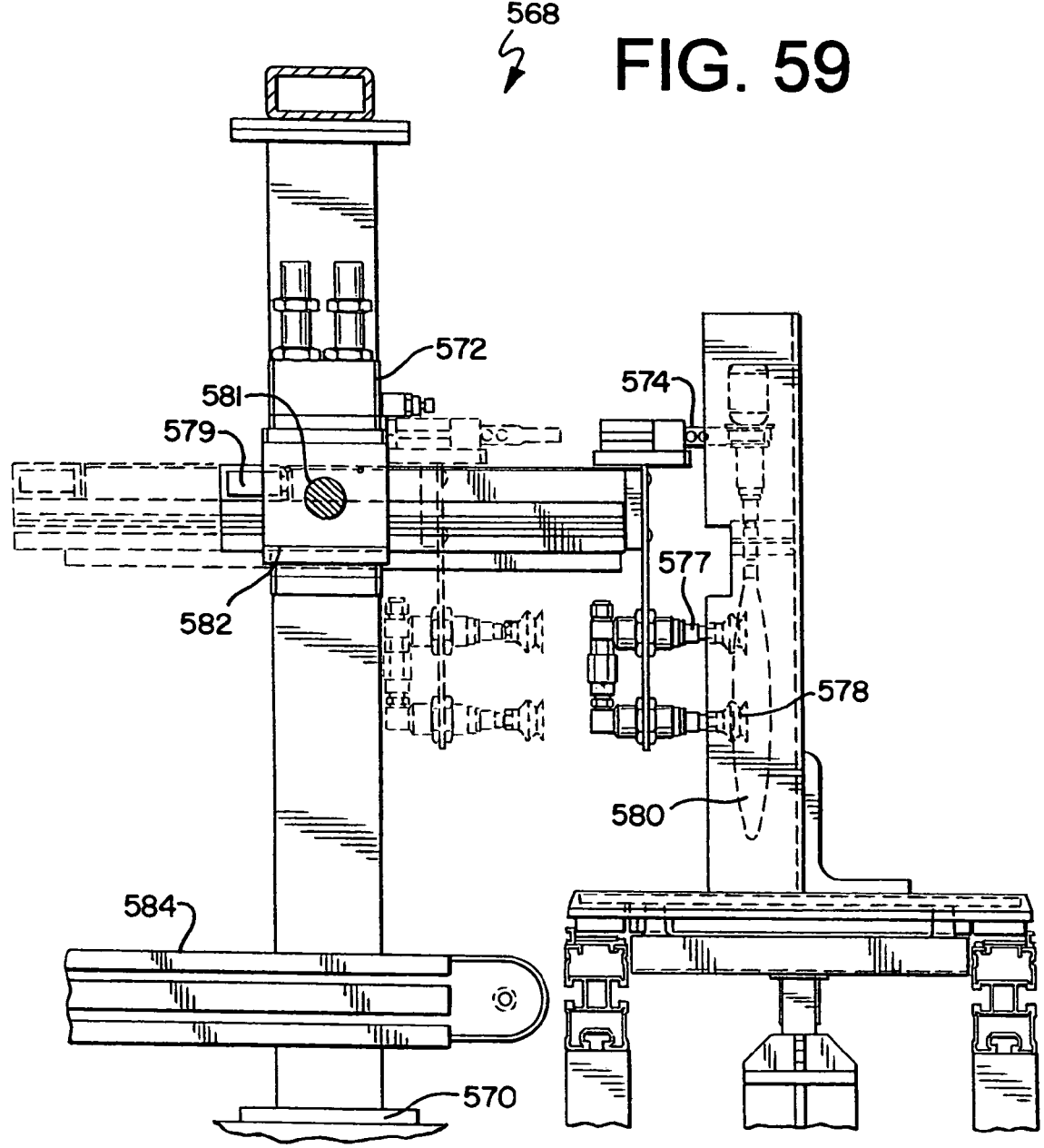
FIG. 59 is a partial side view of a depalletizing reconstitution device assembly according to one embodiment of the present invention.
Figure 60:
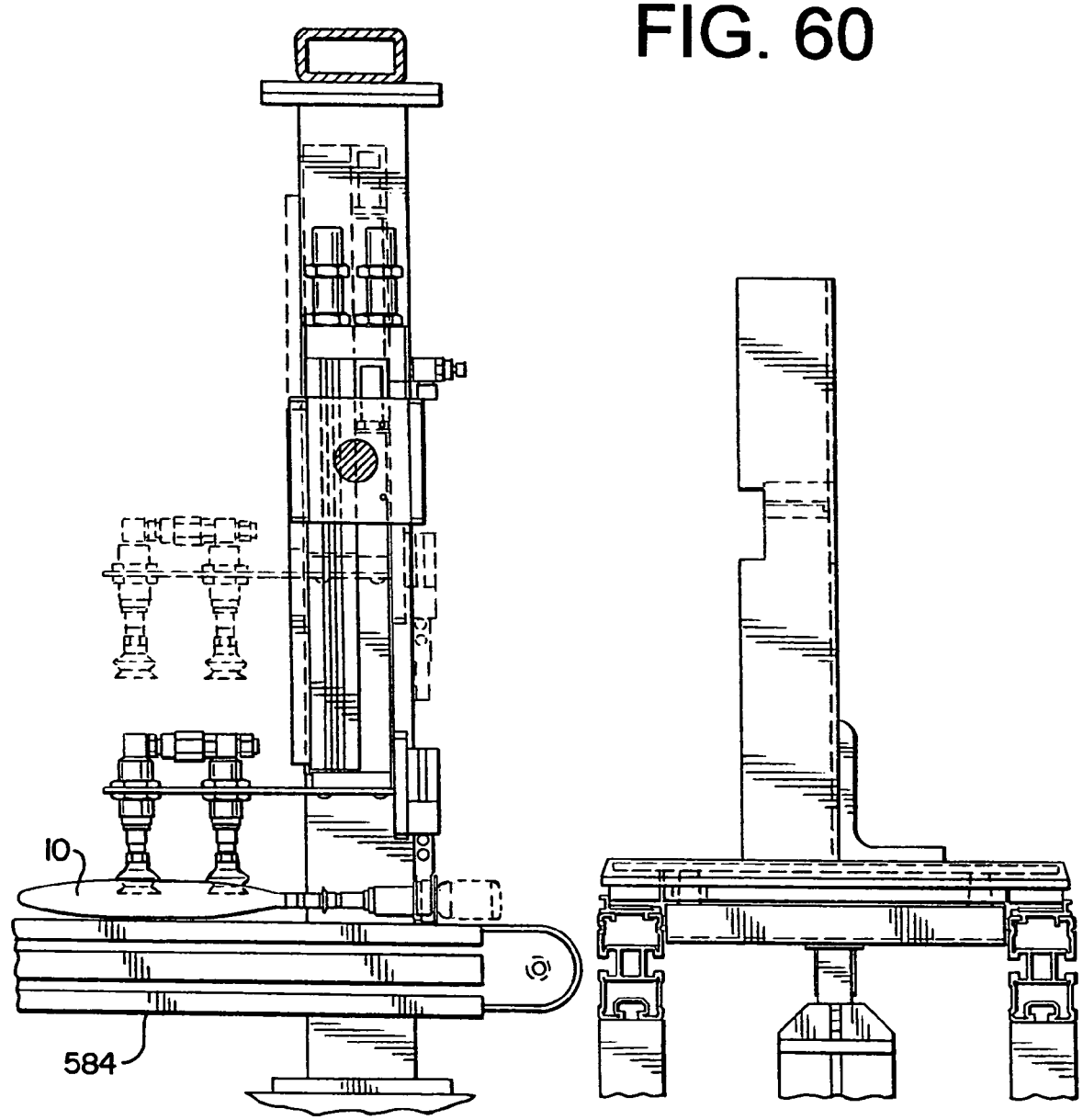
FIG. 60 is a side view of the depalletizing reconstitution device assembly of FIG. 59.

After the bag 12 and reconstitution device/vial subassembly 349 have been sterilely connected to form a reconstitution assembly 1, the bag pallet 402 is preferably conveyed out of the sterilization booth 520 to a depalletize reconstitution assembly module 568 as shown in FIGS. 3, 59 and 60. The depalletize reconstitution assembly module 568 unloads the reconstitution assemblies 1, and generally includes a station base table assembly 570, pick and place assembly 572 and a pallet release mechanism 573. The pick and place assembly 572 and pallet release mechanism 573 are preferably mounted to the station base table assembly 570.

The pick and place assembly 572 preferably includes a device gripper 574 and a bag gripper 576. The device gripper 574 is generally a pneumatic gripper sized to grip the reconstitution device 10.

The bag gripper 576 preferably includes suction cups 578 through which a vacuum is applied to a bag surface 580 securing the bag 16 to the suction cups 578 as shown in FIG. 59. Vacuum lines 577 provide the vacuum at the openings of the suction cups 578.

The device gripper 574 and bag gripper 576 are preferably mounted on a dual actuator support 582 having a linear actuator 579 and a rotational actuator 581.

The depalletize reconstitution assembly module 568 also includes a pallet release mechanism for opening the grippers of the bag pallet. A pallet release mechanism has been described in conjunction with the palletize device/vial subassembly module 448 and with the bag load station 478. The pallet release mechanism here is similar, but adds an additional set of release tools such that the device grippers and bag grippers may be opened simultaneously. The offloaded reconstitution assemblies 1 are generally moved off of the system 21 on a belt conveyor 584.

Operation

Operation of the system 21 for the sterile connection of the reconstitution device 10 and a container 12,14 preferably involves the use of the sterilization booths 270,520. Four sterilization booths, including two vial/device sterilization booths 270 and two bag/device subassembly sterilization type booths 520 operating on parallel tracks, are used in one preferred embodiment depicted in the system 21 shown in FIG. 3. The general operation of the system 21 in assembling and fabricating the reconstitution assembly 1 will now be described.

Operation of the Vial/Device Connection System 23 (First Cell)

Referring to FIGS. 3 and 15-23, the operation of the vial/device connection system 23 is more readily understood. The first module or station of the vial/device connection system 23 is generally the device loader module 94. Preferably, a reconstitution device 10 is loaded onto a vial pallet 27 at this module. The device loader module 94 is preferably automated. Reconstitution devices 10 provided to the device loader module 94 are generally loaded into the vial pallet 27 without operator input.

An empty vial pallet 27 is generally moved into a position at the device loader module 94 on the vial pallet transport assembly 90. Positioning of the vial pallet 27 is generally performed by a soft stop 586 incorporated into the vial pallet transport assembly 90 at the device loader module 94. It is understood that a plurality of vial pallets 27 are loaded onto the vial pallet transport assembly 90.

Figure 15:
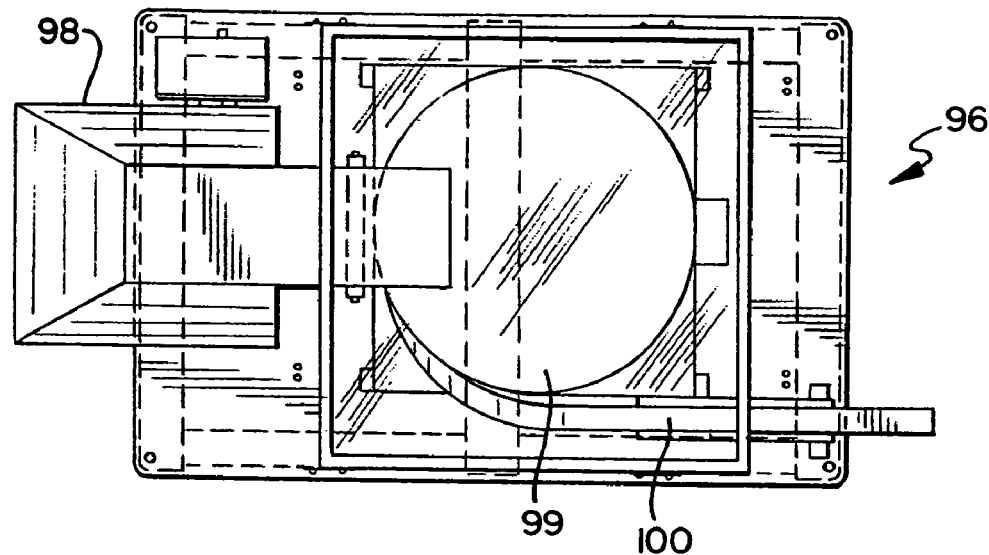
FIG. 15 is a top view of a reconstitution device receiver according to one embodiment of the present invention.
Figure 16:
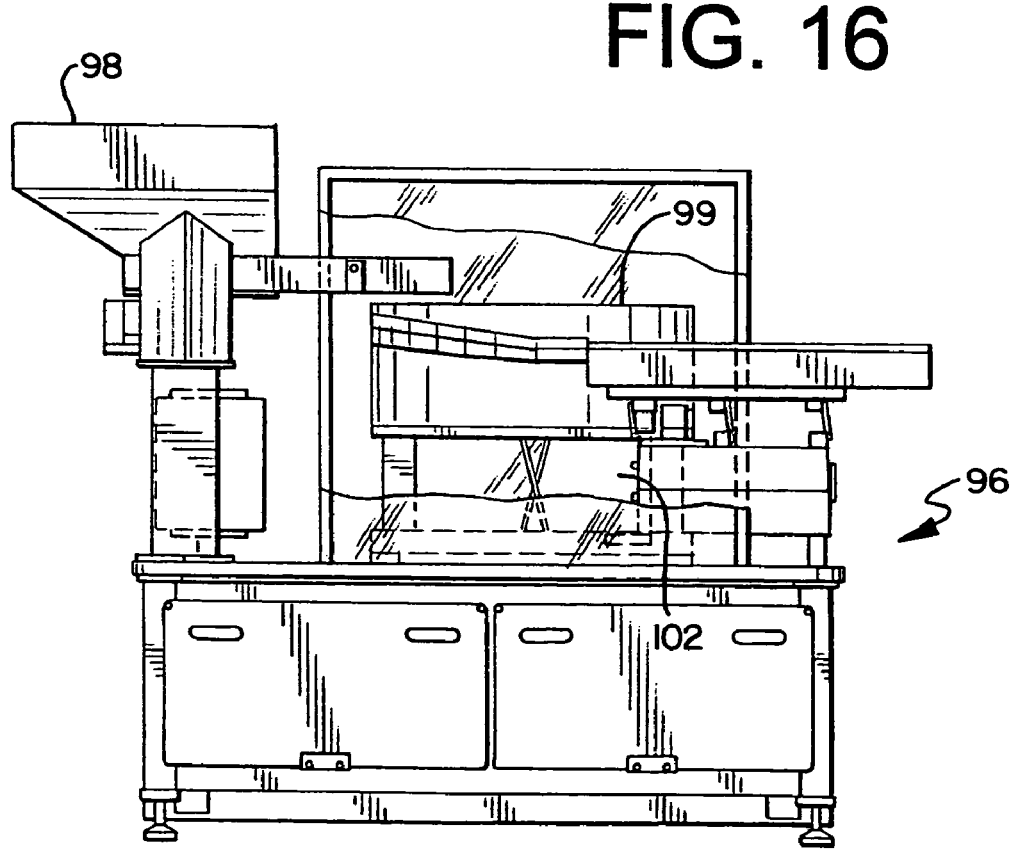
FIG. 16 is a side view of the reconstitution device receiver of FIG. 15.

Reconstitution devices 10 are generally loaded into the vibratory bowl feeder 96 of FIGS. 15-16. From the vibratory bowl feeder 96, the devices 10 are transferred to the rotary dial-index table 104 of FIGS. 17-18 via the discharge chute 100. The devices 10 are rotated by the rotary dial-index table 104 past the inspection system 112 where the devices 10 are inspected for deficiencies. Typical deficiencies that the inspection system 112 is preferably configured to detect include, for example, devices 10 having a defective septum, devices 10 missing a septum, or devices that have been prematurely activated. The reject shucker assembly 118 shucks rejected devices 10 to the reject chute 124.

Figure 23:
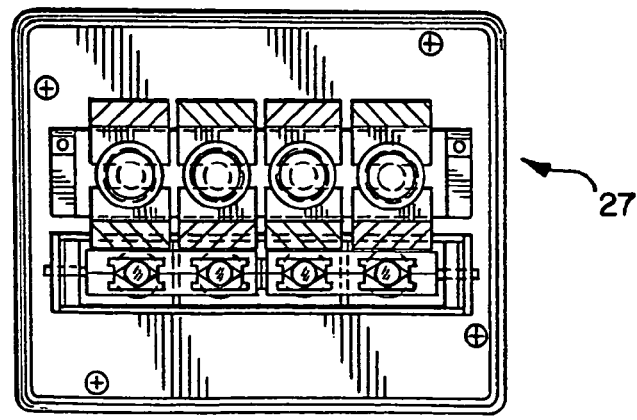
FIG. 23 is a top view of a first positioning assembly being loaded with a reconstitution device according to one embodiment of the present invention.

The rotary dial-index table 104 further rotates acceptable reconstitution devices 10 to the transport tracks 130. The devices 10 are off-loaded to the transport tracks 130 by the device off-load assembly. The reconstitution devices 10 travel down the transport tracks 130 to the device presentation nest 136 as shown in FIGS. 19-23. The device presentation nest 136 is generally a three position pneumatic-actuated assembly. In a first position (A) as shown in FIG. 20, two reconstitution devices 10 are loaded into two of the four device nests 140 from the transport tracks 132. The device presentation nest 136 then generally moves into a second position (B) and two more reconstitution devices 10 are loaded into the two remaining device nests 140 as shown in FIG. 21. The device presentation nest 136 then moves into a third position (C) as shown in FIG. 22. In the third position, the part grippers 152 mounted to the transfer robot 146 pick the four reconstitution devices 10 and remove them from the device presentation nest 136, which then returns to first position (A) to repeat the cycle. The four reconstitution devices 10 are then transferred to the vial pallet 27 as shown in FIGS. 19 and 23.

After the reconstitution devices 10 have been loaded into the vial pallet 27, the vial pallet 27 is conveyed to the second module or station by the vial pallet transport assembly 90. A soft stop 588 positions the vial pallet 27 properly for loading of the vial 14. The second module shown in FIG. 3 is the vial container loader module 154. In other embodiments, the order of the device loader module 94 and the vial container loader module 154 may be reversed.

The vials 14 are generally loaded onto the accumulating conveyor 158 either manually or automatically at the load station 160 as shown in FIG. 24. The vials 14 generally are capped vials with a metal seal crimped to the opening. The vial container loader module 154 is generally automated, and after loading, the vials 14 are preferably inspected, decapped, and automatically placed onto the vial pallet 27 without further operator input.

The vials 14 proceed through the accumulating conveyor 158 until they are positioned, preferably four at a time within the v-block fixture 162, as shown in FIG. 25. The container transfer robot 188 then picks up the four vials 14 from the v-block fixture 162, and moves them to the inspection assembly 192. The vials 14 are inspected and any defective vials 14 are rejected and removed from the system. Acceptable vials 14 in a batch of four containing a reject vial 14 may be placed back onto the accumulating conveyor 158 and recycled. Where all four vials 14 in a batch are acceptable, the vials 14 are transferred to the uncap mechanism assembly 202, as shown in FIG. 27. Here, the metal seal is removed, the vials 14 are inverted, and then the vial 14 are presented to the pallet load robot 210.

Figure 29:
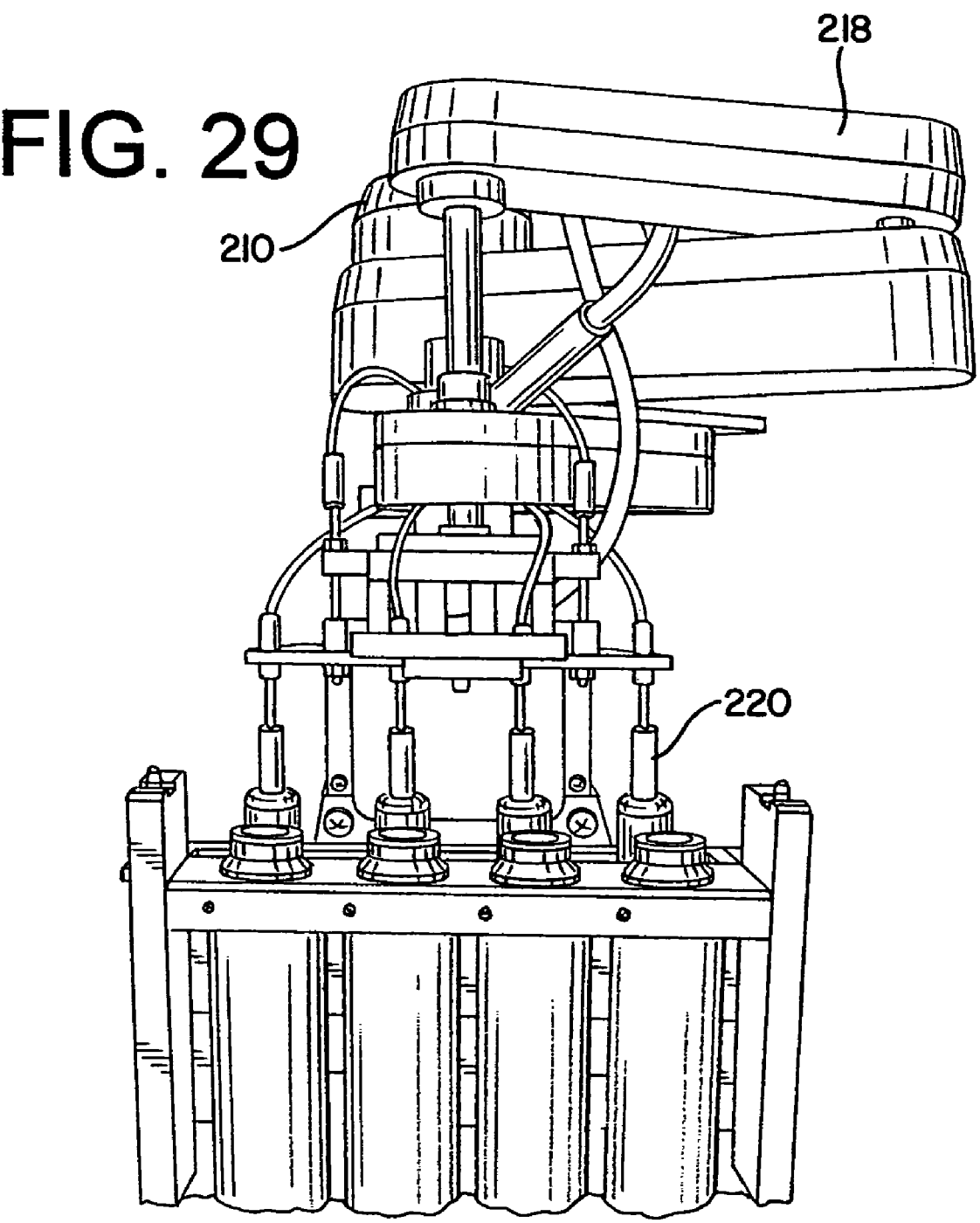
FIG. 29 is a front view of a pallet load robot according to one embodiment of the present invention.

Referring to FIGS. 28 and 29, the pallet load robot 210 generally transfers the batch of four vials 14 to the vial pallet 27. The vial pallet 27 is lifted by the pallet lift 228, shown in FIGS. 33 and 34, and the vial holder 54 portion of the vial pallet 27 is opened by the vial holder release mechanism 230. The pallet load robot 210 then positions the vials 14 within the vial holder 54. Once the vials 14 are positioned in the vial holder 54, the vial holder release mechanism 230 closes the vial holder 54. As discussed, the apparatus 21 can be pre-programmed to control the vertical position at which the vials 14 are loaded and held in the vial holder 54. In one example, the apparatus 21 can be programmed to place and hold the vials 14 at different vertical locations in the vial holder 54 such as if different sized vials 14 are used in separate operational cycles of the apparatus 21. Thus, the apparatus 21 can be programmed to alter the vertical position at which the vials 14 are placed and held in the vial holder 54. The vial pallet 27 is then lowered by the pallet lift 228 to the vial pallet transport assembly 90, and the pallet 27 is moved out of the vial loader module 154. As shown in FIG. 34, from the vial loader module 154, the now fully loaded vial pallet 27 is conveyed to the vial holder placement modules 260.

Preferably, the system 21 includes redundancy of certain components including the vial holder placement modules 260, the vial/device sterilization booths 270 and the vial holder removal modules 340 as shown in FIG. 3. These redundancies generally improve system efficiency.

At the vial holder placement modules 260, the vial holder 54 is lifted off of the container holder supports 50 of the vial pallet 27 and placed atop the top holder supports 36 by the pick and place unit 264 and the lift and locate unit 266. The pin holes 70 (FIG. 11) of the vial holder 54 generally are aligned with and receive the locating pins 40 (FIG. 4) of the top holder supports 36. Placing the vial pallet 27 into this stacked connecting position vertically coaxially aligns the vial 14 and reconstitution device 10 so that they can be pushed together and connected to one another.

After the vial pallet 27 has been placed into the stacked connecting position as shown in FIG. 35, the vial pallet 27 is conveyed into the vial/device sterilization booth 270. In the vial/device sterilization booth 270 (FIG. 3), the vial 14 and reconstitution device 12 are sterilely connected to form the reconstitution device/vial subassembly 349 as was described above in detail (FIGS. 1, 2, and 2A).

As discussed, the sterilization booths generally include a sterilization source, or radiation source which is preferably a low-energy electron beam source. By training the resulting electron clouds of electron beam tubes to overlap at the position of a pallet window of either a bag pallet or a vial pallet positioning device, an electron "flood area" is created. This flood area is the preferred location for connection of the components. The sterilizing field, or flood area, insures that sterilization is maintained at every corner, crevice, and surface of the components. That is, shadowing caused by juxtaposition of surfaces is minimized, if not eliminated. Electrons are scattered in the flood areas to aid in sterilization.

Figure 62:
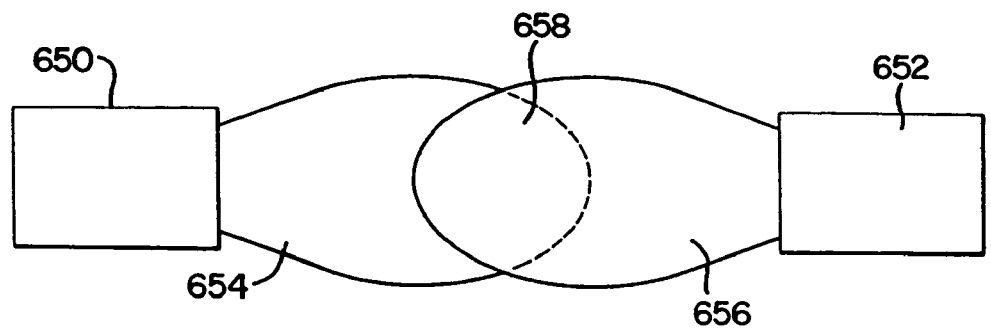
FIG. 62 is a schematic side view of sterilizing fields according to one embodiment of the present invention.
Figure 63:
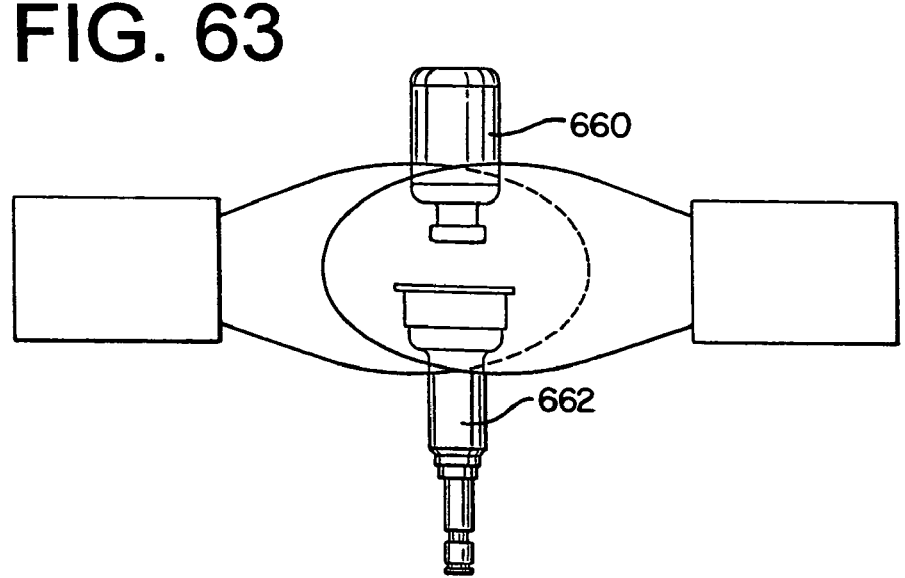
FIG. 63 is a schematic side view of sterilizing fields according to another embodiment of the present invention.

FIGS. 62-64 generally show the intersection of the component parts within the flood area 658 created by e-beam tubes 650, 652 according to the present invention. As shown in FIG. 62, the e-beams tubes 650, 652 each generally form an electron cloud 654, 656. The e-beams 650, 652 are preferably positioned opposite to one another such that the electron clouds 654, 656 overlap to form an area of relatively concentrated radiation called the flood area 658 or sterilizing field. Electrons are scattered in the flood areas or sterilizing fields. As shown in FIGS. 63 and 64, the snap connection of a container 660, which is typically either a drug vial or flexible diluent container, to a reconstitution device 662, preferably occurs within the overlapping connection or flood area 658. This arrangement is preferably used in both the vial/device sterilization booth 270 and the bag/device sterilization booth 520.

The flood area 658 is preferably localized to the connection area in which the container/device connection is performed. For example referring to FIG. 35, in the vial/device sterilization booth 270, the flood area preferably encompasses the area in which the four connections between the vial 14 and the reconstitution device 10 are made within the vial pallet 27. When the vial pallet 27 is in the stacked connecting position with the vial holder 54 stacked on top of the device holder subassemblies 35, as shown in FIG. 10, a window is created between the vial holder 54 and the device holder subassemblies 35. This window exposes a portion of the drug vial 14 and the gripper assembly of the reconstitution device 10 to any electron beam cloud which may be present. In this manner, the vial pallet 27 acts as a positioning assembly to properly position the contemplated connection within the sterilizing field.

The electron beam tubes of the vial/device sterilization booth 270 are preferably continuously emitting. However, the emitting electron beam tubes are shielded from the connection area until the components are properly positioned to make a connection within a sterilizing field. The shielding is generally performed by the shutters 294,296.

Referring again to FIG. 35, within the sterilization chamber 272, the vial pallet 27 is positioned between the two electron beam sources. At this time, the shutters 294, 296 are in a closed position. In the present embodiment, the shutters 294, 296 are liquid cooled steel panels used to block the electron beam window before and after component sterilization and connection. The boustrophedonically arranged coolant flow preferably travels through the hollow upper and lower portion of the shutters 294, 296. However, as with the sterilization booth housing, it is necessary that the shutters 294, 296 are dense enough to provide proper shielding, so the coolant flow (which require hollowing of the panel) is preferably absent from a central portion of the shutters where direct incidence of the electron beam is realized.

After proper positioning of the vial pallet 27 within the sterilization chamber 272 the vial back-up mechanism 307 is actuated, as shown in FIG. 35A. The vial back-up mechanism 307 generally descends onto the vial holder 54 until the vial holder shield 312 has been positioned such that it forms a continuous radiation shield with the end plates 60 and side plates 64 of the vial holder 54. The descending vial back-up mechanism 307 also moves the vial positioning tool 314 into contact with the vials 14. The vials 14 are pushed downward into a connecting position. The vial back-up mechanism 307 and vial positioning tool 314 then stop and maintain that position until after the connection between the vial 14 and reconstitution device 10 has been made. The vial back-up mechanism 307 can be programmed to move and position the vial 14 as desired closing the exposure process.

The shutters 294, 296 are generally attached to the pneumatic actuator 302, 304 which is responsive to a controller (not shown). When the chamber doors are in a closed position (FIG. 35), the appropriate controller can activate the pneumatic actuators 302, 304 to raise the shutters 294, 296 (FIG. 35A). At this point, component exposure is controlled by the position of the components within the resulting electron cloud (preferably within the electron flood area) as well as the time of exposure (i.e., the time the shutters are raised).

Once an appropriate level of exposure has been administered to ensure sterility of the desired portions of the drug vial 14 and the reconstitution device 10, the snap-closure mechanism 320 is actuated. Referring to FIG. 36, the four independent pneumatic cylinders 324 of the snap-closure mechanism extend upward to the device holder subassembly 35 of the vial pallet 27 and move the device nests 48 upward until the reconstitution device 10 and vial 14 snap together within the flood area 658. Each of the independent pneumatic cylinders preferably includes an electronic position feedback sensor 326 which monitors the cylinder position. Two parameters, including a linear cylinder monitor and a built in linear encoder, are generally used to apply the correct force to achieve a successful snap fit between the components. Load cells may be used to set the parameters for consistently effecting a snap closure as is well understood in the art.

It is understood that the vial 14 may have two positions within the vial holder 54. In one preferred embodiment, the vial 14 may be repositioned one time during exposure in the sterilization field to better control any potential stray sterilization dose to the vial 14. As shown in FIG. 35, the vial 14 can be moved within the vial holder 54 during the process if desired. As can be understood, the vial 14 has a generally flat surface (i.e., generally proximate the target area of the closure of the vial) requiring sterilization. The structure of the device 10 requiring sterilization, generally proximate the septum at the gripper assembly as shown in FIGS. 2 and 2A, has varying depths. As opposed to a generally flat surface, the structure having varying depths may require additional exposure time in the sterilization field to assure appropriate sterility. With a flat surface, the vial 14 may not need the same amount of exposure time to assure appropriate sterility. Accordingly, as discussed above, the vial 14 may be placed at a higher position within the vial holder 54 such that when the shutters 294,296 move to expose the sterilization field, the vial 14 initially experiences less dose during the exposure process. This enhances the control of the amount of dose the vial 14 experiences during the process. When it is time to connect, the vial 14 can be repositioned one time during the exposure and then connected to the device 10. This provides better overall control of the dose exposed to the vial 14. As is understood, the initial position of the vial 14 in the vial holder 54 can be varied and movement controlled as desired to enhance the sterile connection process.

Preferably, the sterile connection of a container and a reconstitution device is verified through the use of a dosimeter positioned on a pallet such that the dosimeter measures or approximates the dose of radiation incident upon the connecting components. Generally, a sterility assurance level (SAL), defined as a measure of the probability that one unit in a batch will remain non-sterile after being exposed to a specific sterilant, is selected. A dosage that will provide the desired sterility assurance level is then determined. By implementing a verification of sterility process, wherein the dosimeter on selected pallets passing through a sterilization booth is examined to validate a proper dosage of radiation, the desired sterility can be ensured. Such a process is described in detail in commonly-owned U.S. application Ser. No. 10/745,466, entitled "Method And Apparatus For Validation Of Sterilization Process," filed concurrently herewith, which application has been previously discussed and incorporated by reference into this specification.

After a snap fit has been made between the vial 14 and the reconstitution device 10, the shutters 294, 296 preferably close similar to their initial position as shown in FIG. 35. The pneumatic cylinders 324 also withdraw from the vial pallet 27. The springs 44 within the device holder subassemblies 35 of the vial pallet 27 then preferably move the device nest 48 back to its original position within each of the device holder subassemblies 35. In addition, the vial back-up mechanism 307 retracts to its original position. The reconstitution device 10 remains connected to the vial 14 as shown in FIG. 10. When connected, the vial 14 is positioned within the gripper assembly of the reconstitution device 10 to form the reconstitution device/vial subassembly 349. The vial pallet 27 is then generally moved out of the sterilization chamber 272 and another vial pallet 27 moved in.

As generally discussed above, each of the pre-sterilization chambers 274, 521, post sterilization chambers 276, 523 and sterilization chambers 272, 522 of the sterilization booths 270,520, preferably includes its own independent conveyor. The movement of pallets through the three chambered sterilization booths 270, 520 is generally the same for both the vial/device sterilization booth 270 and the bag/device sterilization booth 520, and will be described generally here.

Figure 61A:
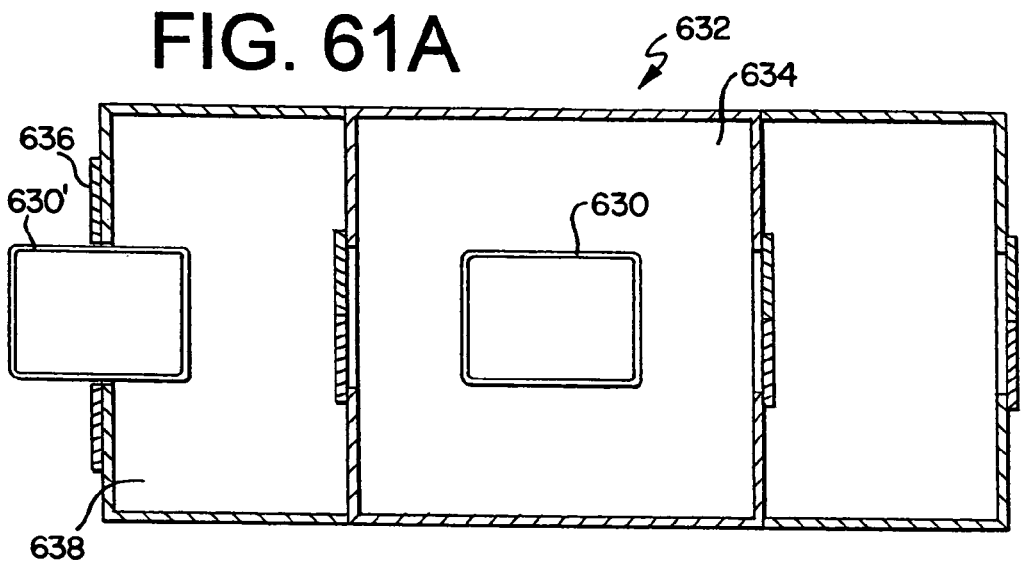
FIGS. 61A-C are schematic top views of a sterilization booth according to one embodiment of the present invention.
Figure 61B:
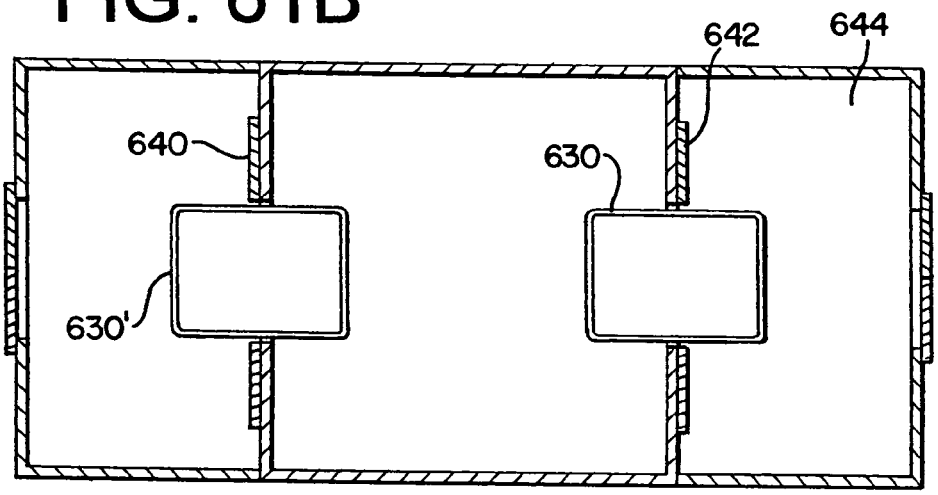
Figure 61C:
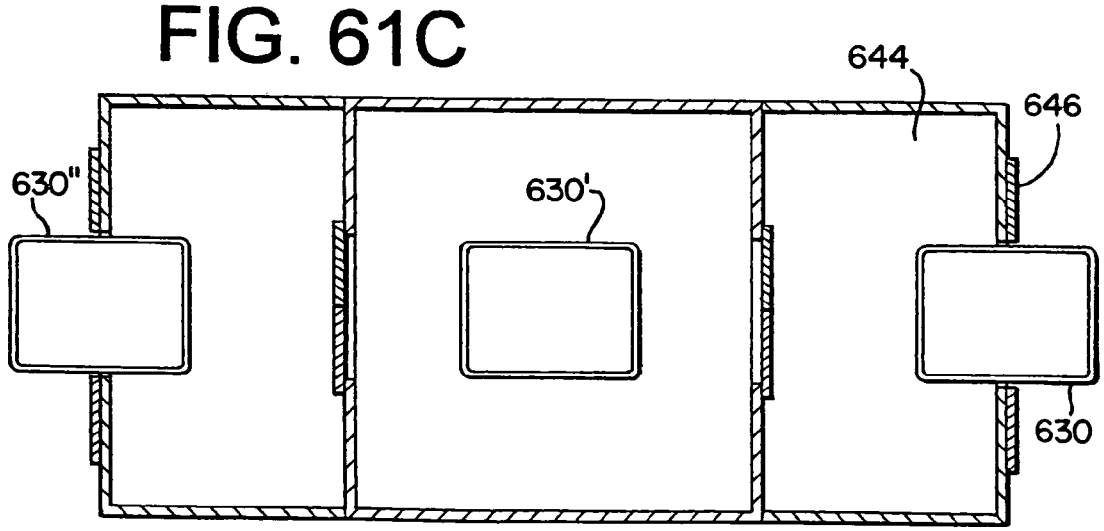

Referring now to FIGS. 61A-C, one example of the movement of a pallet 630 through a three chambered booth 632 according to the present invention can be generically understood. Beginning with a booth having a leading pallet 630 already in a middle, sterilization chamber 634, FIG. 61A shows the opening of a first door 636 into a pre-sterilization chamber 638. A second pallet 630' is conveyed into the pre-sterilization chamber 638, and held until the first door 636 into the pre-sterilization chamber 638 is again closed. At this time, the lead pallet 630 in the sterilization chamber 634 is subject to sterile connection of component containers and reconstitution devices.

Then, as shown in FIG. 61B, both a second door 640 between the pre-sterilization chamber 638 and the sterilization chamber 634, and a third door 642 between the sterilization chamber 634 and a post-sterilization chamber 644 are opened. The lead pallet 630 is conveyed into the post-sterilization chamber 644, while the second pallet 630' is conveyed into the sterilization chamber 634 simultaneously. Then, both the second door 640, and the third door 642 close.

Next, as shown in FIG. 61C, the first door 636 into the pre-sterilization booth 638, and a fourth door 646 out of the post-sterilization chamber 644, open. The lead pallet 630 exits the post-sterilization chamber 644, and a third pallet 630" is introduced into the pre-sterilization chamber 638. At this point the doors generally close. Now all of the doors are closed. The lead pallet 630 has completely exited the booth 632, the second pallet 630' is in the sterilization chamber 634 undergoing the sterile connect process. The third pallet 630" is now located in the pre-sterilization chamber 638. The sequence is then repeated from the opening of the doors 640, 642 leading into and out of the sterilization chamber 634. Following such a progression maintains a sealed door on either side of the electron source at all times, thereby providing a full-time barrier against the escape of stray radiation from the sterilization chamber. Naturally, other sequences may be devised and safety features added to achieve this important safety precaution.

Movement of the pallets is controlled by the three independent conveyor surfaces of the pre-sterilization chamber 636, sterilization chamber 634, and post sterilization chamber 644. The pre-sterilization conveyor surface is responsible for receiving a pallet from the system and transporting the pallet into the pre-sterilization chamber 636. The pre-sterilization conveyor surface and the sterilization chamber conveyor surface work together to transport the pallet into the sterilization chamber. After sterilization, the sterilization chamber conveyor surface and the post sterilization conveyor surface cooperate to position the pallet within the post-sterilization chamber. Finally, the post sterilization conveyor surface transports the pallet to the system 21 for resumed handling. With alternate indexing through the chambers, variations on the number of conveyor surfaces used may be made. Those skilled in the art will understand how to correlate the indexing of pallets to the movement of the conveyor surfaces should variations be necessary.

Upon exiting the sterilization booth 270 (FIG. 3), the vial pallet transfer assembly 90 conveys the vial pallet 27 to the vial holder removal module 340. A soft stop 592 positions the vial pallet 27 at the vial holder removal module 340. The vial holder 54 is lifted off of the top holder supports 36 by the pick and place unit 344 and the lift and locate unit 346. As shown in FIG. 40, the vial pallet 27 is then returned to the unstacked loading position wherein the vial holder 54 is atop the container holder supports 50. The reconstitution device/vial subassembly 349 is preferably retained in the vial holder 54 portion of the vial pallet 27. The container holder supports 50 are preferably tall enough to insure the reconstitution device 10 does not contact the vial pallet base 29 when the vial pallet 27 is returned to the unstacked loading position.

Figure 42:
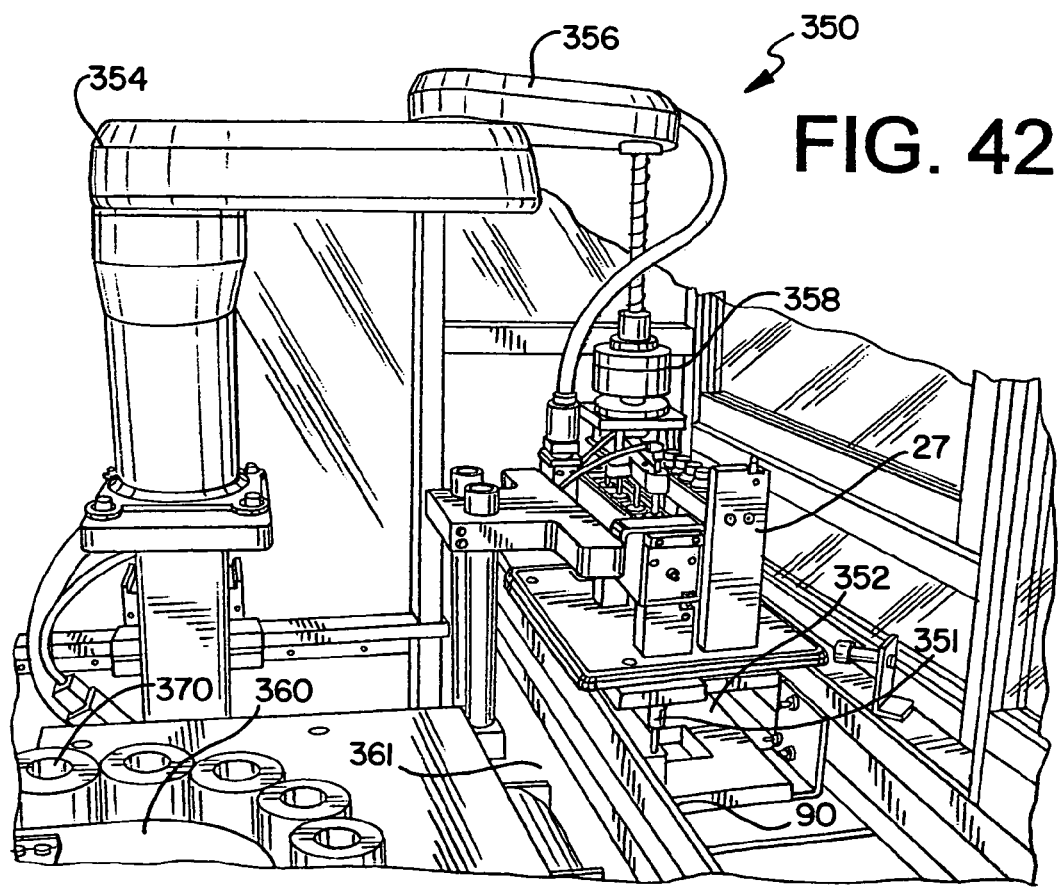
FIG. 42 is another partial perspective view of the depalletizing device and vial station of FIG. 41.

The vial pallet transport assembly 90 then generally conveys the vial pallet to the depalletize device and vial module 350, as shown in FIG. 42. The pallet lift and release mechanism 350 generally first lifts the vial pallet 27. Then the transfer robot 354 generally grasps the four reconstitution device/vial subassemblies 349. The pallet lift and release mechanism 350 then preferably opens the vial holder 54 portion of the vial pallet 27, and the reconstitution device/vial subassemblies 349 are lifted clear of the vial holder 54 by the transfer robot 354. The transfer robot 354 then deposits the reconstitution device/vial subassemblies 349 into the pucks 370 of the shrinkband applicator 360. The unloaded vial pallets 27 then proceed along the vial pallet transfer assembly 90 to begin another cycle through the first cell 23 of the apparatus 21. A plurality of vial pallets 27 generally circulate through the apparatus 21 simultaneously.

As shown in FIGS. 43-44, the reconstitution device/vial subassemblies 349 in the pucks 370 are then moved through the shrinkbanding process. The process is preferably fully automated, and generally includes placing a shrinkband ring over the sterilely connected vial and reconstitution device at the shrinkband application station 365 so that the shrinkband covers the connected portions as generally shown in FIG. 2A. The pucks 370 then generally move along the free puck conveyor 368 through the oven 367. The heat from the oven preferably shrinks the shrinkband ring so that it forms to the contours of a portion of the reconstitution device/vial subassembly 349.

The pucks 370 exit the oven 367 and proceed to the palletize device and vial subassembly station 448 of the bag/device subassembly connection system 25 as shown in FIG. 51. The bag pallet 402 is preferably already loaded with a bag 16 upon arrival at the palletize device and vial subassembly station 448.

Operation of Bag/Device Subassembly Connection System 25 (Second Cell)

Referring to FIGS. 45-46, the loading of bags 12 onto the bag pallet 402 is generally performed by operators using a bag pallet opener 488 (FIG. 3) to open the bag gripper 420. The operator then generally loads bags 12 onto the bag pallet 402 (FIG. 45). In some embodiments, loading of the bags 12 may be an automated process performed by robots.

Loading of the reconstitution device/vial subassemblies 349 onto the bag pallet 402 is generally an automated process. The bag pallet conveyor assembly 444 generally transports the bag pallet 402 to the palletize device/vial subassembly module 448, as illustrated in FIG. 52. A soft stop 602 (FIG. 3) generally properly positions the bag pallet 402. The transfer robot 452 of FIG. 51 then removes the shrinkbanded reconstitution device/vial subassemblies 349 from the pucks 370 and loads them onto a bag pallet 402. The pallet release mechanism 464 of FIG. 52 opens the vial and device subassembly holder 408 on the bag pallet 402 so that the subassembly 349 can be loaded.

The fully loaded bag pallet 402 is then conveyed by the bag pallet transport assembly 444 to the nozzle blow-off module 500 of FIG. 53. A soft stop 604 (FIG. 3) generally properly positions the bag pallet 402 within the nozzle blow-off station 500. At the nozzle blow-off station 500, any water droplets or loose particulate matter is blown off of the port connector 30 of the bag 12 before it enters the bag/device subassembly sterilization booth 520.

From the nozzle blow-off module 500 the loaded bag pallet 402 is transported into the bag/device sterilization booth 520, the operation of which is generally described below with the understanding that the operation is similar to the vial/device sterilization booth 270 described above.

The bag pallet 402 also acts as a positioning assembly to properly position the bag 12 and the reconstitution device/vial subassembly 349 such that the bag port connector 30 and the reconstitution device 10 are positioned within the flood area created by the electron beam emitters of the bag/device sterilization booth 520 (FIG. 3) prior to the contemplated connection between these components. The rear shielding plate 426 of the bag pallet 402 generally has a window 434 formed in it to allow exposure of the bag port connector 30 and the reconstitution device sleeve connector port 17 to the flood area from the rear. The front portion of the bag pallet 402 generally has no built in shielding.

Shielding of the front portion is accomplished by the heat shield 548 of the bag/device sterilization booth 520, as shown in FIG. 55. The heat shield 548 generally includes the upper plate 550 and the lower plate 552. As previously discussed, the lower plate 552 is preferably movable up and down vertically. When the lower plate 552 is moved down, a window exists between the plates which preferably corresponds to the positioning of the bag port connector 30 and sleeve connector port 17 when a bag pallet 402 is positioned for performing a sterile connection within the sterilization chamber 552.

The sterilization chamber 552 of the bag/device sterilization booth 520 is different from that of the vial/device sterilization booth 270 because it does not include a vial back-up mechanism. The device/vial subassembly 349 is immovably secured by the device and vial subassembly gripper. It holds the device/vial subassembly 349 stationary while the bag 12 is preferably moved upward wherein the port connector assembly on the bag 12 is snap fit to the sleeve assembly of the reconstitution device 10.

Referring to FIGS. 55 and 56, the bag 12 is generally positioned within the bag pallet 402 in the sterilization chamber 522. After the bag pallet 402 is properly positioned in the sterilization chamber 522, the shutters 532, 534 are moved upward creating a flood area which preferably encompasses both the port connector assembly 30 and the sleeve assembly 17. The snap closure mechanism 558 is then actuated and its four pneumatic cylinders 562 move upward from a first loading position, pushing the bag back support plate 436 (FIG. 46) and the bag 12 secured to it upward until it forms a snap connection with the stationary reconstitution device 10 at a second connecting position (i.e., the port connector assembly 30 snap fits into the portion 17 of the sleeve assembly of the device 10). It is understood that this connection is also made in a concentrated sterilizing field as shown in FIGS. 62-64. Once connected, a reconstitution assembly 1 is formed. Preferably, the sterile connection of a bag and a reconstitution device is verified through the use of a dosimeter positioned on a pallet such that the dosimeter measures or approximates the dose of radiation incident upon the connecting components. Generally, a sterility assurance level (SAL), defined as a measure of the probability that one unit in a batch will remain non-sterile after being exposed to a specific sterilant, is selected. A dosage that will provide the desired sterility assurance level is then determined. By implementing a verification of sterility process, wherein the dosimeter on selected pallets passing through a sterilization booth is examined to validate a proper dosage of radiation, the desired sterility can be ensured.

As in the vial/device sterilization booth 270, two parameters, including a linear cylinder monitor and a built in linear encoder, are generally used to apply the correct force to achieve a successful snap fit between the components. After the bag 12 and reconstitution device 10 have been connected, the pneumatic cylinders 562 preferably move downward returning to the first loading position. The bag pallet 402 is then generally moved out of the sterilization chamber 520.

Upon exiting the sterilization booth 520, the bag pallet transfer assembly 444 conveys the bag pallet 402 to a bag reject station 606. At the bag reject station 606, either an operator or an automated bag inspection assembly 608 preferably inspects the fully assembled reconstitution assemblies 1. Reject assemblies are removed from the bag pallet 402.

From the bag reject station 606, the bag pallet transfer assembly 444 conveys good parts to the depalletize reconstitution device assembly 568 as shown in FIGS. 59 and 60. A soft stop 606 as shown in FIG. 3 generally positions the bag pallet 402 at the depalletize reconstitution device assembly 568. The pick and place assembly 572 in conjunction with the pallet release mechanism then generally removes the reconstitution device assemblies 10 from the bag pallet 402 and places them on a belt conveyor 584. The unloaded bag pallets 402 then proceed along the bag pallet transfer assembly 444 to begin another cycle through the second cell 25 of the system 21. Preferably, a plurality of bag pallets 406 move through the apparatus 21 simultaneously. It is also understood that a plurality of vial pallets 27 move through the apparatus 21 simultaneously.

While the specific embodiments have been illustrated and described, numerous modifications come to mind without significantly departing from the spirit of the invention, and the scope of protection is only limited by the scope of the accompanying claims.

What is claimed is:

1. An apparatus for the sterile connecting of a container and a reconstitution device comprising:
    a sterilizing emitter assembly for emitting radiation to define a sterilizing field;
    a connecting mechanism comprising a positioning assembly including a container holder configured to hold a container, and a reconstitution device holder configured to hold a reconstitution device; and
    wherein the connecting mechanism is configured to connect the container and reconstitution device in the sterilizing field; and
    wherein the sterilizing emitter assembly comprises a low energy electron beam tube, a container pallet shielding configured to shield the positioning assembly from electron beam radiation during a connecting process, wherein the container pallet shielding includes movable shutters configured to shield the positioning assembly to the sterilizing field in a first closed position and to expose the positioning assembly to the sterilizing field in a second open position and a vial back-up mechanism configured to position the container within the positioning assembly.

2. The apparatus of claim 1 wherein the positioning assembly is a pallet.

3. The apparatus of claim 2 wherein the container is a vial.

4. The apparatus of claim 1 wherein the connecting mechanism comprises a snap-closure assembly.

5. The apparatus of claim 4 wherein the snap-closure assembly comprises a cylinder configured to move the positioning assembly into a connecting position such that the container and the reconstitution device are snap-fit together.

6. The apparatus of claim 5 wherein the snap-closure assembly comprises a cylinder configured to move the container or the reconstitution device into a connecting position such that the container and the reconstitution device are snap-fit together.

7. The apparatus of claim 1 further comprising a conveyor assembly upon which a plurality of positioning assemblies are supported and moved from a loading position to a connecting position.

8. The apparatus of claim 7 further comprising a positioning assembly loader wherein the conveyor assembly is arranged to transport the positioning assembly from the loader to the connecting mechanism.

9. The apparatus of claim 8 wherein the positioning assembly loader includes a device loader and a vial loader.

10. The apparatus of claim 9 further comprising a positioning assembly unloader wherein the conveyor assembly is arranged to transport the positioning assembly from the connecting mechanism to the positioning assembly unloader.

11. The apparatus of claim 1 further comprising a housing which houses the sterilizing emitter assembly, the positioning assembly, and the connecting mechanism.

12. The apparatus of claim 11 wherein the housing comprises a pre-sterilization chamber, a sterilization chamber, and a post sterilization chamber.

13. The apparatus of claim 12 wherein the housing comprises entry doors and exit doors from each of the pre-sterilization chamber, the sterilization chamber, and the post sterilization chamber.

14. The apparatus of claim 13 wherein the housing further comprising individual conveyors within each of the pre-sterilization chamber, the sterilization chamber, and the post sterilization chamber.

15. An apparatus for the sterile connecting of a container and a reconstitution device comprising:
    a sterilizing emitter assembly for emitting radiation to define a sterilizing field;
    a connecting mechanism comprising a positioning assembly including a container holder configured to hold a container, and a reconstitution device holder configured to hold a reconstitution device;
    wherein the connecting mechanism is configured to connect the container and reconstitution device in the sterilizing field; and
    the sterilizing emitter assembly comprising a container pallet shielding configured to shield the positioning assembly from electron beam radiation during a connecting process, wherein the container pallet shielding includes a vial back-up mechanism configured to position the container within the positioning assembly.

16. An apparatus for the sterile connecting of a container and a reconstitution device comprising:
    a sterilizing emitter assembly for emitting radiation to define a sterilizing field;
    a connecting mechanism comprising a positioning assembly including a container holder configured to hold a container, and a reconstitution device holder configured to hold a reconstitution device; and
    wherein the connecting mechanism is configured to connect the container and reconstitution device in the sterilizing field;
    a second sterilizing emitter assembly;
    a second positioning assembly;
    a second connecting mechanism cooperatively engageable with the second positioning assembly;
    a heat shield arranged to selectively shield a portion of the second positioning assembly configured to hold a container from the second sterilizing emitter assembly;
    a second housing which houses the second sterilizing emitter assembly, the heat shield, and the second positioning assembly; and
    wherein the second housing is operably connected to the first housing such that a container and a reconstitution device sterilely connected in the first housing are transported to the second housing and sterilely connected to a second container.

17. An apparatus for the sterile connecting of a container and a drug reconstitution device comprising:
    a first sterilization source configured to emit radiation the bounds of which define a sterilizing field;

means for positioning a first container and a reconstitution device within a connection area;

means for providing relative motion between the first container and the reconstitution device to connect the same within the sterilizing field;

a second sterilization source configured to emit radiation the bounds of which define a second sterilizing field;

means for positioning the reconstitution device and a second container within a second connection area;

means for providing relative motion between the second container and the reconstitution device to connect the same within the sterilizing field; and conveyance means for conveying the reconstitution device between the first sterilization source and the second sterilization source.

* * * * *